US008815504B2

(12) United States Patent
Makarov et al.

(10) Patent No.: US 8,815,504 B2
(45) Date of Patent: *Aug. 26, 2014

(54) DNA AMPLIFICATION AND SEQUENCING USING DNA MOLECULES GENERATED BY RANDOM FRAGMENTATION

(75) Inventors: Vladimir L. Makarov, Ann Arbor, MI (US); Irina Sleptsova, Ann Arbor, MI (US); Emmanuel Kamberov, Ann Arbor, MI (US); Eric Bruening, Chelsea, MI (US)

(73) Assignee: Rubicon Genomics, Inc., Ann Arbor, MI (US)

( * ) Notice: Subject to any disclaimer, the term of this patent is extended or adjusted under 35 U.S.C. 154(b) by 571 days.

This patent is subject to a terminal disclaimer.

(21) Appl. No.: 12/697,886

(22) Filed: Feb. 1, 2010

(65) Prior Publication Data

US 2010/0145037 A1    Jun. 10, 2010

Related U.S. Application Data

(63) Continuation of application No. 10/293,048, filed on Nov. 13, 2002, now Pat. No. 7,655,791.

(60) Provisional application No. 60/338,224, filed on Nov. 13, 2001.

(51) Int. Cl.
C12Q 1/68 (2006.01)
C12P 19/34 (2006.01)

(52) U.S. Cl.
USPC .......................................... 435/6.1; 435/91.1

(58) Field of Classification Search
None
See application file for complete search history.

(56) References Cited

U.S. PATENT DOCUMENTS

| | | | | |
|---|---|---|---|---|
| 5,506,100 | A | 4/1996 | Surzycki et al. | 435/6 |
| 5,714,318 | A | 2/1998 | Sagner et al. | 435/6 |
| 5,759,821 | A | 6/1998 | Teasdale | 435/91.2 |
| 5,759,822 | A | 6/1998 | Chenchik et al. | 435/91.2 |
| 5,789,206 | A | 8/1998 | Tavtigian et al. | 435/91.2 |
| 5,814,444 | A | 9/1998 | Rabinovitch | 435/6 |
| 5,871,820 | A | 2/1999 | Hasz et al. | 427/419.2 |
| 5,968,743 | A | 10/1999 | Matsunaga et al. | 435/6 |
| 6,060,245 | A | 5/2000 | Sorge et al. | 435/6 |
| 6,107,023 | A | 8/2000 | Reyes et al. | 435/6 |
| 6,114,149 | A | 9/2000 | Fry et al. | 435/6 |
| 6,124,120 | A | 9/2000 | Lizardi | 435/91.2 |
| 6,280,949 | B1 | 8/2001 | Lizardi | 435/6 |
| 6,365,375 | B1 | 4/2002 | Dietmaier et al. | 435/91.1 |
| 6,537,757 | B1 | 3/2003 | Langmore et al. | 435/6 |
| 6,762,022 | B2 | 7/2004 | Makarov et al. | 435/6 |
| 7,186,512 | B2 | 3/2007 | Martienssen et al. | 435/6 |
| 2001/0051342 | A1* | 12/2001 | Farrell | 435/6 |
| 2002/0042059 | A1 | 4/2002 | Makarov et al. | 435/6 |
| 2002/0058250 | A1 | 5/2002 | Firth | 435/6 |
| 2002/0106649 | A1 | 8/2002 | Lizardi et al. | 435/6 |
| 2003/0013671 | A1 | 1/2003 | Mineno et al. | 506/17 |
| 2003/0082543 | A1 | 5/2003 | Su et al. | 435/6 |
| 2003/0082572 | A1 | 5/2003 | Spier et al. | 435/6 |

FOREIGN PATENT DOCUMENTS

| | | |
|---|---|---|
| EP | 0 684 315 | 3/1995 |
| EP | 0 999 285 | 5/2000 |
| JP | 08173164 | 12/1994 |
| JP | 2000-106876 | 4/2000 |
| WO | WO 93/24654 | 12/1993 |
| WO | WO 98/15652 | 4/1998 |
| WO | WO 00/17390 | 3/2000 |

OTHER PUBLICATIONS

"Transferases," Gibco BRL Products & Reference Guide, pp. 15-26, 1997/1998.

Agarwal et al., "PCR amplification of highly GC-rich DNA template after denaturation by NaOH," *Nucleic Acids Research*, 21:5283-4, 1993.

Anderson, "Shotgun DNA sequencing using cloned DNase I-generated fragments," *Nucleic Acids Research*, 9:3015-27, 1981.

Barbaux el al., "Use of degenerate oligonucleotide primed PCR (DOP-PCR) for the genotyping of low-concentration DNA samples," *J. Mol. Med.*, 79:329-332, 2001.

Beekman et al., "A powerful and rapid approach to human genome scanning using small quantities of genomic DNA," *Genet. Res.*, 77:129-134, 2001.

Bohlander et al., "A method for the rapid sequence-independent amplification of microdissected chromosomal material," *Genomics*, 13:1322-24, 1992.

Campbell and Jackson, "The effect of divalent cations on the mode of action of DNase I," *J. Biol. Chem.*, 255:3726-35, 1980.

Cheung and Nelson, "Whole genome amplification using a degenerate oligonucleotide primer allows hundreds of genotypes to be performed on less than one nanogram of genomic DNA," *Proc. Natl. Acad. Sci. USA*, 93:14676-9, 1996.

Cusi et al., "PCR amplification of GC-rich templates containing palindromic sequences using initial alkali denaturation," *BioTechniques*, 12:502-4, 1992.

(Continued)

*Primary Examiner* — Kenneth R. Horlick
*Assistant Examiner* — David Thomas
(74) *Attorney, Agent, or Firm* — Parker Highlander PLLC

(57) ABSTRACT

The present invention is directed to methods to prepare a DNA molecule or a plurality of DNA molecules by random fragmentation. In some embodiments, the present invention regards preparing a template for DNA sequencing by random fragmentation. In specific embodiments, the random fragmentation comprises chemical fragmentation, mechanical fragmentation, or enzymatic fragmentation. In further specific embodiments, a universal sequence is attached to the 3' end of the DNA fragments, such as by ligation of an adaptor sequence or by homopolymeric tailing with terminal deoxynucleotidyltransferase. In other embodiments, a library is prepared with methods of the present invention.

22 Claims, 28 Drawing Sheets

(56) References Cited

OTHER PUBLICATIONS

Dean et al., "Comprehensive human genome amplification using multiple displacement amplification," *Proc. Natl. Acad. Sci. USA*, 99:5261-6, 2002.
Eigner et al., "The thermal degradation of nucleic acids," *Biochim. Biophys. Acta.*, 51:165-8, 1961.
Fu et al., "Sequencing double-stranded DNA by strand displacement," *Nucleic Acids Research*, 25:677-9, 1997.
Greer and Zamenhof, "Studies on depurination of DNA by heat," *J. Mol. Biol.*, 4:123-41, 1962.
Guan et al., "Generation of band-specific painting probes from a single microdissected chromosome," *Human Molecular Genetics*, 2:1117-1121, 1993.
Guilfoyle et al., "Ligation-mediated PCR amplification of specific fragments from a class-II restriction endonuclease total digest," *Nucleic Acids Research*, 25:1854-8, 1997.
Hawkins et al., "Whole genome amplification—applications and advances," *Curr. Opin. Biotechnol.*, 13:65-7, 2002.
Igloi, "Substrate properties of fluorescent ribonucleotides in the terminal transferase-catalyzed labeling of DNA sequencing primers," *BioTechniques*, 21:1084-92, 1996.
Jones and Winistorfer, "Amplification of 4-9-kb human genomic DNA flanking a known site using a panhandle PCR variant," *BioTechniques*, 23:132-8, 1997.
Kaiser et al., "Specific-primer-directed DNA sequencing using automated fluorescence detection," *Nucleic Acids*, 17:6087-102, 1989.
Kittler et al., "A whole genome amplification method to generate long fragments from low quantities of genomic DNA," *Anal. Biochem.*, 300:237-44, 2002.
Klein et al., "Comparative genomic hybridization, loss of heterozygosity, and DNA sequence analysis of single cells," *Proc. Natl. Acad. Sci. USA*, 96:4494-4499, 1999.
Kilger and Pääbo, "Direct DNA sequence determination from total genomic DNA," *Nucleic Acids Research*, 25:2032-34, 1997.
Kinzler and Vogelstein, "Whole genome PCR: application to the identification of sequences bound by gene regulatory proteins," *Nucleic Acids Research*, 17:3645-53, 1989.
Kusov et al., "A new G-tailing method for the determination of the poly(A) tail length applied to hepatitis A virus RNA," *Nucleic Acids Research*, 29:e57-7, 2001.
Kuukasjarvi et al., "Optimizing DOP-PCR for universal amplification of small DNA samples in comparative genomic hybridization," *Genes Chromosomes Cancer*, 18:94-101, 1997.
Lindahl and Nyberg, "Rate of depurination of native deoxyribonucleic acid," *Biochemistry*, 11:3610-8, 1972.
Lucito et al., "Genetic analysis using genomic representations," *Proc. Natl. Sci. USA*, 95:4487-92, 1998.
Mori et al., "Molecular, biochemical and immunological analyses of porcine pancreatic DNase I," *Biochim. Biophys. Acta.*, 1547:275-87, 2001.
Nishigaki et al., "Whole genome sequence-enabled prediction of sequences performed for random PCR products of *Escherichia coli*," *Nucleic Acid Research*, 28:1879-84, 2000.
Office Communication, issued in U.S. Appl. No. 10/293,048, mailed Aug. 30, 2005.
Office Communication, issued in U.S. Appl. No. 10/293,048, mailed Nov. 28, 2005.
Office Communication, issued in U.S. Appl. No. 10/293,048, mailed Jun. 6, 2006.
Office Communication, issued in U.S. Appl. No. 10/293,048, mailed Sep. 6, 2006.
Office Communication, issued in U.S. Appl. No. 10/293,048, mailed May 4, 2007.
Office Communication, issued in U.S. Appl. No. 10/293,048, mailed Feb. 20, 2008.
Office Communication, issued in U.S. Appl. No. 10/293,048, mailed Nov. 21, 2008.
Pfeifer et al., "Chromatin structure analysis by ligation-mediated and terminal transferase-mediated polymerase chain reaction," *Meth. Enzym.*, 304:548-71, 1999.
Reyes and Kim, "Sequence-independent, single-primer amplification (SISPA) of complex DNA populations," *Molecular and Cellular Probes*, 5:473-81, 1991.
Rudi et al., "Restriction cutting independent method for cloning genomic DNA segments outside the boundaries of known sequences," *BioTechniques*, 27:1170-2, 1999.
Schiefermayr and Igloi, "Degradation of DNA sequencing primers by a terminal transferase-associated exonuclease," *Anal. Biochem.*, 230:180-2, 1995.
Shyamala and Ames, "Genome walking by single-specific-primer polymerase chain reaction: SSP-PCR," *Gene*, 84:1-8, 1989.
Smith, "Ligation-mediated PCR of restriction fragments from large DNA molecules," *PCR Methods Appl.*, 2:21-7, 1992.
Snabes et al., "Preimplantation single-cell analysis of multiple genetic loci by whole-genome amplification," *Proc. Natl. Acad. Sci. USA*, 91:6181-6185, 1994.
Wells and Delhanty, "Comprehensive chromosomal analysis of human preimplantation embryos using whole genome amplification and single cell comparative genomic hybridization," *Mol. Hum. Reprod.*, 6:1055-62, 2000.
Wells et al., "Detailed chromosomal and molecular genetic analysis of single cells by whole genome amplification and comparative genomic hybridisation," *Nucleic Acids Research*, 27:1214-18, 1999.
Yoo et al., "Molecular cloning and nucleotide sequence of full-length of cDNA coding for porcine gastrin," *Proc. Natl. Acad. Sci. USA*, 79:1049-1053, 1982.
Zheleznaya et al., "PCR fragmentation of DNA," *Biochemistry*, 64:373-78, 1999.
Zhou et al., "Universal TA cloning," *Curr. Issues Mol. Biol.*, 2:1-7, 2000.

\* cited by examiner

PCR amplification using locus-specific primer
$P_1$ and universal primer U

Hemi-nested PCR amplification using second
locus-specific primer $P_2$ and universal primer U Cycle-sequencing using primer $P_2$ Sequencing by walking within the PCR-amplified DNA
using sequencing primers $S_1$, $S_2$, and $S_3$.

```
SEQUENCE LISTING

<160> NUMBER OF SEQ ID NOS: 35

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
atgtggcgcg taaactattg a                                                 21

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ctggcgggag tgagtagcaa                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ttcaactggc gcagggctat                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tctgccagcg cccgtaacaa                                                   20

<210> SEQ ID NO 5
<211> LENGTH: 21
```

```
<212> TYPE: DNA
<213> ORGANISM: Artificial Sequence
<220> FEATURE:
<223> OTHER INFORMATION: Synthetic primer

<400> SEQUENCE: 5
ccagcgcatt ctgactaaac c                                              21

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tcgcccatct tctcacgtag                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
ggtagccgtt gagtcaccct c                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gccgcaatca atacgacctg t                                              21

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
agaaaagctc ctgaggtgta gac                                            23

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
ctcatcttgg gcctgtgtta tct                                            23

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
```

```
ctgggccagc aagacttgac aac                                              23

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
gatcgagacc atcctggcta acgg                                             24

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
tgggcccacc tcttaccgat ttct                                             24

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
agctgcccaa ctgtagaaac tac                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
tagtgtgccc agtggttata ttg                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
gccgtccgat gagatcactg tag                                              23

<210> SEQ ID NO 17
<211> LENGTH: 23
<212> TYPE: DNA
<213> ORGANISM: Artificial Sequence
<220> FEATURE:
<223> OTHER INFORMATION: Synthetic primer

<400> SEQUENCE: 17
tctcaagtgg tccgctatta ttc                                              23

<210> SEQ ID NO 18
<211> LENGTH: 23
<212> TYPE: DNA
<213> ORGANISM: Artificial Sequence
```

```
<220> FEATURE:
<223> OTHER INFORMATION: Synthetic primer

<400> SEQUENCE: 18
gcccgcgcaa gccatccata gag                                              23

<210> SEQ ID NO 19
<211> LENGTH: 23
<212> TYPE: DNA
<213> ORGANISM: Artificial Sequence
<220> FEATURE:
<223> OTHER INFORMATION: Synthetic primer

<400> SEQUENCE: 19
accgaatcct cctgccgcaa agt                                              23

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
ctaaaagtcc ataacgggat gac                                              23

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
tgacacaacg gctacgattt aat                                              23

<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
gccgccggat tcagctaaat tgt                                              23

<210> SEQ ID NO 23
<211> LENGTH: 23
<212> TYPE: DNA
<213> ORGANISM: Artificial Sequence
<220> FEATURE:
<223> OTHER INFORMATION: Synthetic primer

<400> SEQUENCE: 23
cacgaccggg tcacgctgca ctg                                              23

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
ggccgggacc gttgaactag aac                                              23
```

<210> SEQ ID NO 25
<211> LENGTH: 23
<212> TYPE: DNA
<213> ORGANISM: Artificial Sequence
<220> FEATURE:
<223> OTHER INFORMATION: Synthetic primer

<400> SEQUENCE: 25
tttggccatg agtcgtgact tag                                              23

<210> SEQ ID NO 26
<211> LENGTH: 23
<212> TYPE: DNA
<213> ORGANISM: Artificial Sequence
<220> FEATURE:
<223> OTHER INFORMATION: Synthetic primer

<400> SEQUENCE: 26
tggccatgag tcgtgactta gtt                                              23

<210> SEQ ID NO 27
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
gaccggttct cctagcttgt t                                                21

<210> SEQ ID NO 28
<211> LENGTH: 23
<212> TYPE: DNA
<213> ORGANISM: Artificial Sequence
<220> FEATURE:
<223> OTHER INFORMATION: Synthetic primer

<400> SEQUENCE: 28
ccggttctcc tagcttgttc tac                                              23

<210> SEQ ID NO 29
<211> LENGTH: 29
<212> TYPE: DNA
<213> ORGANISM: Artificial Sequence
<220> FEATURE:
<223> OTHER INFORMATION: Synthetic primer

<400> SEQUENCE: 29
tctccttcct cctttctcgc ttctctcct                                        29

<210> SEQ ID NO 30
<211> LENGTH: 29
<212> TYPE: DNA
<213> ORGANISM: Artificial Sequence
<220> FEATURE:
<223> OTHER INFORMATION: Synthetic primer

<400> SEQUENCE: 30
tctccttcct cctttctcac ttctctcct                                        29

<210> SEQ ID NO 31
<211> LENGTH: 29
<212> TYPE: DNA
<213> ORGANISM: Artificial Sequence
<220> FEATURE:
<223> OTHER INFORMATION: Synthetic primer

```
<400> SEQUENCE: 31
tctccttcct cctttctcgc ttctctcct                                              29

<210> SEQ ID NO 32
<211> LENGTH: 11
<212> TYPE: DNA
<213> ORGANISM: Artificial Sequence
<220> FEATURE:
<223> OTHER INFORMATION: Synthetic primer

<400> SEQUENCE: 32
tctccttcct c                                                                 11

<210> SEQ ID NO 33
<211> LENGTH: 11
<212> TYPE: DNA
<213> ORGANISM: Artificial Sequence
<220> FEATURE:
<223> OTHER INFORMATION: Synthetic primer

<400> SEQUENCE: 33
tctccttcct c                                                                 11

<210> SEQ ID NO 34
<211> LENGTH: 10
<212> TYPE: DNA
<213> ORGANISM: Artificial Sequence
<220> FEATURE:
<223> OTHER INFORMATION: Synthetic primer

<400> SEQUENCE: 34
tctccttcct                                                                   10

<210> SEQ ID NO 35
<211> LENGTH: 11
<212> TYPE: DNA
<213> ORGANISM: Artificial Sequence
<220> FEATURE:
<223> OTHER INFORMATION: Synthetic primer

<400> SEQUENCE: 35
tctccttcct c                                                                 11
```

DNA AMPLIFICATION AND SEQUENCING USING DNA MOLECULES GENERATED BY RANDOM FRAGMENTATION

This application is a continuation of U.S. patent application Ser. No. 10/293,048 filed Nov. 13, 2002, which claims priority to U.S. Provisional Patent Application Ser. No. 60/338,224, filed Nov. 13, 2001. The entire text of the above-referenced disclosure is specifically incorporated herein by reference without disclaimer.

FIELD OF THE INVENTION

The present invention is directed to the fields of genomics, molecular biology, and sequencing. Specifically, the present invention regards methods of preparing DNA molecules, preparing DNA templates for sequencing, and sequencing from randomly fragmented DNA molecules.

BACKGROUND OF THE INVENTION

DNA sequencing is the most important analytical tool for understanding the genetic basis of living systems. The process involves determining the positions of each of the four major nucleotide bases, adenine (A), cytosine (C), guanine (G), and thymine (T) along the DNA molecule(s) of an organism. Short sequences of DNA are usually determined by creating a nested set of DNA fragments that begin at a unique site and terminate at a plurality of positions comprised of a specific base. The fragments terminated at each of the four natural nucleic acid bases (A, T, G and C) are then separated according to molecular size in order to determine the positions of each of the four bases relative to the unique site. The pattern of fragment lengths caused by strands that terminate at a specific base is called a "sequencing ladder." The interpretation of base positions as the result of one experiment on a DNA molecule is called a "read." There are different methods of creating and separating the nested sets of terminated DNA molecules (Adams et al., 1994; Primrose, 1998; Cantor and Smith, 1999).

Because the amount of any specific DNA molecule that can be isolated from even a large number of cells is usually very small, the only practical methods to prepare enough DNA molecules for most applications, including sequencing, involve amplification of specific DNA molecules in vivo or in vitro. There are basically six general methods important for manipulating DNA for analysis: 1) in vivo cloning of unique fragments of DNA; 2) in vitro amplification of unique fragments of DNA; 3) in vivo cloning of libraries (mixtures) of DNA fragments; 4) in vitro preparation of random libraries of DNA fragments; 5) in vivo cloning of ordered libraries of DNA; and 6) in vitro preparation of ordered libraries of DNA. The beneficial effect of amplifying mixtures of DNA is that it facilitates analysis of large pieces of DNA (e.g., chromosomes) by creating libraries of molecules that are small enough to be analyzed by existing techniques. For example the largest molecule that can be subjected to DNA sequencing methods is less than 2000 bases long, which is many orders of magnitude shorter than single chromosomes of organisms. Although short molecules can be analyzed, considerable effort is required to assemble the information from the analysis of the short molecules into a description of the larger piece of DNA.

1. In Vivo Cloning of Unique DNA

Unique-sequence source DNA molecules can be amplified by separating them from other molecules (e.g., by electrophoresis), ligating them into an autonomously replicating genetic element (e.g., a bacterial plasmid), transfecting a host cell with the recombinant genetic element, and growing a clone of a single transfected host cell to produce many copies of the genetic element having the insert with the same unique sequence as the source DNA (Sambrook, et al., 1989).

2. In Vitro Amplification of Unique DNA

There are many methods designed to amplify DNA in vitro. Usually these methods are used to prepare unique DNA molecules from a complex mixture, e.g., genomic DNA or an artificial chromosome. Alternatively, a restricted set of molecules can be prepared as a library that represents a subset of sequences in the complex mixture. These amplification methods include PCR™, rolling circle amplification, and strand displacement (Walker, et al. 1996a; Walker, et al. 1996b; U.S. Pat. No. 5,648,213; U.S. Pat. No. 6,124,120).

The polymerase chain reaction (PCR™) can be used to amplify specific regions of DNA between two known sequences (U.S. Pat. No. 4,683,195, U.S. Pat. No. 4,683,202; Frohman et al., 1995). PCR™ involves the repetition of a cycle consisting of denaturation of the source (template) DNA, hybridization of two oligonucleotide primers to known sequences flanking the region to the amplified, primer extension using a DNA polymerase to synthesize strands complementary to the DNA region located between the two primer sites. Because the products of one cycle of amplification serve as source DNA for succeeding cycles, the amplification is exponential. PCR™ can synthesize large numbers of specific molecules quickly and inexpensively.

The major disadvantages of the PCR™ method to amplify DNA are that 1) information about two flanking sequences must be known in order to specify the sequences of the primers; 2) synthesis of primers is expensive; 3) the level of amplification achieved depends strongly on the primer sequences, source DNA sequence, and the molecular weight of the amplified DNA; and 4) the length of amplified DNA is usually limited to less than 5 kb, although "long-distance" PCR™ (Cheng, 1994) allows molecules as long as 20 kb to be amplified.

"One-sided PCR™" techniques are able to amplify unknown DNA adjacent to one known sequence. These techniques can be divided into 4 categories: a) ligation-mediated PCR™, facilitated by addition of a universal adaptor sequence to a terminus usually created by digestion with a restriction endonuclease; b) universal primer-mediated PCR™, facilitated by a primer extension reaction initiated at arbitrary sites c) terminal transferase-mediated PCR™, facilitated by addition of a homonucleotide "tail" to the 3' end of DNA fragments; and d) inverse PCR™, facilitated by circularization of the template molecules. These techniques can be used to amplify successive regions along a large DNA template in a process sometimes called "chromosome walking" (Hui et al., 1998).

Ligation-mediated PCR™ is practiced in many forms. Rosenthal et al. (1990) outlined the basic process of amplifying an unknown region of DNA immediately adjacent to a known sequence located near the end of a restriction fragment. Reiley et al. (1990) used primers that were not exactly complementary with the adaptors in order to suppress amplification of molecules that did not have a specific priming site. Jones (1993) and Siebert (1995; U.S. Pat. No. 5,565,340) used long universal primers that formed intrastrand "panhandle" structures that suppressed PCR™ of molecules having two universal adaptors. Arnold (1994) used "vectorette" primers having unpaired central regions to increase the specificity of one-sided PCR™. Macrae and Brenner (1994) amplified short inserts from a Fugu genomic clone library using nested primers from a specific sequence and from vector sequences. Lin et al. (1995) ligated an adaptor to restriction fragment ends that had an overhanging 5' end and employed hot-start PCR™ with a single universal anchor primer and nested specific-site primers to specifically amplify human sequences. Liao et al. (1997) used two specific site primers and 2 universal adaptors, one of which had a blocked 3' end to reduce non-specific background, to amplify zebrafish promotors. Devon et al. (1995) used "splinkerette-vectorette" adaptors with special secondary structure in order to decrease non-specific amplification of molecules with two universal sequences during ligation-mediated PCR™. Padegimas and Reichert (1998) used phosphorothioate-blocked oligonucleotides and exoIII digestion to remove the unligated and partially ligated molecules from the reactions before performing PCR™, in order to increase the specificity of amplification of maize sequences. Zhang and Gun (2000) used ligation-mediated hot-start PCR™ of restriction fragments using nested primers in order to amplify up to 6 kb of a fungal genome. The large amplicons were subsequently directly sequenced using primer extension.

To increase the specificity of ligation-mediated PCR™ products, many methods have been used to "index" the amplification process by selection for specific sequences adjacent to one or both termini (e.g., Smith, 1992; Unrau, 1994; Guilfoyle, 1997; U.S. Pat. No. 5,508,169).

One-sided PCR™ can also be achieved by direct amplification using a combination of unique and non-unique primers. Liu and Whittier (1995) developed an efficient PCR strategy, thermal asymmetric interlaced (TAIL)-PCR, that utilizes nested sequence-specific primers together with a shorter arbitrary degenerate primer so that the relative amplification efficiencies of specific and non-specific products can be thermally controlled. Harrison et al. (1997) performed one-sided PCR™ using a degenerate oligonucleotide primer that was complementary to an unknown sequence and three nested primers complementary to a known sequence in order to sequence transgenes in mouse cells. U.S. Pat. No. 5,994,058 specifies using a unique PCR™ primer and a second, partially degenerate PCR™ primer to achieve one-sided PCR™. Weber et al. (1998) used direct PCR™ of genomic DNA, with nested primers from a known sequence and 1-4 primers complementary to frequent restriction sites. This technique does not require restriction digestion and ligation of adaptors to the ends of restriction fragments, Terminal transferase can also be used in one-sided PCR™. Cormack and Somssich (1997) were able to amplify the termini of genomic DNA fragments using a method called RAGE (rapid amplification of genome ends) by a) restricting the genome with one or more restriction enzymes; b) denaturing the restricted DNA; c) providing a 3' polythymidine tail using terminal transferase; and d) performing two rounds of PCR™ using nested primers complementary to a known sequence as well as the adaptor. Rudi et al. (1999) used terminal transferase to achieve chromosome walking in bacteria using a method of one-sided PCR™ that is independent of restriction digestion by a) denaturation of the template DNA; b) linear amplification using a primer complementary to a known sequence; c) addition of a poly C "tail" to the 3' end of the single-stranded products of linear amplification using a reaction catalyzed by terminal transferase; and d) PCR™ amplification of the products using a second primer within the known sequence and a poly-G primer complementary to the poly-C tail in the unknown region. The products amplified by Rudi (1999) have a very broad size distribution, probably caused by a broad distribution of lengths of the linearly-amplified DNA molecules.

RNA polymerase can also be used to achieve one-sided amplification of DNA. U.S. Pat. No. 6,027,913 shows how one-sided PCR™ can be combined with transcription with RNA polymerase to amplify and sequence regions of DNA with only one known sequence.

Inverse PCR™ (Ochman et al., 1988) is another method to amplify DNA based on knowledge of a single DNA sequence. The template for inverse PCR™ is a circular molecule of DNA created by a complete restriction digestion, which contains a small region of known sequence as well as adjacent regions of unknown sequence. The oligonucleotide primers are oriented such that during PCR™ they give rise to primer extension products that extend way from the known sequence. This "inside-out" PCR™ results in linear DNA products with known sequences at the termini.

The disadvantages of all "one-sided PCR™" methods is that a) the length of the products are restricted by the limitation of PCR™ (normally about 2 kb, but with special reagents up to 50 kb); b) whenever the products are single DNA molecules longer than 1 kb they are too long to directly sequence; c) in ligation-mediated PCR™ the amplicon lengths are very unpredictable due to random distances between the universal priming site and the specific priming site(s), resulting in some products that are sometimes too short to walk significant distance, some which are preferentially amplified due to small size, and some that are too long to amplify and analyze; and d) in methods that use terminal transferase to add a polynucleotide tail to the end of a primer extension product, there is great heterogeneity in the length of the amplicons due to sequence-dependent differences in the rate of primer extension.

Strand displacement amplification (Walker, et al. 1996a; Walker, et al. 1996b; U.S. Pat. No. 5,648,213; U.S. Pat. No. 6,124,120) is a method to amplify one or more termini of DNA fragments using an isothermal strand displacement reaction. The method is initiated at a nick near the terminus of a double-stranded DNA molecule, usually generated by a restriction enzyme, followed by a polymerization reaction by a DNA polymerase that is able to displace the strand complementary to the template strand. Linear amplification of the complementary strand is achieved by reusing the template multiple times by nicking each product strand as it is synthesized. The products are strands with 5' ends at a unique site and 3' ends that are various distances from the 5' ends. The extent of the strand displacement reaction is not controlled and therefore the lengths of the product strands are not uniform. The polymerase used for strand displacement amplification does not have a 5' exonuclease activity.

Rolling circle amplification (U.S. Pat. No. 5,648,245) is a method to increase the effectiveness of the strand displacement reaction by using a circular template. The polymerase, which does not have a 5' exonuclease activity, makes multiple copies of the information on the circular template as it makes multiple continuous cycles around the template. The length of the product is very large—typically too large to be directly sequenced. Additional amplification is achieved if a second strand displacement primer is added to the reaction to used the first strand displacement product as a template.

3. In Vivo Cloning of DNA of Random Libraries

Libraries are collections of small DNA molecules that represent all parts of a larger DNA molecule or collection of DNA molecules (Primrose, 1998; Cantor and Smith, 1999). Libraries can be used for analytical and preparative purposes. Genomic clone libraries are the collection of bacterial clones containing fragments of genomic DNA. cDNA clone libraries are collections of clones derived from mRNA molecules.

Cloning of non-specific DNA is commonly used to separate and amplify DNA for analysis. DNA from an entire genome, one chromosome, a virus, or a bacterial plasmid is fragmented by a suitable method (e.g., hydrodynamic shearing or digestion with restriction enzymes), ligated into a special region of a bacterial plasmid or other cloning vector, transfected into competent cells, amplified as a part of a plasmid or chromosome during proliferation of the cells, and harvested from the cell culture. Critical to the specificity of this technique is the fact that the mixture of cells carrying different DNA inserts can be diluted and aliquoted such that some of the aliquots, whether on a surface or in a volume of solution, contain a single transfected cell containing a unique fragment of DNA. Proliferation of this single cell (in vivo cloning) amplifies this unique fragment of DNA so that it can be analyzed. This "shotgun" cloning method is used very frequently, because: 1) it is inexpensive; 2) it produces very pure sequences that are usually faithful copies of the source DNA; 3) it can be used in conjunction with clone screening techniques to create an unlimited amount of specific-sequence DNA; 4) it allows simultaneous amplification of many different sequences; 5) it can be used to amplify DNA as large as 1,000,000 bp long; and 6) the cloned DNA can be directly used for sequencing and other purposes.

Cloning is inexpensive, because many pieces of DNA can be simultaneously transfected into host cells. The general term for this process of mixing a number of different entities (e.g., electronic signals or molecules) is "multiplexing," and is a common strategy for increasing the number of signals or molecules that can be processed simultaneously and subsequently separated to recover the information about the individual signals or molecules. In the case of conventional cloning, the recovery process involves diluting the bacterial culture such that an aliquot contains a single bacterium carrying a single plasmid, allowing the bacterium to multiply to create many copies of the original plasmid, and isolating the cloned DNA for further analysis.

The principle of multiplexing different molecules in the same transfection experiment is critical to the economy of the cloning method. However, after the transfection each clone must be grown separately and the DNA isolated separately for analysis. These steps, especially the DNA isolation step, are costly and time consuming. Several attempts have been made to multiplex steps after cloning, whereby hundreds of clones can be combined during the steps of DNA isolation and analysis and the characteristics of the individual DNA molecules recovered later. In one version of multiplex cloning the DNA fragments are separated into a number of pools (e.g., one hundred pools). Each pool is ligated into a different vector, possessing a nucleic acid tag with a unique sequence, and transfected into the bacteria. One clone from each transfection pool is combined with one clone from each of the other transfection pools in order to create a mixture of bacteria having a mixture of inserted sequences, where each specific inserted sequence is tagged with a unique vector sequence, and therefore can be identified by hybridization to the nucleic acid tag. This mixture of cloned DNA molecules can be subsequently separated and subjected to any enzymatic, chemical, or physical processes for analysis such as treatment with polymerase or size separation by electrophoresis. The information about individual molecules can be recovered by detection of the nucleic acid tag sequences by hybridization, PCR™ amplification, or DNA sequencing. Church has shown methods and compositions to use multiplex cloning to sequence DNA molecules by pooling clones tagged with different labels during the steps of DNA isolation, sequencing reactions, and electrophoretic separation of denatured DNA strands (U.S. Pat. Nos. 4,942,124 and 5,149,625). The tags are added to the DNA as parts of the vector DNA sequences. The tags used can be detected using oligonucleotides labeled with radioactivity, fluorescent groups, or volatile mass labels (Cantor and Smith, 1999; U.S. Pat. Nos. 4,942,124; 5,149,625; and 5,112,736; Richterich and Church, (1993)). A later patent was directed to a technique whereby the tag sequences are ligated to the DNA fragments before cloning using a universal vector (U.S. Pat. No. 5,714,318). Another patent specifies a method whereby the tag sequences added before transfection are amplified using PCR™ after electrophoretic separation of the denatured DNA (PCT WO 98/15644).

4. In Vitro Preparation of DNA as Random Libraries

DNA libraries can be formed in vitro and subjected to various selection steps to recover information about specific sequences. In vitro libraries are rarely used in genomics, because the methods that exist for creating such libraries do not offer advantages over cloned libraries. In particular, the methods used to amplify the in vitro libraries are not able to amplify all the DNA in an unbiased manner, because of the size and sequence dependence of amplification efficiency. PCT WO 00/18960 describes how different methods of DNA amplification can be used to create a library of DNA molecules representing a specific subset of the sequences within the genome for purposes of detecting genetic polymorphisms. "Random-prime PCR™" (U.S. Pat. No. 5,043,272; U.S. Pat. No. 5,487,985) "random-prime strand displacement" (U.S. Pat. No. 6,124,120) and "AFLP" (U.S. Pat. No. 6,045,994) are three examples of methods to create libraries that represent subsets of complex mixtures of DNA molecules.

Single-molecule PCR™ can be used to amplify individual randomly-fragmented DNA molecules (Lukyanov et al., 1996). In one method, the source DNA is first fragmented into molecules usually less than 10,000 bp in size, ligated to adaptor oligonucleotides, and extensively diluted and aliquoted into separate fractions such that the fractions often contain only a single molecule. PCR™ amplification of a fraction containing a single molecule creates a very large number of molecules identical to one of the original fragments. If the molecules are randomly fragmented, the amplified fractions represent DNA from random positions within the source DNA.

WO0015779A2 describes how a specific sequence can be amplified from a library of circular molecules with random genomic inserts using rolling circle amplification.

5. Direct In Vivo Cloning of Ordered Libraries of DNA

Directed cloning is a procedure to clone DNA from different parts of a larger piece of DNA, usually for the purpose of sequencing DNA from a different positions along the source DNA. Methods to clone DNA with "nested deletions" have been used to make "ordered libraries" of clones that have DNA starting at different regions along a long piece of source DNA. In one version, one end of the source DNA is digested with one or more exonuclease activities to delete part of the sequence (McCombie et al., 1991; U.S. Pat. No. 4,843,003). By controlling the extent of exonuclease digestion, the average amount of the deletion can be controlled. The DNA molecules are subsequently separated based on size and cloned. By cloning molecules with different molecular weights, many copies of identical DNA plasmids are produced that have inserts ending at controlled positions within the source DNA. Transposon insertion (Berg et al., 1994) is also used to clone different regions of source DNA by facilitating priming or cleavage at random positions in the plasmids. The size separation and recloning steps make both of these methods labor intensive and slow. They are generally limited to covering regions less than 10 kb in size and cannot be used directly on genomic DNA but rather cloned DNA molecules. No in vivo methods are known to directly create ordered libraries of genomic DNA.

6. Direct In Vitro Preparation of Ordered Libraries of DNA

Ordered libraries have not been frequently created in vitro. Hagiwara (1996) used one-sided PCR™ to create an ordered library of PCR™ products that was used to sequence about 14 kb of a cosmid. The cosmids were first digested with multiple restriction enzymes, followed by ligation of vectorette adaptors to the products, PCR™ amplification of the products using primers complementary to a unique sequence in the cosmid and to the adaptor, size separation of the amplified DNA to establish the order of the restriction sites, and sequencing of the ordered PCR™ products. Because the non-uniform spacing of the restriction sites, 2 kb of the 16 kb region were not sequenced. This method required substantial effort to produce and order the PCR™ products for the job of sequencing cloned DNA. No in vitro methods are known to directly create ordered genomic libraries of DNA.

7. Preparation of DNA

In methods known and used in the art, molecules for sequencing are prepared (see, for example, Sambrook et al. (1989) or Ausubel et al. (1994)).

Furthermore, Japan Patent No. JP8173164A2 describes a method of preparing DNA by sorting-out PCR™ amplification in the absence of cloning, fragmenting a double-stranded DNA, ligating a known-sequence oligomer to the cut end, and amplifying the resultant DNA fragment with a primer having the sorting-out sequence complementary to the oligomer. The sorting-out sequences consist of a fluorescent label and one to four bases at 5' and 3' termini to amplify the number of copies of the DNA fragment.

U.S. Pat. No. 6,107,023 describes a method of isolating duplex DNA fragments which are unique to one of two fragment mixtures, i.e., fragments which are present in a mixture of duplex DNA fragments derived from a positive source, but absent from a fragment mixture derived from a negative source. In practicing the method, double-strand linkers are attached to each of the fragment mixtures, and the number of fragments in each mixture is amplified by successively repeating the steps of (i) denaturing the fragments to produce single fragment strands; (ii) hybridizing the single strands with a primer whose sequence is complementary to the linker region at one end of each strand, to form strand/primer complexes; and (iii) converting the strand/primer complexes to double-strand fragments in the presence of polymerase and deoxynucleotides. After the desired fragment amplification is achieved, the two fragment mixtures are denatured, then hybridized under conditions in which the linker regions associated with the two mixtures do not hybridize. DNA species which are unique to the positive-source mixture, i.e., which are not hybridized with DNA fragment strands from the negative-source mixture, are then selectively isolated.

U.S. Pat. No. 6,114,149 regards a method of amplifying a mixture of different-sequence DNA fragments that may be formed from RNA transcription, or derived from genomic single- or double-stranded DNA fragments. The fragments are treated with terminal deoxynucleotide transferase and a selected deoxynucleotide, to form a homopolymer tail at the 3' end of the anti-sense strands, and the sense strands are provided with a common 3'-end sequence. The fragments are mixed with a homopolymer primer that is homologous to the homopolymer tail of the anti-sense strands, and a defined-sequence primer which is homologous to the sense-strand common 3'-end sequence, with repeated cycles of fragment denaturation, annealing, and polymerization, to amplify the fragments. In one embodiment, the defined-sequence and homopolymer primers are the same, i.e., only one primer is used. The primers may contain selected restriction-site sequences, to provide directional restriction sites at the ends of the amplified fragments.

Thus, the present invention provides a new way of preparing DNA templates for more efficient sequencing of difficult DNA molecules, higher sequence quality, and longer reads.

SUMMARY OF THE INVENTION

The present invention is directed to preparing DNA molecules for a variety of purposes, including sequencing. In specific embodiments, preparation of the molecules comprises random fragmentation of a parent DNA molecule to produce the fragments, attachment of at least one primer to the fragments, and amplification of at least a portion of the fragments.

In an object of the present invention, there is a method of preparing a DNA molecule, comprising obtaining a DNA molecule; randomly fragmenting the DNA molecule to produce DNA fragments; attaching a primer having substantially known sequence to at least one end of a plurality of the DNA fragments to produce primer-linked fragments; and amplifying a plurality of the primer-linked fragments. In a specific embodiment, the method further comprises concomitantly sequencing the plurality of primer-linked fragments. In further specific embodiments, the randomly fragmenting of the DNA molecule is by mechanical fragmentation, such as by hydrodynamic shearing, sonication, or nebulization, or chemical fragmentation, such as by acid catalytic hydrolysis, alkaline catalytic hydrolysis, hydrolysis by metal ions, hydroxyl radicals, irradiation, or heating. In specific embodiments, the heating is to a temperature of between about 40° C. and 120° C., between about 80° C. and 100° C., between about 90° C. and 100° C., between about 92° C. and 98° C., between about 93° C. and 97° C., or between about 94° C. and 96° C. In a preferred embodiment, the heating is to a temperature of about 95° C.

In a specific embodiment, the heating of the DNA molecule is in a solution having from 0 to about 100 mM concentration of a salt, having from about 0 to about 10 mM concentration of salt, having from about 0.1 to about 1 mM concentration of salt, or having from about 0.1 to about 0.5 mM concentration of salt. In a specific embodiment, the heating is in a solution of 10 mM Tris, pH 8.0; 1 mM EDTA or a solution of water.

In another embodiment, the random fragmenting of the DNA molecule is by enzymatic fragmentation, such as comprising digestion with DNAse I. In specific embodiments, the DNAse I digestion is in the presence of $Mg^{2+}$ ions, such as in a concentration of about 1 mM to about 10 mM. In another specific embodiment, the DNAse I digestion is in the presence of $Mn^{2+}$ ions, such as in a concentration of about 1 mM to about 10 mM.

In a specific embodiment of the present invention, the primer is attached to at least one 3' end of at least one DNA fragment. In another specific embodiment, attachment of a primer having substantially known sequence to at least one 3' end of at least one DNA fragment comprises generation of a homopolymer extension of said DNA fragment, such as is generated by terminal deoxynucleotidyltransferase. In a specific embodiment, the homopolymeric extension comprises a polyG tract.

In another specific embodiment, the attachment of a substantially known sequence to at least one 3' end of at least one DNA fragment comprises ligation of an adaptor molecule to at least one end of the DNA fragment. In a specific embodiment, the adaptor comprises at least one blunt end. In another specific embodiment, the adaptor comprises a single stranded region. In a further specific embodiment, the method further comprises generation of at least one blunt end of said DNA fragments, such as is generated by T4 DNA polymerase, Klenow, or a combination thereof.

In another object of the present invention, there is a method of preparing a library of DNA molecules, comprising obtaining a plurality of DNA molecules; randomly fragmenting at least one of the DNA molecules to produce DNA fragments; attaching a primer having a substantially known sequence to at least one end of a plurality of the DNA fragments to produce primer-linked fragments; and amplifying a plurality of the primer-linked fragments. In a specific embodiment, the method further comprises concomitantly sequencing the plurality of primer-linked fragments.

In an additional object of the present invention, there is a library generated by a method described herein.

In an additional object of the present invention, there is a method of generating a library of DNA templates, comprising obtaining a plurality of DNA molecules; randomly fragmenting the plurality of DNA molecules to produce DNA fragments; attaching a first primer having substantially known sequence to at least one end of a plurality of the DNA fragments to produce primer-linked fragments; and amplifying a plurality of the primer-linked fragments, wherein the amplification utilizes a second primer complementary to a known sequence in the DNA fragments; and a third primer complementary to the first primer. In a specific embodiment, the method further comprises the step of sequencing concomitantly said plurality of DNA fragments using a fourth primer complementary to said known sequence in the DNA fragments. In a specific embodiment, the fourth primer is said second primer.

In another object of the present invention, there is a method of sequencing a plurality of DNA fragments concomitantly, comprising obtaining a plurality of DNA molecules; randomly fragmenting the DNA molecules to generate a plurality of DNA fragments having overlapping sequences; attaching a first primer having a substantially known sequence to at least one end of the plurality of the DNA fragments to produce primer-linked fragments; and amplifying a plurality of the primer-linked fragments, wherein the amplification utilizes a second primer complementary to a known sequence in the DNA fragments; and a third primer complementary to the first primer; and sequencing said plurality of DNA fragments using a fourth primer complementary to said known sequence in the DNA fragments. In a specific embodiment, the fourth primer is the second primer.

In another object of the present invention, there is a method of sequencing a consecutive overlapping series of nucleic acid sequences, comprising the steps of obtaining a plurality of DNA molecules having overlapping sequences; concomitantly sequencing a first region in said plurality of DNA molecules using a primer complementary to a known sequence in said plurality of DNA molecules; and concomitantly sequencing a second region in said plurality of DNA molecules using a primer complementary to sequence determined from the sequencing of the first region, wherein the next consecutive sequencing of a region in the overlapping series of nucleic acid sequences is produced by initiating sequencing from the sequence obtained in a preceding overlapping sequencing product. In a specific embodiment, the obtaining step is further defined as randomly fragmenting at least one parent DNA molecule to generate a plurality of DNA fragments having overlapping sequences; attaching a first primer having a substantially known sequence to at least one end of the plurality of the DNA fragments to produce primer-linked fragments; and amplifying a plurality of the primer-linked fragments, wherein the amplification utilizes a second primer complementary to a known sequence in the DNA fragments; and a third primer complementary to the first primer.

In an additional object of the present invention, there is a method of sequencing a plurality of DNA molecules, comprising obtaining said plurality of DNA molecules by randomly fragmenting a parent DNA molecule; sequencing concomitantly said plurality of DNA molecules with a primer complementary to a known sequence in said plurality of molecules. In a specific embodiment, the method further comprises amplification of the plurality of DNA molecules. In an additional specific embodiment, the amplification is further defined as attaching a first primer having a substantially known sequence to at least one end of the plurality of the DNA fragments to produce primer-linked fragments; and amplifying a plurality of the primer-linked fragments, wherein the amplification utilizes a second primer complementary to a known sequence in the DNA fragments; and a third primer complementary to the first primer.

In a further object of the present invention, there is a method of preparing a DNA molecule having sequences which generate secondary structure in said molecule, comprising obtaining the DNA molecule having said sequences; randomly fragmenting the DNA molecule to produce a plurality of DNA fragments, wherein the plurality of DNA fragments comprises DNA fragments having part or all of the sequences which generate the secondary structure; attaching a primer having substantially known sequence to at least one end of a plurality of the DNA fragments to produce primer-linked fragments; and amplifying a plurality of the primer-linked fragments. In a specific embodiment, the method further comprises concomitantly sequencing the plurality of primer-linked fragments. In a specific embodiment, the plurality of DNA fragments further comprises DNA fragments having none of the sequences which generate the secondary structure. In another specific embodiment, the secondary structure is a hairpin, a G quartet, or a triple helix. In a further specific embodiment, the obtained DNA molecule comprises genomic DNA, BAC DNA, or plasmid DNA.

In another object of the present invention, there is a method of conditioning a 3' end of a DNA molecule, comprising exposing said 3' end to terminal deoxynucleotidyltransferase. In a specific embodiment, the terminal deoxynucleotidyltransferase is further defined as comprising 3' exonuclease activity. In another specific embodiment, the exposing step further comprises providing a guanine ribonucleotide or guanine deoxyribonucleotide.

In an additional object of the present invention, there is a method of providing 3' exonuclease activity to the end of a DNA molecule comprising the step of introducing terminal deoxynucleotidyltransferase to the end of said molecule. In a specific embodiment, the introducing step further comprises providing a guanine ribonucleotide or guanine deoxyribonucleotide.

In an additional object of the present invention, there is a method of preparing a probe, comprising obtaining at least one DNA molecule; randomly fragmenting the DNA molecule to produce DNA fragments; attaching a labeled primer having substantially known sequence to at least one end of a plurality of the DNA fragments to produce labeled primer-linked fragments; and amplifying a plurality of the primer-linked fragments. In a specific embodiment, the attaching step of a labeled primer comprises generation of a homopolymer extension of said DNA fragment, wherein said extension comprises the label. In a specific embodiment, the homopolymeric extension is generated by terminal deoxynucleotidyltransferase. In a further specific embodiment, the attaching step of a labeled primer comprises ligation of an adaptor molecule to at least one end of the DNA fragment, wherein the adaptor molecule comprises the label. In another specific embodiment, the label is a radionuclide, an affinity tag, a hapten, an enzyme, a chromophore, or a fluorophore. In another embodiment, there is a labeled probe generated from the present method. In an additional embodiment, there is a kit comprising a probe generated from the present method.

In another object of the present invention, there is a method of repairing a 3' end of at least one single stranded DNA molecule, comprising providing to said 3' end a terminal deoxynucleotidyltransferase. In a specific embodiment, the providing step further comprises providing a guanine ribonucleotide, guanine deoxyribonucleotide, or both.

In an additional object of the present invention, there is a kit for repairing a 3' end of at least one single stranded DNA molecule, wherein said kit comprises a terminal deoxynucleotidyltransferase.

In an additional object of the present invention, there is a method of detecting a damaged DNA molecule, comprising the step of providing to said damaged DNA molecule terminal deoxynucleotidyltransferase and a labeled guanine ribonucleotide, labeled guanine deoxyribonucleotide, or both. In a specific embodiment, the damaged DNA molecule comprises a nick or a double stranded break. In another specific embodiment, the providing step is further defined as providing repair to said damaged DNA molecule. In an additional specific embodiment, the label comprises a radionuclide, an affinity tag, a hapten, an enzyme, a chromophore, or a fluorophore. In a further specific embodiment, the damaged DNA is outside a cell. In a specific embodiment, the damaged DNA is the result of radiation, ultraviolet light, oxygen, a radical, a metal ion, a nuclease, or mechanical force. In a specific embodiment, the damaged DNA is in a cell. In another specific embodiment, cell is an apoptotic cell. In an additional specific embodiment, the damaged DNA is the result of radiation, heat, ultraviolet light, oxygen, radicals, nitric oxide, catecholamine, or a nuclease.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
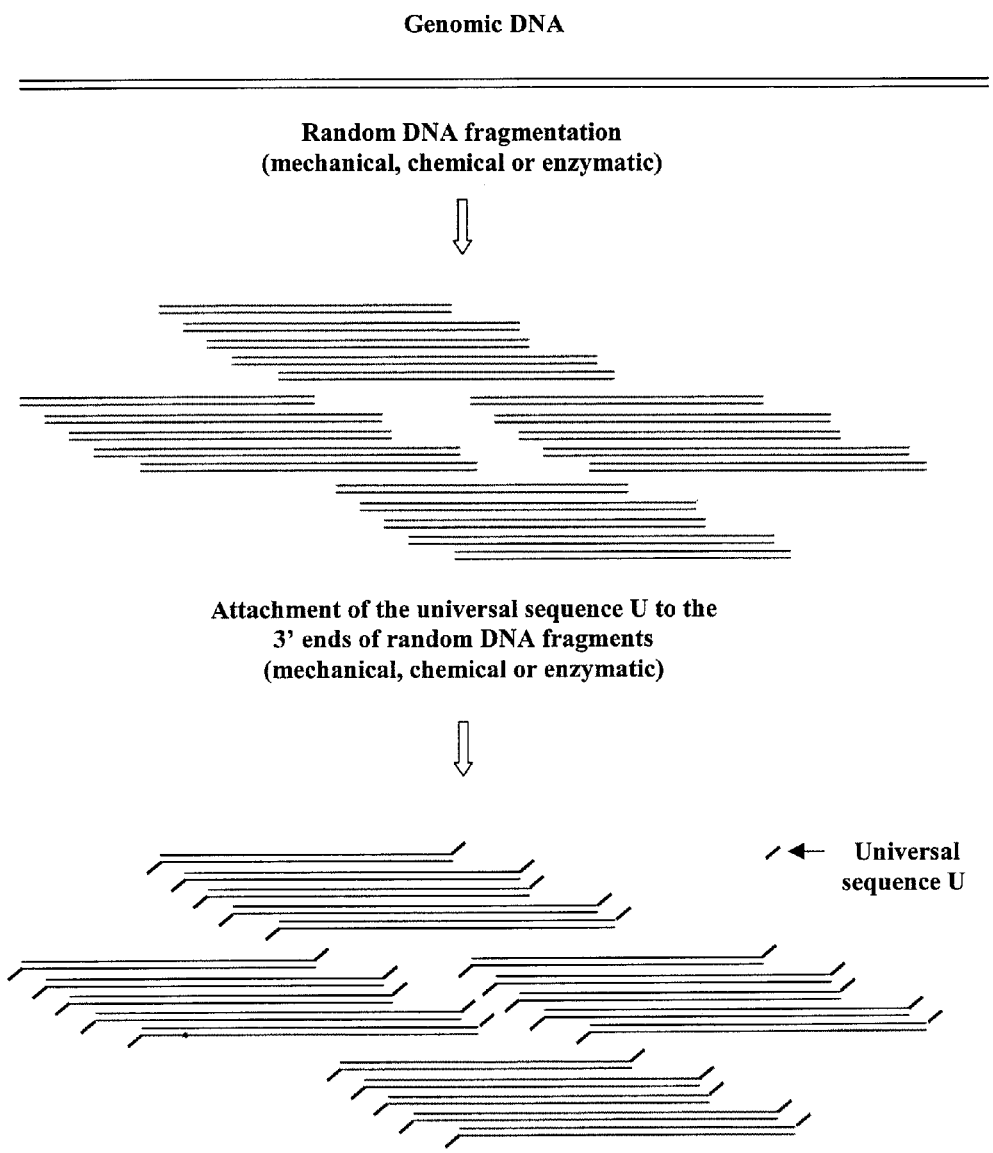
FIG. 1 demonstrates preparation of a TRF library produced by random fragmentation and 3' end tailing.

In keeping with long-standing patent law convention, the words "a" and "an" when used in the present specification in concert with the word comprising, including the claims, denote "one or more."

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS 1N MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

U.S. Pat. No. 6,197,557 is incorporated by reference herein in its entirety.

I. The Present Invention

The present invention is directed to methods to prepare a DNA molecule or a library of DNA molecules, or both. The preparation of the DNA molecule comprises random fragmentation of the molecule and amplification of at least one fragment of the molecule. Although the prepared molecule may be used for any purpose known in the art, in a specific embodiment it is used for sequencing of at least a portion of the molecule. The present invention is also directed to libraries of DNA molecules, particularly fragments of the molecules generated by random fragmentation of at least one parent DNA. In a specific embodiment, the library members are sequenced concomitantly.

The term "random fragmentation" as used herein refers to the fragmentation of a DNA molecule in a non-ordered fashion, such as irrespective of the sequence identity or position of the nucleotide comprising and/or surrounding the break.

In a specific embodiment, the fragments generated by random fragmentation are amplified prior to sequencing. A skilled artisan recognizes that the products of amplification of randomly generated DNA fragments, in some embodiments differing in length by only a nucleotide, produces a mixture of molecules of different lengths terminating at different positions. Such a mixture on a gel would present as a smear, suggesting an inability to be utilized as templates for sequencing with clarity. However, the present invention is directed to utilizing this mixture of fragments of different lengths that terminate at different positions as sequencing templates. Furthermore, in specific embodiments, the mixture of fragments are sequenced concomitantly.

In another specific embodiment, a series of overlapping sequences are generated by random fragmentation, the fragments are sequenced concomitantly in a particular region, and walking then occurs along the overlapping sequences by utilizing sequence determined in the preceding region.

A. Preparation of Randomly Fragmented DNA

A library is prepared in at least two steps: first, random fragmentation of DNA into 1-5 kb pieces and, second, attachment of universal adaptor sequence to the ends of DNA fragments, preferably the 3' ends (FIG. 1). These libraries are referred to as Tailed, Randomly Fragmented (TRF) DNA libraries.

Figure 2:
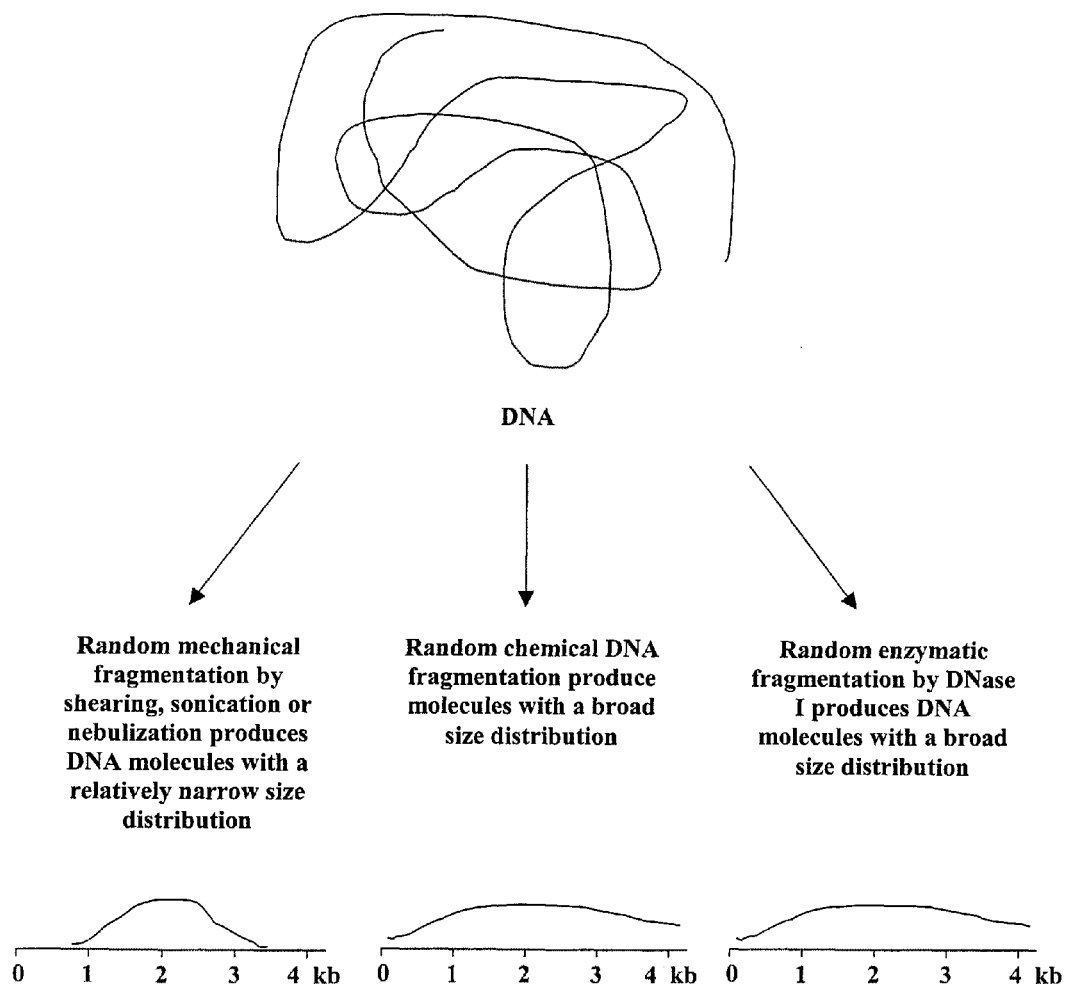
FIG. 2 illustrates methods for random DNA fragmentation.

Random fragmentation of DNA can be achieved by methods well-known in the art (FIG. 2). Several examples are illustrated in FIG. 2.

1. Mechanical Fragmentation

Mechanical fragmentation can occur by any method known in the art, including hydrodynamic shearing of DNA by passing it through the narrow capillary or orifice (Oefner et al., 1996; Thorstenson et al., 1998), sonicating the DNA, such as by ultrasound (Bankier, 1993), and/or nebulizing the DNA (Bodenteich et al., 1994). Mechanical fragmentation usually results in double strand breaks within the DNA molecule.

2. Chemical Fragmentation, Including Thermal Fragmentation

Chemical fragmentation of DNA can be achieved by any method known in the art, including acid or alkaline catalytic hydrolysis of DNA (Richards and Boyer, 1965), hydrolysis by metal ions and complexes (Komiyama and Sumaoka, 1998; Franklin, 2001; Branum et al., 2001), hydroxyl radicals (Tullius, 1991; Price and Tullius, 1992) or radiation treatment of DNA (Roots et al., 1989; Hayes et al., 1990). Chemical treatment could result in double or single strand breaks, or both.

In the present invention, a novel method is provided for introducing breaks into a DNA molecule—the thermal fragmentation of DNA. Thermal fragmentation is defined as generating double or single strand breaks, or both, in a DNA molecule when the molecule is in the presence of a temperature greater than room temperature, in some embodiments at least about 40° C. In alternative embodiments, the temperature is ambient temperature. In further specific embodiments, the temperature is between about 40° C. and 120° C., between about 80° C. and 100° C., between about 90° C. and 100° C., between about 92° C. and 98° C., between about 93° C. and 97° C., or between about 94° C. and 96° C. In some embodiments, the temperature is about 95° C. In some embodiments, the temperature is greater than 100° C. A skilled artisan recognizes that parameters other than temperature may affect the breakage, such as pH and/or salt concentration. In specific embodiments, the conditions of thermal fragmentation comprise neutral pH (pH 6.0-9.0) in low salt buffer (L-TE buffer) at 95° C. (about 80° C.-100° C. temperature range). The methods of the present invention produce DNA molecules that can, for example, be efficiently tailed at the 3' ends with the homopolymeric G-stretches using terminal transferase. In other embodiments, adaptors may be ligated to the fragment ends.

DNA can be efficiently fragmented at neutral pH by heat (Eigner et al., 1961). Due to instability of purine-glycosyl bonds, DNA incubation at high temperature results in release of purines from DNA, or depurination. Depurinated DNA, in turn, becomes susceptible to heat-induced hydrolysis at apurinic sites. Both processes occur at a very slow but physiologically significant rate (Greer and Zamenhov, 1962; Lindahl and Nyberg, 1972; Lindahl and Andersson, 1972). Probably because of its low rate in standard buffers, heat-induced DNA hydrolysis was never used in standard molecular biology procedures to fragment DNA.

Figure 21:
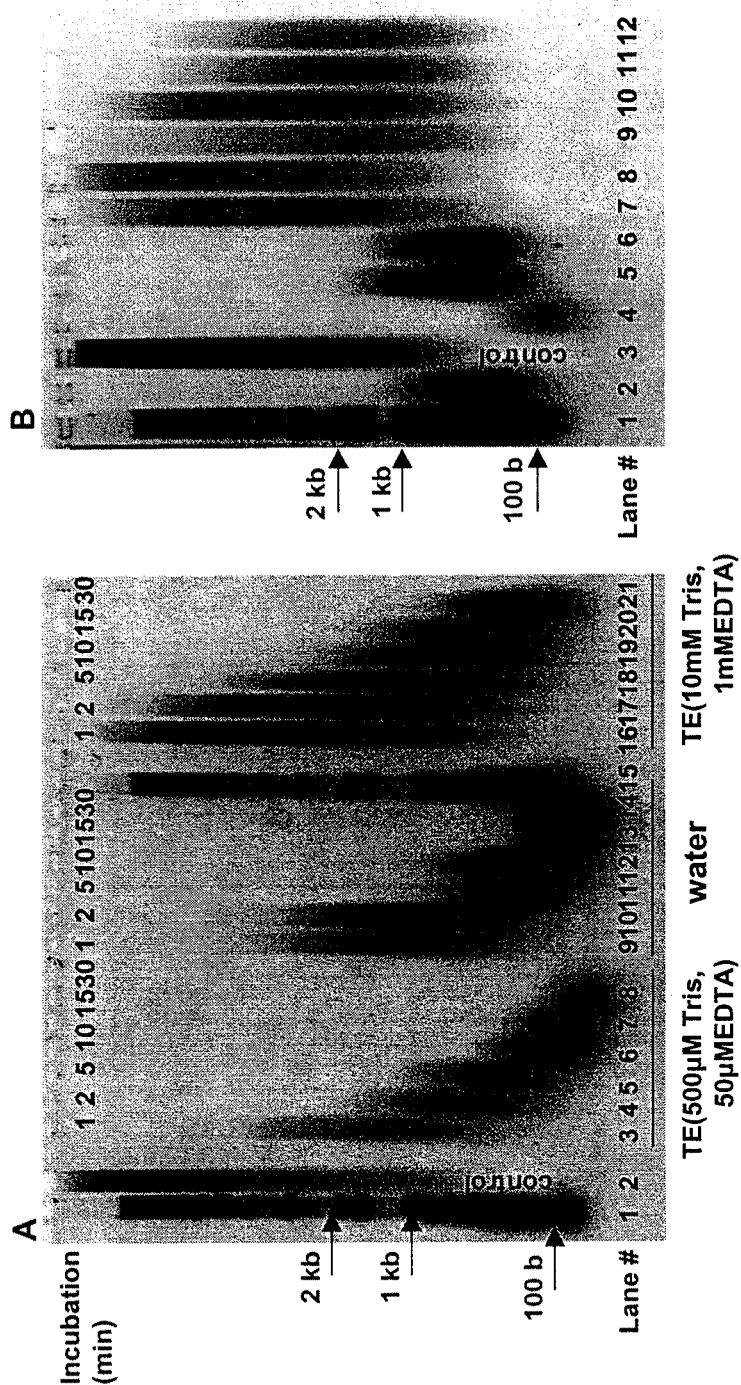
FIG. 21 shows kinetics of thermal fragmentation of E. coli DNA under different salt buffer conditions.
Figure 22:
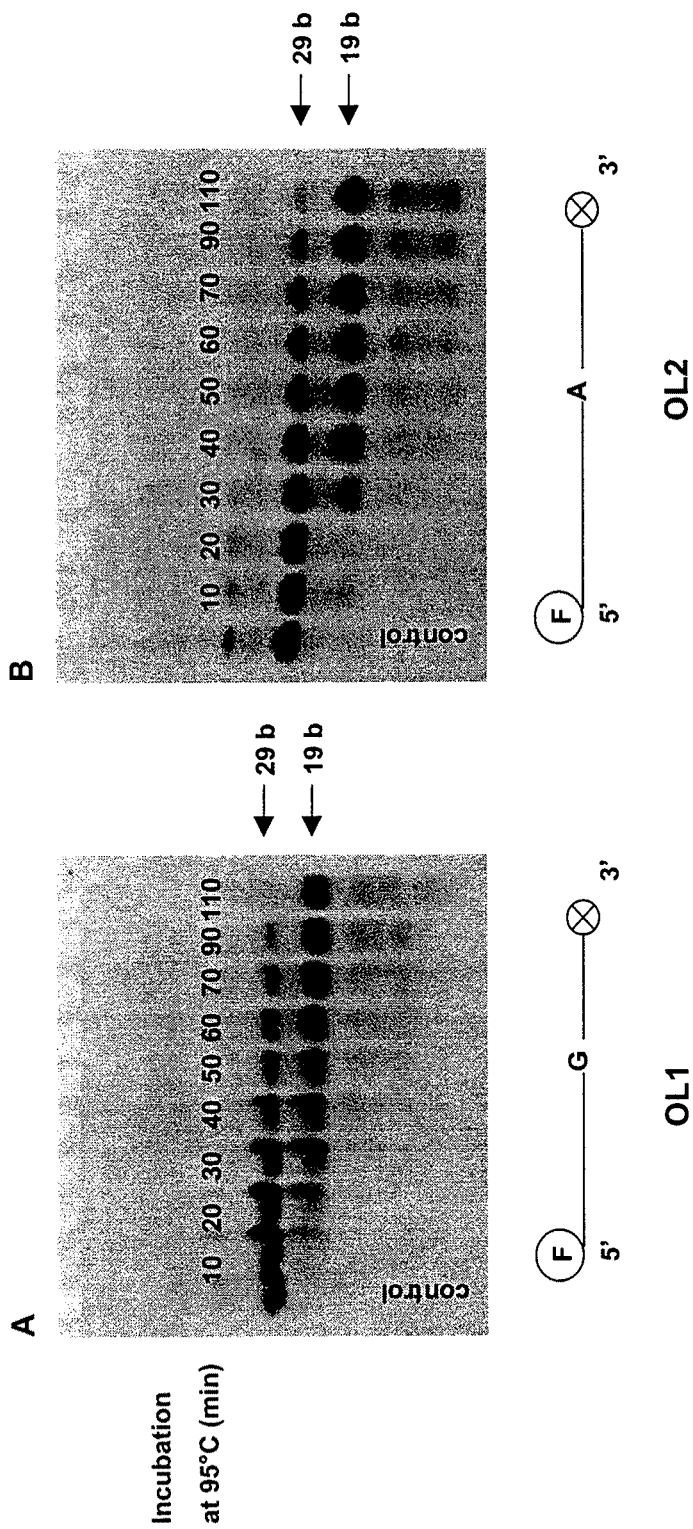
FIG. 22 illustrates a depurinization mechanism of thermal fragmentation on a model 5' fluorescein-labeled oligonucleotide with a single purine base.

Thus, in the present invention, a validated and optimized method is provided for introducing breaks into DNA molecules—the thermal fragmentation of DNA at neutral pH (pH 6.0-9.0) in low salt buffer (L-TE buffer) at 95° C. (about 80° C.-100° C. temperature range). The method produces DNA molecules, such as about 50-about 2,000 bases long, and the fragment length can be reproducibly controlled by time of heating and salt or buffer concentration, or both (FIG. 21, Example 11). The cleavage occurs mostly at purine sites and, in some cases, at pyrimidine bases (FIG. 22, Example 12). Thermal fragmentation produces DNA molecules that, at least, can be efficiently tailed at the 3' end with homopolymeric G-stretches using terminal transferase or that can be ligated with adaptors.

Thermally fragmented DNA can be used to prepare random DNA libraries or DNA probes.

3. Enzymatic Fragmentation

Enzymatic fragmentation of DNA may be utilized by standard methods in the art, such as by partial restriction digestion by Cvi JI endonuclease (Gingrich et al., 1996), or by DNAse I (Anderson, 1981; Ausubel et al., 1987). Fragmentation by DNAse I may occur in the presence of $Mg^{2+}$ ions (about 1-10 mM; predominantly single strand breaks) or in the presence of $Mn^{2+}$ ions (about 1-10 mM; predominantly double strand breaks).

Among these methods, the hydrodynamic shearing process produces DNA molecules with an appropriate and narrow size distribution (FIG. 2). For example, the commercially available device HydroShear (GeneMachines, Palo Alto, Calif.) can randomly fracture the DNA to within a two-fold size distribution with the average size of molecules ranging from 1.5 kb to 5 kb. The method does not introduce any additional modifications to the DNA, and the fragments can be directly used for 3' end tailing with the enzyme terminal deoxynucleotidyltransferase (TdT) or for ligation with blunt-end adaptors.

B. Sequence Attachment to the Ends of DNA Fragments

Figure 3:
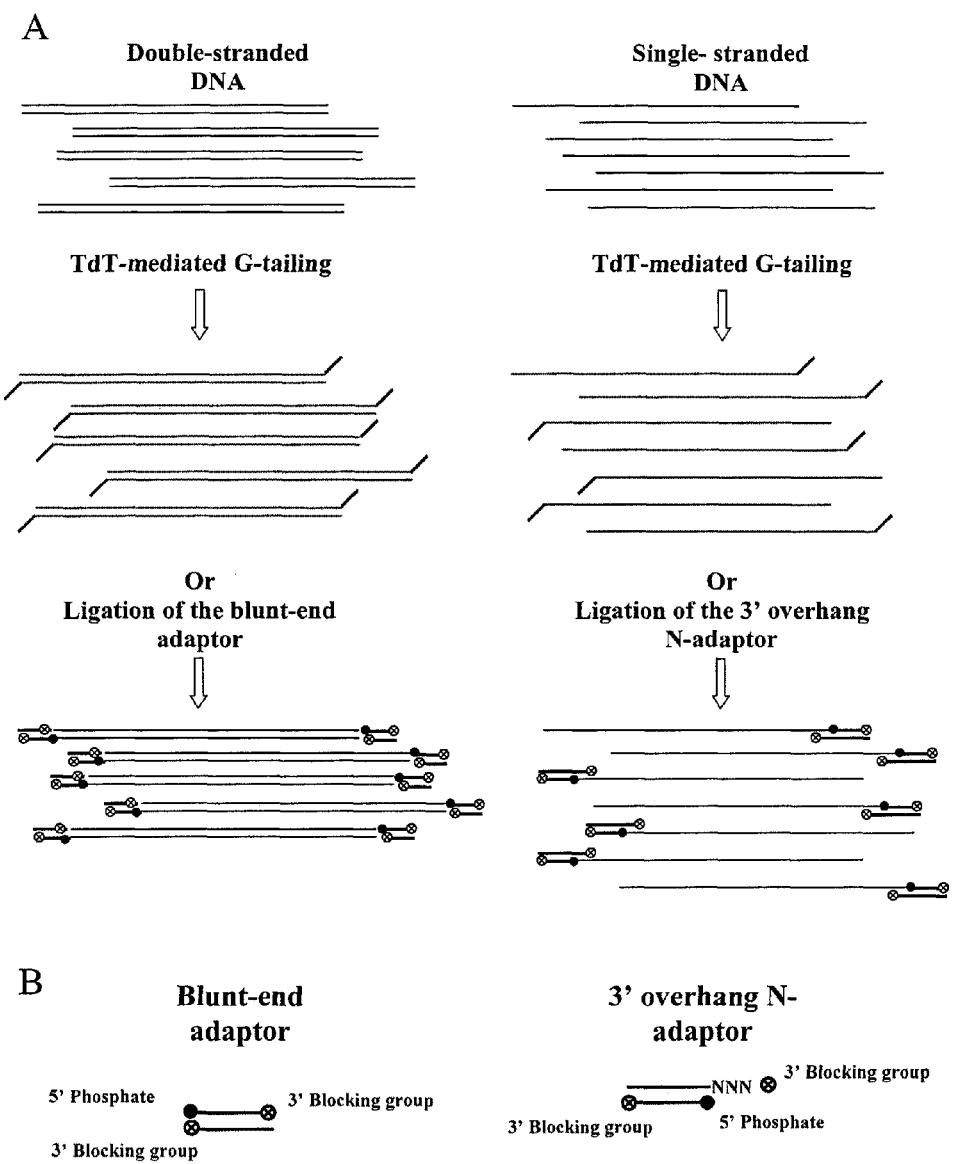
FIG. 3 demonstrates methods for adding a universal sequence to the 3' ends of DNA fragments.

A primer is attached to the ends of DNA fragments, preferably the 3' ends, and this can be achieved by any means known in the art. A skilled artisan recognizes that the primer can be, for example, a homopolymeric tail generated by terminal deoxynucleotidyltransferase or ligation of an adaptor sequence (FIG. 3).

The primer, in a specific embodiment, comprises a substantially known sequence. A skilled artisan recognizes that "substantially known" refers to having sufficient sequence information in order to permit preparation of a DNA molecule, including its amplification. This will typically be about 100%, although in some embodiments some of the primer sequence is random. Thus, in specific embodiments, substantially known refers to about 50% to about 100%, about 60% to about 100%, about 70% to about 100%, about 80% to about 100%, about 90% to about 100%, about 95% to about 100%, about 97% to about 100%, about 98% to about 100%, or about 99% to about 100%.

A skilled artisan recognizes that following fragmentation of the DNA, the generated fragment molecules may require conditioning, herein defined as modification to the ends to facilitate further steps for the fragment. For example, a 3' end may require conditioning following fragmentation, a 5' end may require conditioning following fragmentation, or both. In a specific embodiment, a 3' end requires conditioning following thermal fragmentation or mechanical fragmentation. In a further specific embodiment, the conditioning comprises modification of a 3' end lacking a 3' OH group. In an additional specific embodiment said 3' end is conditioned through exonuclease activity by an exonuclease, such as a 3' exonuclease, to enzymatically remove the distal nucleotides of the fragment molecule. In a preferred embodiment, terminal deoxynucleotidyltransferase is utilized for such an action. In an alternative embodiment, an enzyme other than terminal deoxynucleotidyltransferase is utilized, such as T4 DNA polymerase or DNA polymerase I, including Klenow.

1. Terminal Deoxynucleotidyltransferase Tailing

The most simple and fast protocol involves addition of guanine nucleotides by the enzyme terminal deoxynucleotidyltransferase (TdT) (FIG. 23A). In this case short (10-20 bases) poly G tails are synthesized at the 3' ends of DNA fragments. The fragments for TdT-mediated tailing could be double or single stranded. The poly G tails can also be efficiently added to the 3' DNA termini at the nicks introduced into DNA randomly, for example, by DNase I or another method (see, for example, U.S. Pat. No. 6,197,557 B1).

It is a general consensus that terminal transferase requires a 3' hydroxyl for addition of dGTP to synthesize the poly G tail (Grosse and Rougeon, 1993). In the present invention, terminal transferase is successfully used to tail DNA produced by hydrodynamic shearing and thermal fragmentation. Chain cleavage by heat seems to take place at the 3' side of the apurinic sugar residue and involve the β elimination reaction (Brown and Todd, 1955). As a result, 3' termini with a nucleotide end having a 3'-OH residue are only generated to a very minor extent (Kotaka and Baldwin, 1964; Lindahl and Andersson, 1972). Results presented on FIG. 23 and FIG. 24 demonstrate that terminal transferase can efficiently tail 3' DNA termini produced by thermal fragmentation, suggesting a novel 3' exonuclease activity for terminal deoxynucleotidyltransferase. Such "proofreading" activity is a well known feature of many DNA polymerases, but it was never documented before for terminal transferase.

Figure 4:
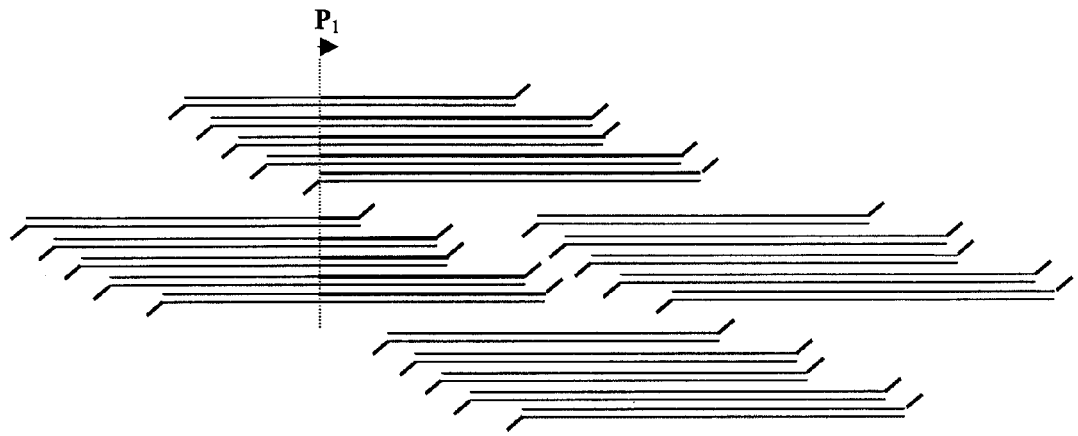
FIG. 4 illustrates amplification and sequencing of a DNA library produced by random fragmentation.
Figure 4:
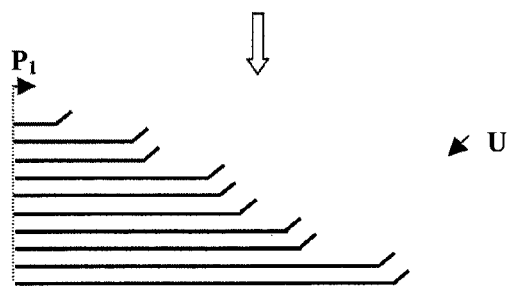
Figure 4:
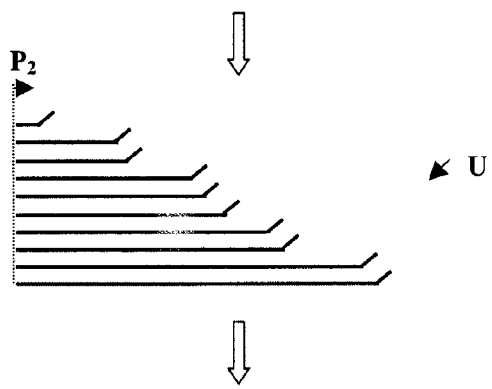
Figure 25:
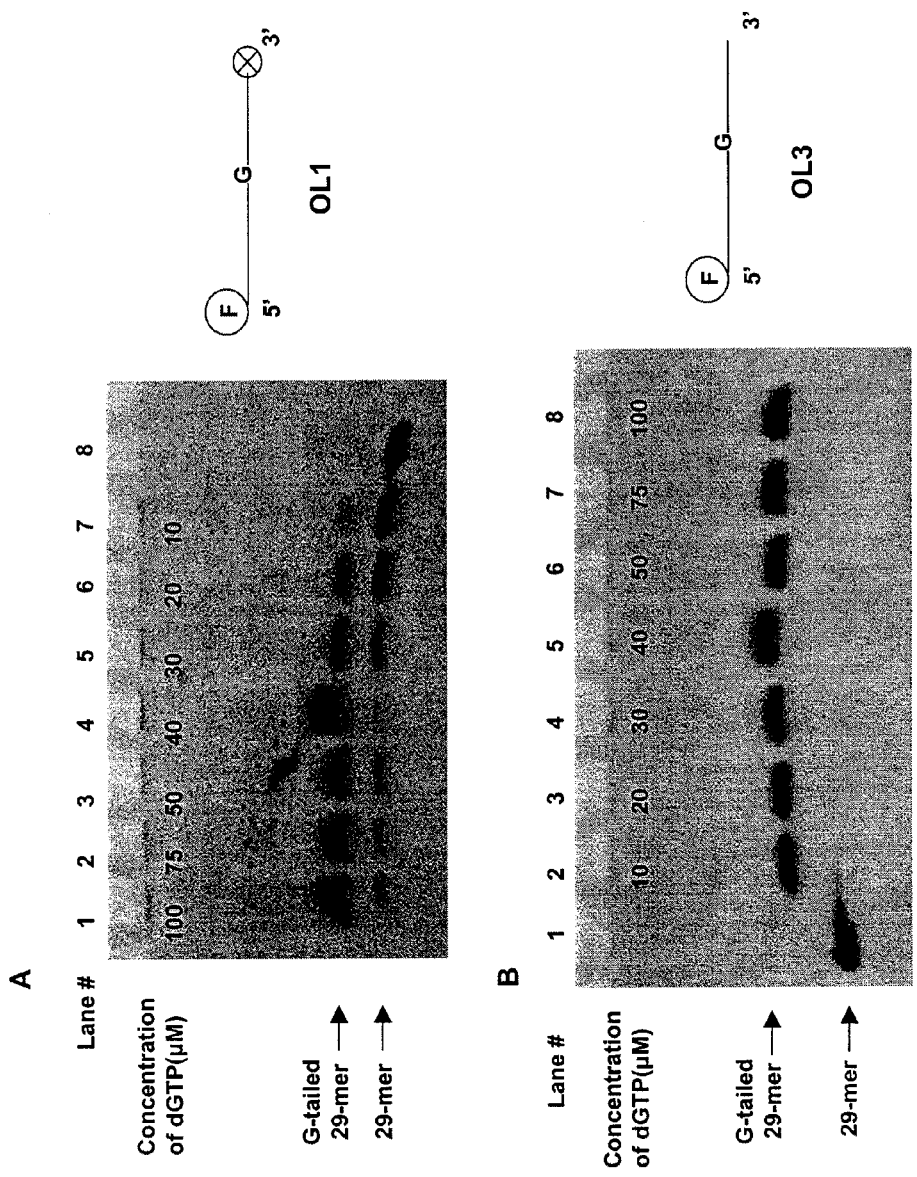
FIG. 25A shows effect of the dGTP concentration on efficiency of the TdT-mediated repair/tailing reaction when the substrate is 5' fluorescein-labeled oligonucleotides with blocking AmMod C7 group at the 3' end.
FIG. 25B shows effect of the dGTP concentration on efficiency of TdT-mediated tailing reaction when the substrate is 5' fluorescein-labeled oligonucleotide with native OH group at the 3' end.
Figure 26:
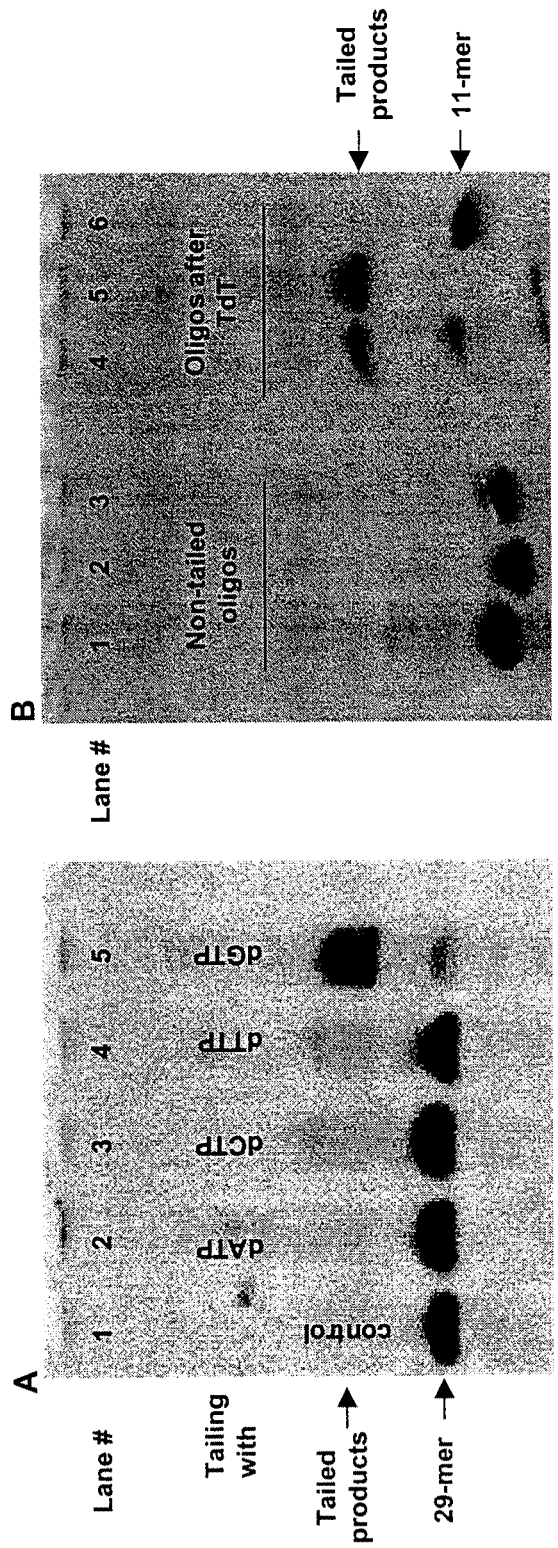
FIG. 26A demonstrates a unique role of the dGTP nucleotide in the TdT-mediated repair/tailing reaction on the 5' fluorescein-labeled oligonucleotide substrate with blocking AmMod C7 group at the 3' end.
FIG. 26B illustrates inability of the TdT enzyme to repair and elongate in the presence of dGTP an oligo template with dideoxy cytosine blocking group at the 3' end.
Figure 27:
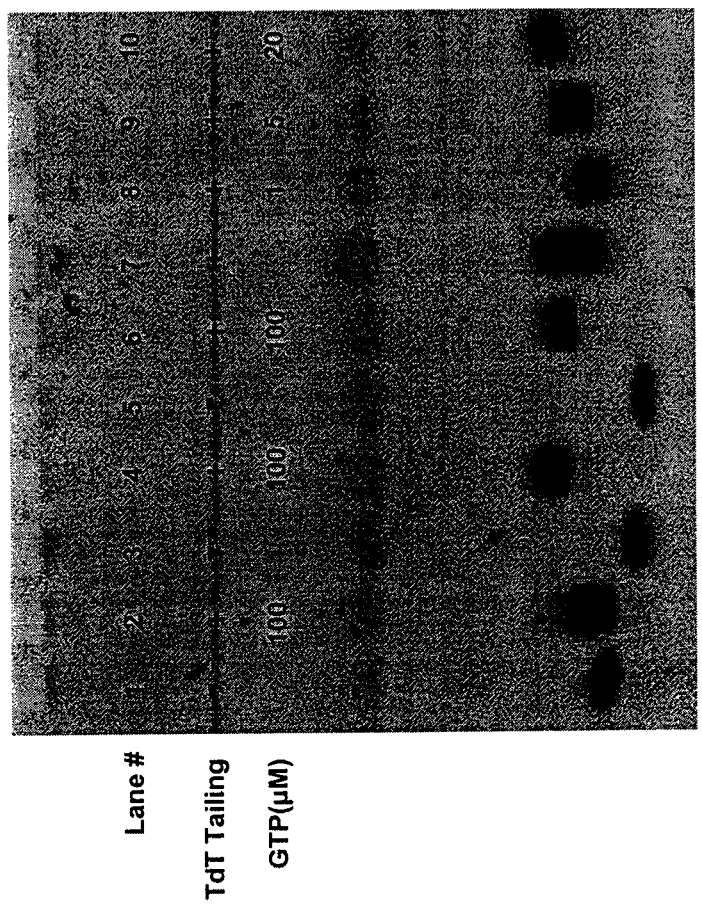
FIG. 27 shows that TdT-mediated riboGTP tailing of the oligonucleotide with blocking AmMod C7 group occurs after removal of the modified base and additional 1 or 2 bases from the 3' end of the substrate.

The repair activity of terminal transferase is very different from the 3' exo-activity of DNA polymerases: it requires a cofactor and is manifested only in the presence of dGTP nucleotide (FIG. 4 and FIG. 26). The absence of tailing of 3' blocked termini in the presence of dATP, dCTP and dTTP (FIG. 26) suggests a special role for deoxyguanine triphosphate in the repair process catalyzed by TdT. In fact, dGTP plays a dual role in the tailing mechanism catalyzed by terminal transferase. First, it serves as a cofactor that induces the end repair process and eliminates terminal residue(s), second, it serves as a substrate for the tailing reaction. The number of residues removed by terminal transferase 3' exonuclease activity constitutes about 1-3 bases (FIG. 27). The concentration of the dGTP is critical and should exceed about 40 μM (FIG. 25).

Figure 28:
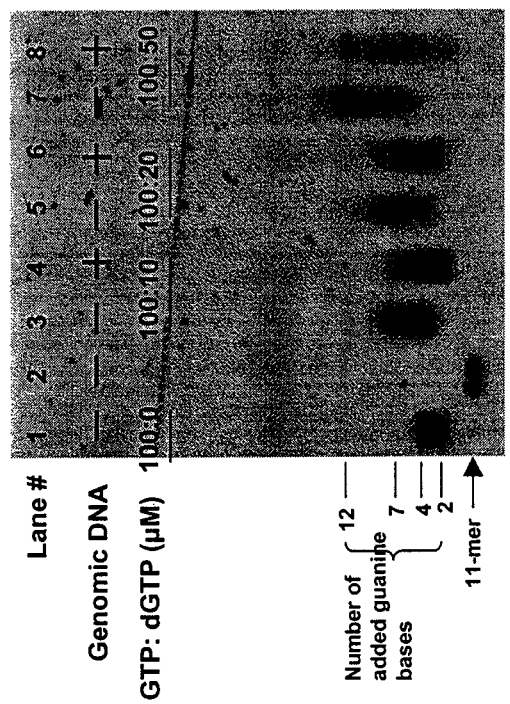
FIG. 28 demonstrates a length-controlled, TdT-mediated tailing reaction of the 5' fluorescein-labeled oligonucleotide substrate in the presence of a mixture of ribo- and deoxy GTP nucleotides.

Guanine triphosphate (riboGTP) can also stimulate the repair/tailing process by TdT enzyme (FIG. 27). Ribo-triphosphates are good substrates for terminal transferase but only a few bases can be incorporated (Boule et al., 2001). In this invention, a balanced mixture of ribo- and deoxy GTP nucleotide provides a solution for the length-controlled, TdT-mediated G-repair/tailing reaction that allowed addition of 8-12 guanine bases to DNA fragments produced by hydro-shearing or thermal fragmentation (FIG. 28).

2. Ligation of the Adaptor

There are two types of adaptors that can be ligated to the ends of randomly generated DNA fragments (FIG. 3B).

The "blunt-end" adaptor can be attached to the ends of double stranded DNA fragments produced by any fragmentation method (usually mechanical or enzymatic) (FIG. 3A; left side). Some methods of fragmentation would require an additional step that involves a repair of the DNA ends by T4 DNA polymerase and/or Klenow fragment and the removal of the 3' or 5' protrusions.

The structure of the "blunt-end" adaptor is shown on the left side of FIG. 3B, and it is similar to an adaptor of U.S. Pat. No. 6,197,557 B1 and U.S. patent application Ser. No. 09/860,738, both incorporated by reference herein. The most important feature of this adaptor is the blocking groups at both 3' ends that prevent adaptors from self-ligation. The phosphate group is present at one end of the adaptor to direct its ligation in only one orientation to DNA ends.

The "single-stranded DNA" adaptor with short 3' overhang containing 4-6 random bases (denoted "N" in FIG. 3B) and the phosphorylated recessive 5' end can be attached to the 3' ends of single stranded DNA molecules (FIG. 3A). Some methods of fragmentation would require an additional step that involves a repair of the 3' ends of single stranded molecules by the T4 DNA polymerase, Klenow fragment or exonuclease I.

The structure of the "single-stranded DNA" adaptor is shown on the right side of the FIG. 3B, and it is similar to the adaptor design of U.S. patent application Ser. No. 09/860, 738, incorporated by reference herein.

The adaptor has blocking groups at both 3' ends that prevent adaptors from self-ligation. The phosphate group is present at the recessive 5' end of the adaptor. The 4-6 base 3' overhang of the adaptor has a random base composition. In specific embodiments, it facilitates the annealing and ligation of the adaptor to single stranded DNA molecules.

C. Amplification and Direct Sequencing of Specific DNA Regions Using Randomly Fragmented and Tailed DNA Libraries The TRF library prepared by random DNA fragmentation is a highly redundant DNA library. Amplification of many overlapping DNA molecules by standard PCR™ using one sequence-specific and one universal primer (denoted "U" in FIG. 4) would result in selection and amplification of a very large population of molecules, specifically, a nested set of DNA fragments of different length which share the same priming site complementary to the primer $P_1$ (FIG. 4). Because the frequency of DNA breaks introduced by previously described techniques is high (potentially at every base position), the number of DNA fragments of different length amplified by PCR™ is also very large.

It is not obvious that the amplified molecules could be directly used for DNA sequencing using the same primer $P_1$ (or nested primer $P_2$) as a sequencing primer. Two factors could potentially affect the quality and length of the resulting sequencing ladder. First, the bias toward a preferential amplification of the shortest DNA fragments could reduce the length of DNA sequencing. Second, the overlap between the universal adaptor sequence (at the randomly created end) of short DNA fragments and the DNA sequence of longer fragments could result in ambiguities in the base identification in the region of overlap.

In confirmation of data presented in U.S. Patent Application Ser. No. 60/288,205, incorporated by reference herein, regarding libraries of nick translation-generated molecules, the inventors found that even more complex mixtures of nested molecules generated by PCR™ using TRF libraries (using one or more sequence-specific and one universal primers) can be also directly used for sequence analysis.

Figure 5:
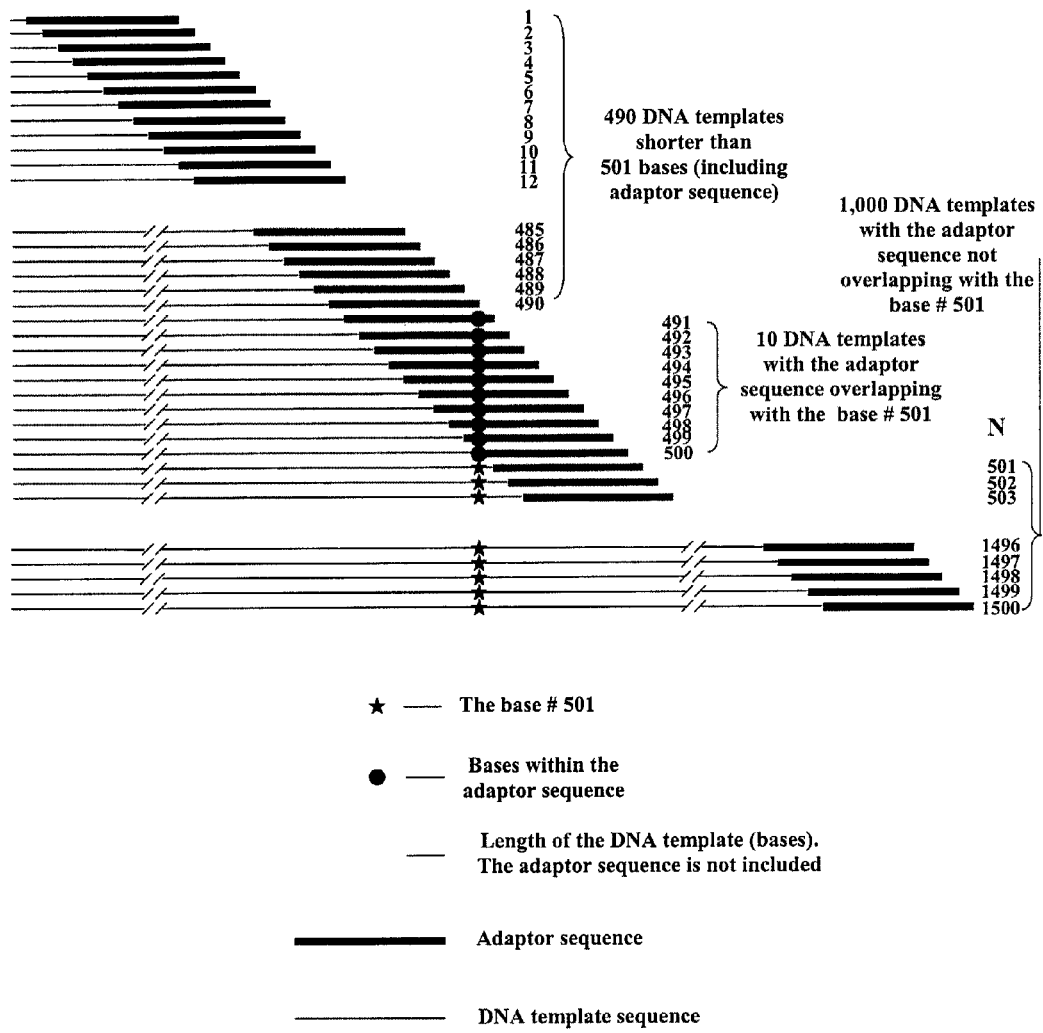
FIG. 5 demonstrates sequencing nested DNA templates: adaptor sequence contribution.

The adaptor sequence, which is located at different distances for different fragments, does not affect at all the quality of the sequencing data (FIG. 5). Assuming that the average size of the TRF library is 1500 bases and the size of the universal sequence at the 3' end (for example, G tail) is 10 bases, there are only 10 fragments that overlap at the randomly chosen base position within the DNA (the star on FIG. 5) with the adaptor sequence (a circle on FIG. 5). For example, at the base position number 501 (the distance from the 3' end of the sequencing primer) about 1000 molecules contribute correct DNA sequencing information, and only 10 templates produce a signal generated by the universal adaptor sequence (FIG. 5). The expected noise-to-signal ratio due to this overlap is only about 10/1000=1%. That number is much smaller than the noise-to-signal ratio estimated in the case of libraries produced by partial digestion with frequently cutting restriction enzymes (see U.S. Patent Application 60/288, 205). Practically, it means that the contribution of the adaptor sequence to the sequencing ladder in the case of DNA generated from the TRF library is negligible.

Figure 6:
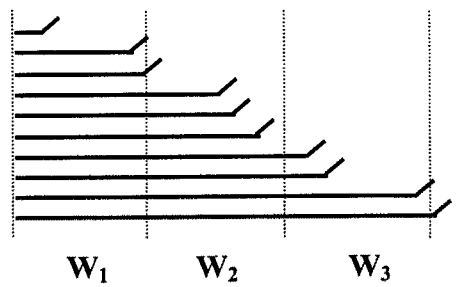
FIG. 6 shows sequencing by walking within the amplified DNA fragment mixtures.
Figure 6:
Figure 6:
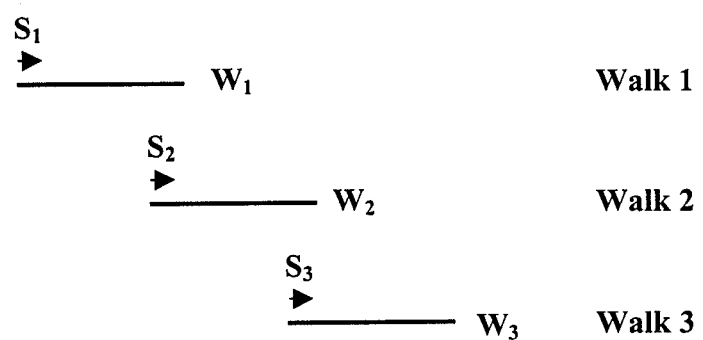

D. Sequencing by Primer "Walking" within the DNA Amplicons Generated from TRF Libraries The average size of DNA fragments within the TRF library sets a limit for the maximal length of DNA molecules within a population of nested molecules generated by PCR™, FIG. 6. The first sequencing primer $S_1$ (also a sequence-specific primer during PCR™ amplification step) would allow determination of the sequence of the region $W_1$ (600-800 bases). The rest of the amplicon can be sequenced using sequencing primers $S_2$ and $S_3$ by generating the sequence information for the regions $W_2$ and $W_3$, correspondingly.

This strategy can help to resolve problems that usually occur when sequencing DNA with repeats. By choosing the PCR™ primer in the unique DNA region (region $S_1$ on the FIG. 6) one can amplify larger pieces of DNA containing repetitive regions. For example, if the repetitive DNA element is within the region $W_2$, then the two unique sequences $W_1$ and $W_3$ would allow an unambiguous assembly of the sequencing reads $W_1$, $W_2$ and $W_3$ into a contiguous genomic sequence.

E. Nested DNA Fragments as a General Approach to Sequence Difficult DNA Templates There is an important reason why the use of mixtures of nested DNA molecules for DNA sequencing might be in general better than the use of standard DNA templates with a homogeneous size: plasmids, PCR™ products, etc. If one assumes that there are two regions A and B within the DNA fragment that can form an intra-molecular structure shown in FIG. 7A. During a sequencing reaction, the indicated region could introduce a problem for DNA polymerase to replicate through. As a result, the fragment will be only sequenced up to the region L.

Figure 7:
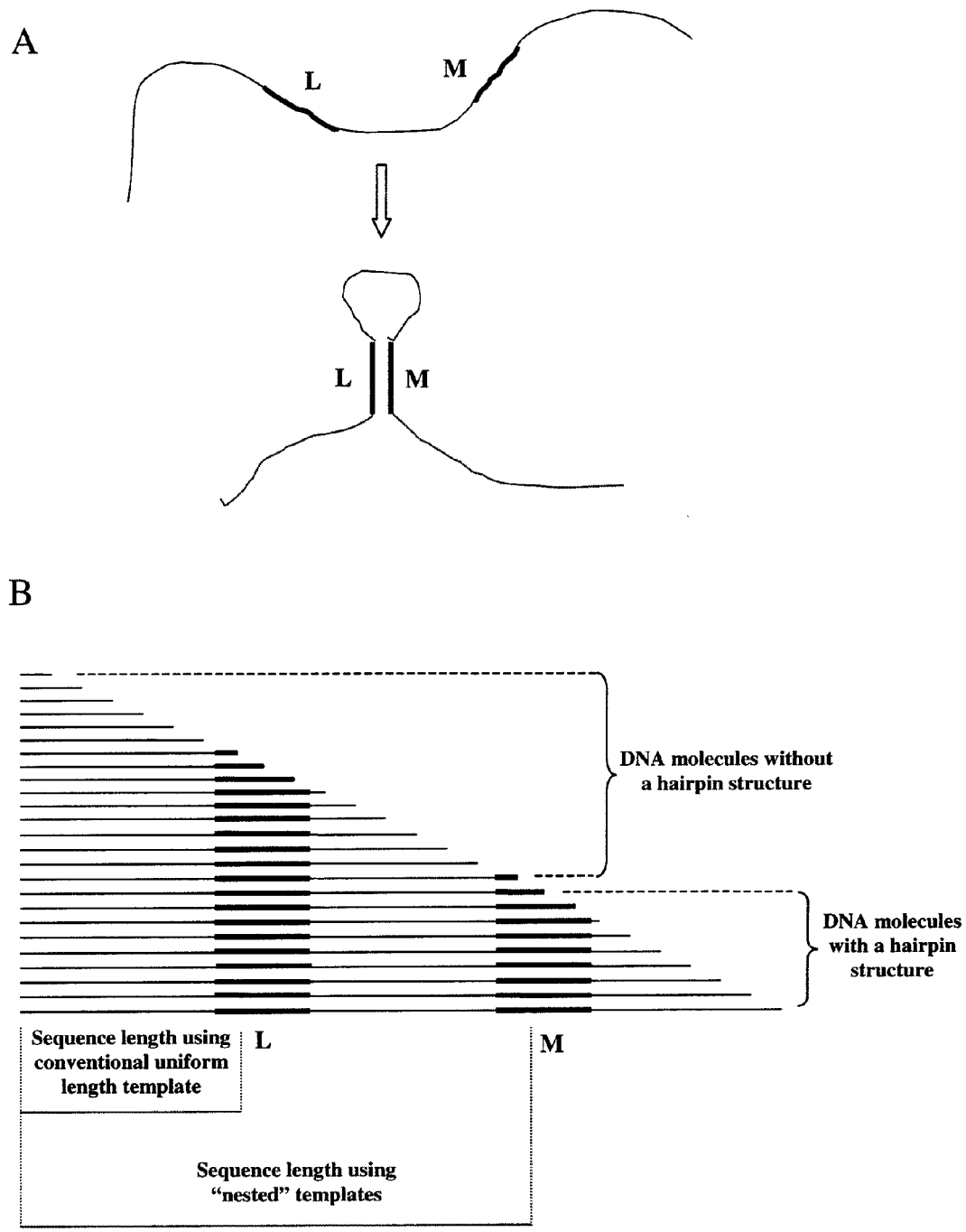
FIG. 7 shows sequencing of nested DNA fragments as a general approach for difficult templates.

In the case of a mixture of nested fragments, the DNA can be easily sequenced over much longer distance, FIG. 7B. In this case, a significant fraction of DNA molecules will not form a hairpin structure, so the polymerase can easily replicate the DNA and create a sequencing ladder up to the region M. A skilled artisan recognizes that there are multiple examples of secondary structure, including hairpins, G quartets, triple helices, and the like, and that the methods of the present invention are advantageous for preparing DNA molecules and subsequent manipulations, such as sequencing, having such structure.

There are several ways of implementing this method for general sequencing applications. First, the nested molecules can be generated by the procedures that have been described above. For example, recombinant plasmid DNA or PCR™ products are randomly fragmented, G-tailed with terminal deoxynucleotidyltransferase, and re-amplified by PCR™ using M13 primer (in the case of plasmid DNA) or one of primers used for generation of PCR™ product and universal polyC primer. This method potentially can handle very small amounts of the original (homogeneous in size) DNA template. Secondly, the preparation of the improved DNA templates for DNA sequencing can be limited to just random fragmentation of the original DNA.

F. Applications for the Present Invention

In specific embodiments, the methods of the present invention are utilized for an application, non-limiting examples of which are provided below.

In one embodiment, there is a method of conditioning a 3' end of a DNA molecule comprising exposing the 3' end to terminal deoxynucleotidyltransferase, wherein the terminal deoxynucleotidyltransferase comprises 3' exonuclease activity, a novel activity described herein. In preferred embodiments, the exposing step further comprises providing a guanine ribonucleotide, guanine deoxyribonucleotide, or both.

In another embodiment, there is a method of providing 3' exonuclease activity to the end of a DNA molecule comprising the step of introducing terminal deoxynucleotidyltransferase to the end of the molecule. In specific embodiments, the introducing step further comprises providing a guanine ribonucleotide, guanine deoxyribonucleotide, or both.

In an additional embodiment, there is a method of preparing a probe, comprising obtaining at least one DNA molecule; randomly fragmenting the DNA molecule to produce DNA fragments; attaching a labeled primer having substantially known sequence to at least one end of a plurality of the DNA fragments to produce labeled primer-linked fragments; and amplifying a plurality of the primer-linked fragments. In specific embodiments, the attaching step of a labeled primer comprises generation of a homopolymer extension of said DNA fragment, wherein said extension comprises the label. In a specific embodiment, the homopolymeric extension is generated by terminal deoxynucleotidyltransferase. In an alternative embodiment, the attaching step of a labeled primer comprises ligation of an adaptor molecule to at least one end of the DNA fragment, wherein the adaptor molecule comprises the label, examples of which include a radionuclide, an affinity tag, a hapten, an enzyme, a chromophore, or a fluorophore. The present invention also includes a labeled probe generated from this method or a kit comprising the probe.

In an additional embodiment of the present invention, there is a method of repairing a 3' end of at least one single stranded DNA molecule, comprising providing to the 3' end a terminal deoxynucleotidyltransferase. In a specific embodiment, the providing step further comprises providing a guanine ribonucleotide, guanine deoxyribonucleotide, or both. A skilled artisan recognizes that the term "repair" as used herein is defined as excision of at least one nucleotide from a 3' end of a DNA molecule, and polymerization. In a specific embodiment, the polymerization step is subsequent to the excision step. In a specific embodiment, the distal 3' nucleotide is damaged, a non-limiting example of which is defined as lacking a 3' OH group. In another embodiment, the terminal deoxynucleotidyltransferase comprises either activity for the excision of at least one nucleotide or comprises the activity for polymerization. In a specific embodiment, another enzyme facilitates an excision or polymerization process, or both. In a specific embodiment, in repair by terminal deoxynucleotidyltransferase, about 1-3 bases is excised prior to tailing in a polymerization reaction.

In another embodiment, there is a kit for repairing a 3' end of at least one single stranded DNA molecule, wherein said kit comprises a terminal deoxynucleotidyltransferase. In a further specific embodiment, the kit comprises a guanine ribonucleotide, guanine deoxyribonucleotide, or both, and in other specific embodiments the guanine ribonucleotide and/or guanine deoxyribonucleotide is labeled.

In an additional object of the present invention, there is a method of detecting a damaged DNA molecule, comprising the step of providing to the damaged DNA molecule terminal deoxynucleotidyltransferase and a labeled guanine ribonucleotide, labeled guanine deoxyribonucleotide, or both. In non-limiting examples, the damaged DNA molecule comprises a nick or a double stranded break, or both. In another specific embodiment, the providing step is further defined as providing repair to the damaged DNA molecule. In an additional specific embodiment, the label comprises a radionuclide, an affinity tag, a hapten, an enzyme, a chromophore, or a fluorophore. Factors causing DNA breaks in vivo include (ionizing) radiation, heat, UV light, oxygen, radicals, nitric oxide (NO), catecholamine, and/or apoptosis (nucleases). Factors causing DNA breaks in vitro include (ionizing) radiation, UV light, oxygen, radicals, metal ions, nucleases, mechanical/hydrodynamic forces, and/or chemical reagents.

II. DNA Sequencing

The present invention is directed to methods for preparing DNA molecules for DNA sequencing, particularly following amplification. A skilled artisan recognizes that the following methods are suitable for sequencing subsequent to generation of templates using methods described herein.

A. Maxam-Gilbert Method

The Maxam-Gilbert method involves degrading DNA at a specific base using chemical reagents. The DNA strands terminating at a particular base are denatured and electrophoresed to determine the positions of the particular base. The Maxam-Gilbert method involves dangerous chemicals, and is time- and labor-intensive. It is no longer used for most applications.

B. Sanger Method

The Sanger sequencing method is currently the most popular format for sequencing. It employs single-stranded DNA (ssDNA) created using special viruses like M13 or by denaturing double-stranded DNA (dsDNA). An oligonucleotide sequencing primer is hybridized to a unique site of the ssDNA and a DNA polymerase is used to synthesize a new strand complementary to the original strand using all four deoxyribonucleotide triphosphates (dATP, dCTP, dGTP, and dTTP) and small amounts of one or more dideoxyribonucleotide triphosphates (ddATP, ddCTP, ddGTP, and/or ddTTP), which cause termination of synthesis. The DNA is denatured and electrophoresed into a "ladder" of bands representing the distance of the termination site from the 5' end of the primer. If only one ddNTP (e.g., ddGTP) is used only those molecules that end with guanine will be detected in the ladder. By using ddNTPs with four different labels all four ddNTPs can be incorporated in the same polymerization reaction and the molecules ending with each of the four bases can be separately detected after electrophoresis in order to read the base sequence.

Although a variety of polymerases may be used, the use of a modified T7 DNA polymerase (Sequenase™) was a significant improvement over the original Sanger method (Sambrook et al., 1988; Hunkapiller, 1991). T7 DNA polymerase does not have any inherent 5'-3' exonuclease activity and has a reduced selectivity against incorporation of ddNTP. However, the 3'-5' exonuclease activity leads to degradation of some of the oligonucleotide primers. Sequenase™ is a chemically-modified T7 DNA polymerase that has reduced 3' to 5' exonuclease activity (Tabor et al., 1987). Sequenase™ version 2.0 is a genetically engineered form of the T7 polymerase which completely lacks 3' to 5' exonuclease activity. Sequenase™ has a very high processivity and high rate of polymerization. It can efficiently incorporate nucleotide analogs such as dITP and 7-deaza-dGTP which are used to resolve regions of compression in sequencing gels. In regions of DNA containing a high G+C content, Hoogsteen bond formation can occur which leads to compressions in the DNA. These compressions result in aberrant migration patterns of oligonucleotide strands on sequencing gels. Because these base analogs pair weakly with conventional nucleotides, intrastrand secondary structures during electrophoresis are alleviated. In contrast, Klenow does not incorporate these analogs as efficiently.

The use of Taq DNA polymerase and mutants thereof is a more recent addition to the improvements of the Sanger method (U.S. Pat. No. 5,075,216). Taq polymerase is a thermostable enzyme which works efficiently at 70-75° C. The ability to catalyze DNA synthesis at elevated temperature makes Taq polymerase useful for sequencing templates which have extensive secondary structures at 37° C. (the standard temperature used for Klenow and Sequenase™ reactions). Taq polymerase, like Sequenase™, has a high degree of processivity and like Sequenase 2.0, it lacks 3' to 5' nuclease activity. The thermal stability of Taq and related enzymes (such as Tth and Thermosequenase™) provides an advantage over T7 polymerase (and all mutants thereof) in that these thermally stable enzymes can be used for cycle sequencing which amplifies the DNA during the sequencing reaction, thus allowing sequencing to be performed on smaller amounts of DNA. Optimization of the use of Taq in the standard Sanger Method has focused on modifying Taq to eliminate the intrinsic 5'-3' exonuclease activity and to increase its ability to incorporate ddNTPs to reduce incorrect termination due to secondary structure in the single-stranded template DNA (EP 0 655 506 B1). The introduction of fluorescently labeled nucleotides has further allowed the introduction of automated sequencing, which increases productivity.

Sequencing DNA that is flanked by vector or PCR™ primer DNA of known sequence, can undergo Sanger termination reactions initiated from one end using a primer complementary to those known sequences. These sequencing primers are inexpensive, because the same primers can be used for DNA cloned into the same vector or PCR™ amplified using primers with common terminal sequences. Commonly-used electrophoretic techniques for separating the dideoxyribonucleotide-terminated DNA molecules are limited to resolving sequencing ladders shorter than 500-1000 bases. Therefore only the first 500-1000 nucleic acid bases can be "read" by this or any other method of sequencing the DNA. Sequencing DNA beyond the first 500-1000 bases requires special techniques.

C. Other Base-Specific Termination Methods

Other termination reactions have been proposed. One group of proposals involves substituting thiolated or boronated base analogs that resist exonuclease activity. After incorporation reactions very similar to Sanger reactions a 3' to 5' exonuclease is used to resect the synthesized strand to the point of the last base analog. These methods have no substantial advantage over the Sanger method.

Methods have been proposed to reduce the number of electrophoretic separations required to sequence large amounts of DNA. These include multiplex sequencing of large numbers of different molecules on the same electrophoretic device, by attaching unique tags to different molecules so that they can be separately detected. Commonly, different fluorescent dyes are used to multiplex up to 4 different types of DNA molecules in a single electrophoretic lane or capillary (U.S. Pat. No. 4,942,124). Less commonly, the DNA is tagged with large number of different nucleic acid sequences during cloning or PCR™ amplification, and detected by hybridization (U.S. Pat. No. 4,942,124) or by mass spectrometry (U.S. Pat. No. 4,942,124).

In principle, the sequence of a short fragment can be read by hybridizing different oligonucleotides to the unknown sequence and deciphering the information to reconstruct the sequence. This "sequencing by hybridization" is limited to fragments of DNA <50 bp in length. It is difficult to amplify such short pieces of DNA for sequencing. However, even if sequencing many random 50 bp pieces were possible, assembling the short, sometimes overlapping sequences into the complete sequence of a large piece of DNA would be impossible. The use of sequencing by hybridization is currently limited to re-sequencing, that is, testing the sequence of regions that have already been sequenced.

D. Preparing DNA for Determining Long Sequences

Because it is currently very difficult to separate DNA molecules longer than 1000 bases with single-base resolution, special methods have been devised to sequence DNA regions within larger DNA molecules. The "primer walking" method initiates the Sanger reaction at sequence-specific sites within long DNA. However, most emphasis is on methods to amplify DNA in such a way that one of the ends originates from a specific position within the long DNA molecule.

1. Primer Walking

Once part of a sequence has been determined (e.g., the terminal 500 bases), a custom sequencing primer can be made that is complementary to the known part of the sequence, and used to prime a Sanger dideoxyribonucleotide termination reaction that extends further into the unknown region of the DNA. This procedure is called "primer walking." The requirement to synthesize a new oligonucleotide every 400-1000 bp makes this method expensive. The method is slow, because each step is done in series rather than in parallel. In addition, each new primer has a significant failure rate until optimum conditions are determined. Primer walking is primarily used to fill gaps in the sequence that have not been read after shotgun sequencing or to complete the sequencing of small DNA fragments <5,000 bp in length. However, WO 00/60121 addresses this problem using a single synthetic primer for PCR™ to genome walk to unknown sequences from a known sequence. The 5'-blocked primer anneals to the denatured template and is extended, followed by coupling to the extended product of a 3'-blocked oligonucleotide of known sequence, thereby creating a single stranded molecule having had only a single region of known target DNA sequence. By sequencing an amplified product from the extended product having the coupled 3'-blocked oligonucleotide, the process can be applied reiteratively to elucidate consecutive adjacent unknown sequences.

2. PCR™ Amplification

PCR™ can be used to amplify a specific region within a large DNA molecule. Because the PCR™ primers must be complementary to the DNA flanking the specific region, this method is usually used only to prepare DNA to "re-sequence" a region of DNA.

3. Nested Deletion and Transposon Insertion

As described above, cloning or PCR™ amplification of long DNA with nested deletions brought about by nuclease cleavage or transposon insertion enables ordered libraries of DNA to be created. When exonuclease is used to progressively digest one end of the DNA there is some control over the position of one end of the molecule. However the exonuclease activity cannot be controlled to give a narrow distribution in molecular weights, so typically the exonuclease-treated DNA is separated by electrophoresis to better select the position of the end of the DNA samples before cloning. Because transposon insertion is nearly random, clones containing inserted elements have to be screened before choosing which clones have the insertion at a specific internal site. The labor-intense steps of clone screening make these methods impractical except for DNA less than about 10 kb long.

4. Junction-Fragment DNA Probes for Preparing Ordered DNA Clones

Collins and Weissman have proposed to use "junction-fragment DNA probes and probe clusters" (U.S. Pat. No. 4,710,465) to fractionate large regions of chromosomes into ordered libraries of clones. That patent proposes to size fractionate genomic DNA fragments after partial restriction digestion, circularize the fragments in each size-fraction to form junctions between sequences separated by different physical distances in the genome, and then clone the junctions in each size fraction. By screening all the clones derived from each size-fraction using a hybridization probe from a known sequence, ordered libraries of clones could be created having sequences located different distances from the known sequence. Although this method was designed to walk megabase distances along chromosomes, it was never put into practical use because of the necessity to maintain and screen hundreds of thousands of clones from each size fraction. In addition, cross hybridization would be expected to yield a large fraction of false positive clones.

5. Shotgun Cloning

The only practical method for preparing DNA longer than 5-20 kb for sequencing is subcloning the source DNA as random fragments small enough to be sequenced. The large source DNA molecule is fragmented by sonication or hydrodynamic shearing, fractionated to select the optimum fragment size, and then subcloned into a bacterial plasmid or virus genome (Adams et al., 1994; Primrose, 1998; Cantor and Smith, 1999). The individual subclones can be subjected to Sanger or other sequencing reactions in order to determine sequences within the source DNA. If many overlapping subclones are sequenced, the entire sequence for the large source DNA can be determined. The advantages of shotgun cloning over the other techniques are: 1) the fragments are small and uniform in size so that they can be cloned with high efficiency independent of sequence; 2) the fragments can be short enough that both strands can be sequenced using the Sanger reaction; 3) transformation and growth of many clones is rapid and inexpensive; and 4) clones are very stable E. Genomic Sequencing Current techniques to sequence genomes (as well as any DNA larger than about 5 kb) depend upon shotgun cloning of small random fragments from the entire DNA. Bacteria and other very small genomes can be directly shotgun cloned and sequenced. This is called "pure shotgun sequencing." Larger genomes are usually first cloned as large pieces and each clone is shotgun sequenced. This is called "directed shotgun sequencing."

1. Pure Shotgun Sequencing

Genomes up to several millions or billions of base pairs in length can be randomly fragmented and subcloned as small fragments (Adams et al., 1994; Primrose, 1998; Cantor and Smith, 1999). However, in the process of fragmentation all information about the relative positions of the fragment sequences in the native genome is lost. This information can be recovered by sequencing with 5-10-fold redundancy (i.e., the number of bases sequenced in different reactions add up to 5 to 10 times as many bases in the genome) so as to generate sufficiently numerous overlaps between the sequences of different fragments that a computer program can assemble the sequences from the subclones into large contiguous sequences (contigs). However, due to some regions being more difficult to clone than others and due to incomplete statistical sampling, there will still be some regions within the genome that are not sequenced even after highly redundant sequencing. These unknown regions are called "gaps." After assembly of the shotgun sequences into contigs, the sequencing is "finished" by filling in the gaps. Finishing must be done by additional sequencing of the subclones, by primer walking beginning at the edge of a contig, or by sequencing PCR™ products made using primers from the edges of adjacent contigs.

There are several disadvantages to the pure shotgun strategy: 1) as the size of the region to be sequenced increases, the effort of assembling a contiguous sequence from shotgun reads increases faster than N lnN, where N is the number of reads; 2) repetitive DNA and sequencing errors can cause ambiguities in sequence assembly; and 3) because subclones from the entire genome are sequenced at the same time and significant redundancy of sequencing is necessary to get contigs of moderate size, about 50% of the sequencing has to be finished before the sequence accuracy and the contig sizes are sufficient to get substantial information about the genome. Focusing the sequencing effort on one region is impossible.

2. Directed Shotgun Sequencing

The directed shotgun strategy, adopted by the Human Genome Project, reduces the difficulty of sequence assembly by limiting the analysis to one large clone at a time. This "clone-by-clone" approach requires four steps 1) large-insert cloning, comprised of a) random fragmentation of the genome into segments 100,000-300,000 bp in size, b) cloning of the large segments, and c) isolation, selection and mapping of the clones; 2) random fragmentation and subcloning of each clone as thousands of short subclones; 3) sequencing random subclones and assembly of the overlapping sequences into contiguous regions; and 4) "finishing" the sequence by filling the gaps between contiguous regions and resolving inaccuracies. The positions of the sequences of the large clones within the genome are determined by the mapping steps, and the positions of the sequences of the subclones are determined by redundant sequencing of the subclones and computer assembly of the sequences of individual large clones. Substantial initial investment of resources and time are required for the first two steps before sequencing begins.

This inhibits sequencing DNA from different species or individuals. Sequencing random subclones is highly inefficient, because significant gaps exist until the subclones have been sequenced to about 7×redundancy. Finishing requires "smart" workers and effort equivalent to an additional ~3× sequencing redundancy.

The directed shotgun sequencing method is more likely to finish a large genome than is pure shotgun sequencing. For the human genome, for example, the computer effort for directed shotgun sequencing is more than 20 times less than that required for pure shotgun sequencing.

There is an even greater need to simplify the sequencing and finishing steps of genomic sequencing. In principle, this can be done by creating ordered libraries of DNA, giving uniform (rather than random) coverage, which would allow accurate sequencing with only about 3 fold redundancy and eliminate the finishing phase of projects. Current methods to produce ordered libraries are impractical, because they can cover only short regions (~5,000 bp) and are labor-intensive.

F. Resequencing of DNA

The presence of a known DNA sequence or variation of a known sequence can be detected using a variety of techniques that are more rapid and less expensive than de novo sequencing. These "re-sequencing" techniques are important for health applications, where determination of which allele or alleles are present has prognostic and diagnostic value.

1. Microarray Detection of Specific DNA Sequences

The DNA from an individual human or animal is amplified, usually by PCR™, labeled with a detectable tag, and hybridized to spots of DNA with known sequences bound to a surface (Primrose, 1998; Cantor and Smith, 1999). If the individual's DNA contains sequences that are complementary to those on one or more spots on the DNA array, the tagged molecules are physically detected. If the individual's amplified DNA is not complementary to the probe DNA in a spot, the tagged molecules are not detected. Microarrays of different design have different sensitivities to the amount of tested DNA and the exact amount of sequence complementarity that is required for a positive result. The advantage of the microarray resequencing technique is that many regions of an individual's DNA can be simultaneously amplified using multiplex PCR™, and the mixture of amplified genetic elements hybridized simultaneously to a microarray having thousands of different probe spots, such that variations at many different sites can be simultaneously detected.

One disadvantage to using PCR™ to amplify the DNA is that only one genetic element can be amplified in each reaction, unless multiplex PCR™ is employed, in which case only as many as 10-50 loci can be simultaneously amplified. For certain applications, such as SNP (single nucleotide polymorphism) screening, it would be advantageous to simultaneously amplify 1,000-100,000 elements and detect the amplified sequences simultaneously. A second disadvantage to PCR™ is that only a limited number of DNA bases can be amplified from each element (usually <2000 bp). Many applications require re-sequencing entire genes, which can be up to 200,000 bp in length.

2. Other Methods of Re-Sequencing

Other methods such as mass spectrometry, secondary structure conformation polymorphism, ligation amplification, primer extension, and target-dependent cleavage can be used to detect sequence polymorphisms. All these methods either require initial amplification of one or more specific genetic elements by PCR™ or incorporate other forms of amplification that have the same deficiencies of PCR™, because they can amplify only a very limited region of the genome at one time.

III. Amplification of Nucleic Acids

Nucleic acids useful as templates for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid can be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety. Briefly, two synthetic oligonucleotide primers, which are complementary to two regions of the template DNA (one for each strand) to be amplified, are added to the template DNA (that need not be pure), in the presence of excess deoxynucleotides (dNTP's) and a thermostable polymerase, such as, for example, Taq (*Thermus aquaticus*) DNA polymerase. In a series (typically 30-35) of temperature cycles, the target DNA is repeatedly denatured (around 90° C.), annealed to the primers (typically at 50-60° C.) and a daughter strand extended from the primers (72° C.). As the daughter strands are created they act as templates in subsequent cycles. Thus, the template region between the two primers is amplified exponentially, rather than linearly.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR™ are described in U.S. Pat. No. 5,882,864.

A. LCR

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

B. Qbeta Replicase

Qbeta Replicase, described in PCT Patent Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected.

C. Isothermal Amplification

An isothermal amplification method, in which restriction endonucleases and ligases are used to achieve the amplification of target molecules that contain nucleotide thiophosphates in one strand of a restriction site also may be useful in the amplification of nucleic acids in the present invention. Such an amplification method is described by Walker et al. 1992, incorporated herein by reference.

D. Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

E. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

F. Transcription-Based Amplification

Other nucleic acid amplification procedures include transcription-based amplification systems (TAS), including nucleic acid sequence based amplification (NASBA) and 3SR, Kwoh et al., 1989; PCT Patent Application WO 88/10315 et al., 1989, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase, such as T7 or SP6. In an isothermal cyclic reaction, the RNAs are reverse transcribed into double stranded DNA, and transcribed once again with an RNA polymerase, such as T7 or SP6. The resulting products, whether truncated or complete, indicate target specific sequences.

G. Rolling Circle Amplification

Rolling circle amplification (U.S. Pat. No. 5,648,245) is a method to increase the effectiveness of the strand displacement reaction by using a circular template. The polymerase, which does not have a 5' exonuclease activity, makes multiple copies of the information on the circular template as it makes multiple continuous cycles around the template. The length of the product is very large—typically too large to be directly sequenced. Additional amplification is achieved if a second strand displacement primer is added to the reaction using the first strand displacement product as a template.

H. Other Amplification Methods

Other amplification methods, as described in British Patent Application No. GB 2,202,328, and in PCT Patent Application No. PCT/US89/01025, each incorporated herein by reference, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Miller et al., PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

Other suitable amplification methods include "RACE" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention, Wu et al., 1989, incorporated herein by reference).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of TRF Library from *E. coli* Genomic DNA by Hydrodynamic Shearing This example describes the preparation of TRF library of average size of 3 Kb from *E. coli* genomic DNA, particularly by hydrodynamic shearing (HydroShear device, GeneMachines) and terminal transferase mediated tailing with deoxyguanosine triphosphate (dGTP).

The prepared library allows reproducible amplification of many nested DNA mixtures using one sequence-specific primer and universal homopolymeric primer $C_{10}$ (containing ten cytosines). Sequencing of these mixtures using the same primer generates 600 to 800 base reads adjacent to chosen kernel primers.

DNA is isolated by standard purification from *E. coli*, such as strain MG1655 (purchased from Yale University), and diluted to 100 ng/µl in TE-L buffer (10 mM Tris-HCl, 0.1 mM EDTA, pH 7.5). The sample is incubated at 45° C. for 15 min. During the course of the incubation the DNA sample is vortexed at maximum speed for 30 sec every 3 min. The sample is then centrifuged at 16,000×g for 15 min at room temperature. The supernatant is slowly aspirated and transferred to a clean tube sacrificing the last 30 microliters.

Aliquots of 150 µl of the DNA prep are subjected to mechanical fragmentation on a HydroShear device (Gene Machines) for 20 passes at a speed code of 9 following the manufacturer's protocol. The sheared DNA has an average size of about 3 kb as predicted by the manufacturer and confirmed by gel electrophoresis. To prevent DNA carry-over contamination, the shearing assembly of the HydroShear is washed 3 times each with 0.2 M HCl, 0.2 M NaOH, and 5 times with TE-L buffer prior to and after fragmentation. All solutions are 0.2 µm filtered before use.

Homopolymeric G tails, consisting of about 10 to 15 nucleotides, are enzymatically added to the 3'-termini of the DNA fragments by terminal deoxynucleotidyl transferase. DNA template at 80 ng/µl is incubated with 10 units of New England Biolabs (NEB) terminal transferase in 1×NEB restriction buffer #4 containing 0.25 mM $CoCl_2$, and 2 µM dGTP in a final volume of 50 µl for 15 min at 37° C. The reaction is stopped by adding 5 µl of 0.5 M EDTA, pH 8.0. The sample is supplemented with ¹/₁₀ volume of 3 M sodium acetate, pH 5.0, precipitated with 2.5 volumes of ethanol in the presence of 2 µg glycogen, centrifuged 30 min at 16,000× g, and the pellet was then washed twice with 70% ethanol at room temperature and dissolved in TE-L buffer.

Example 2

Amplification and Sequencing of *E. coli* DNA Regions with Specific Primers from TRF Library Prepared by Hydrodynamic Shearing DNA AMPLIFICATION AND SEQUENCING USING DNA MOLECULES GENERATED BY RANDOM FRAGMENTATION This example describes amplification and sequencing of specific regions from an *E. coli* TRF library. During PCR™ amplification a specific primer is used along with a 10 base homopolymeric cytosine primer ($C_{10}$ primer). The resulting amplicon is then utilized as template for cycle sequencing with the same specific primer used in the PCR™.

Amplification primers are designed using Oligo version 6.53 primer analysis software (Molecular Biology Insights, Inc., Cascade, Colo.) Primers are 21 to 23 bases long, having high internal stability, low 3'-end stability, and melting temperatures of 57 to 62° C. (at 50 mM salt and 2 mM $MgCl_2$). Primers are designed to meet all standard criteria, such as low primer-dimer and hairpin formation, and are filtered against an *E. coli* genomic 6-mer frequency database.

For the purposes of non-limiting illustration, oligonucleotides for PCR™ amplifications are designed to target amplicons of six specific regions of the *E. coli* DNA: primers S1, S3, S7, S31, S36, and S41 (Table I).

TABLE I

Primers used for Positional Amplification and Sequencing of *E. coli* Genomic Regions, Human tp53 Gene Regions and Corn Genomic Regions from TRF Libraries

| Primer* ID | Sequence (5'-3') | Application |
|---|---|---|
| S1 | ATG TGG CGC GTA AAC TAT TGA (SEQ ID NO: 1) | primary amplification of target region at contig 1 of *E. coli* genome |
| S3 | CTG GCG GGA GTG AGT AGC AA (SEQ ID NO: 2) | primary amplification of target region at contig 2 of *E. coli* genome |
| S7 | TTC AAC TGG CGC AGG GCT AT (SEQ ID NO: 3) | primary amplification of target region at contig 4 of *E. coli* genome |
| S31 | TCT GCC AGC GCC CGT AAC AA (SEQ ID NO: 4) | primary amplification of target region at contig 12 of *E. coli* genome |
| S36 | CCA GCG CAT TCT GAC TAA ACC (SEQ ID NO: 5) | primary amplification of target region at contig 13 of *E. coli* genome |
| S41 | TCG CCC ATC TTC TCA CGT AG (SEQ ID NO: 6) | primary amplification of target region at contig 14 of *E. coli* Genome |
| T4 | GGT AGC CGT TGA GTC ACC CTC (SEQ ID NO: 7) | walking primer for S3 amplicon 645 bp apart from S3 |
| T5 | GCC GCA ATC AAT ACG ACC TGT (SEQ ID NO: 8) | walking primer for S3 amplicon 1272 bp apart from S3 |
| HS3+ | AGA AAA GCT CCT GAG GTG TAG AC (SEQ ID NO: 9) | primary amplification of target region encompassing exons 5, 6, and 7 of the human tp53 gene |
| HS4+ | CTC ATC TTG GGC CTG TGT TAT CT (SEQ ID NO: 10) | primary amplification of target region at exons 7, 8, and 9 of the human tp53 gene, also nested for priming site HS3+ |
| HB7- | CTG GGC CAG CAA GAC TTG ACA AC (SEQ ID NO: 11) | primary amplification of target region at exon 11 of the human tp53 gene |
| HS2+ | GAT CGA GAC CAT CCT GGC TAA CGG (SEQ ID NO: 12) | nested for priming site HS3+ |

TABLE I-continued

Primers used for Positional Amplification and Sequencing of E. coli Genomic Regions, Human tp53 Gene Regions and Corn Genomic Regions from TRF Libraries

| Primer* ID | Sequence (5'-3') | Application |
|---|---|---|
| HS14177+ | TGG GCC CAC CTC TTA CCG ATT TCT (SEQ ID NO: 13) | nested for priming site HS4+ |
| HB8- | AGC TGC CCA ACT GTA GAA ACT AC (SEQ ID NO: 14) | nested for priming site HB7- |
| asg60.s1 133+ | TAG TGT GCC CAG TGG TTA TAT TG (SEQ ID NO: 15) | primary amplification of corn region 1 |
| asg60.s1 405+ | GCG GTC CGA TGA GAT CAC TGT AG (SEQ ID NO: 16) | nested amplification of corn region 1 |
| Zea X 254- | TCT CAA GTG GTC CGC TAT TAT TC (SEQ ID NO: 17) | primary amplification of corn region 2 |
| Zea X 211- | GCC CGC GCA AGC CAT CCA TAG AG (SEQ ID NO: 18) | primary amplification of corn region 2 and nested for priming site Zea X 254- |
| Zea X 149- | ACC GAA TCC TCC TGC CGC AAA GT (SEQ ID NO: 19) | nested amplification of corn region 2 |
| Zea X 49- | CTA AAA GTC CAT AAC GGG ATG AC (SEQ ID NO: 20) | nested amplification of corn region 2 |
| MubG1 218- | TGA CAC AAC GGC TAC GAT TTA AT (SEQ ID NO: 21) | primary amplification of corn region 3 and nested for priming site MubG1 356- |
| MubG1 317- | GCC GCC GGA TTC AGC TAA ATT GT (SEQ ID NO: 22) | primary amplification of corn region 3 and nested for priming site MubG1 356- |
| MubG1 356- | CAC GAC CGG GTC ACG CTG CAC TG (SEQ ID NO: 23) | primary amplification of corn region 3 |
| MubG1 24- | GGC CGG GAC CGT TGA ACT AGA AC (SEQ ID NO: 24) | nested amplification of corn region 3 at priming site MubG1 218- |
| MubG1 393+ | TTT GGC CAT GAG TCG TGA CTT AG (SEQ ID NO: 25) | primary amplification of corn region 4 |
| MubG1 395+ | TGG CCA TGA GTC GTG ACT TAG TT (SEQ ID NO: 26) | primary amplification of corn region 4 |
| MubG1 428+ | GAC CGG TTC TCC TAG CTT GTT (SEQ ID NO: 27) | nested amplification of corn region 4 |
| MubG1 430+ | CCG GTT CTC CTA GCT TGT TCT AC (SEQ ID NO: 28) | nested amplification of corn region 4 |

*All primers are synthesized and purified by HPSF at MWG Biotech

Figure 8:
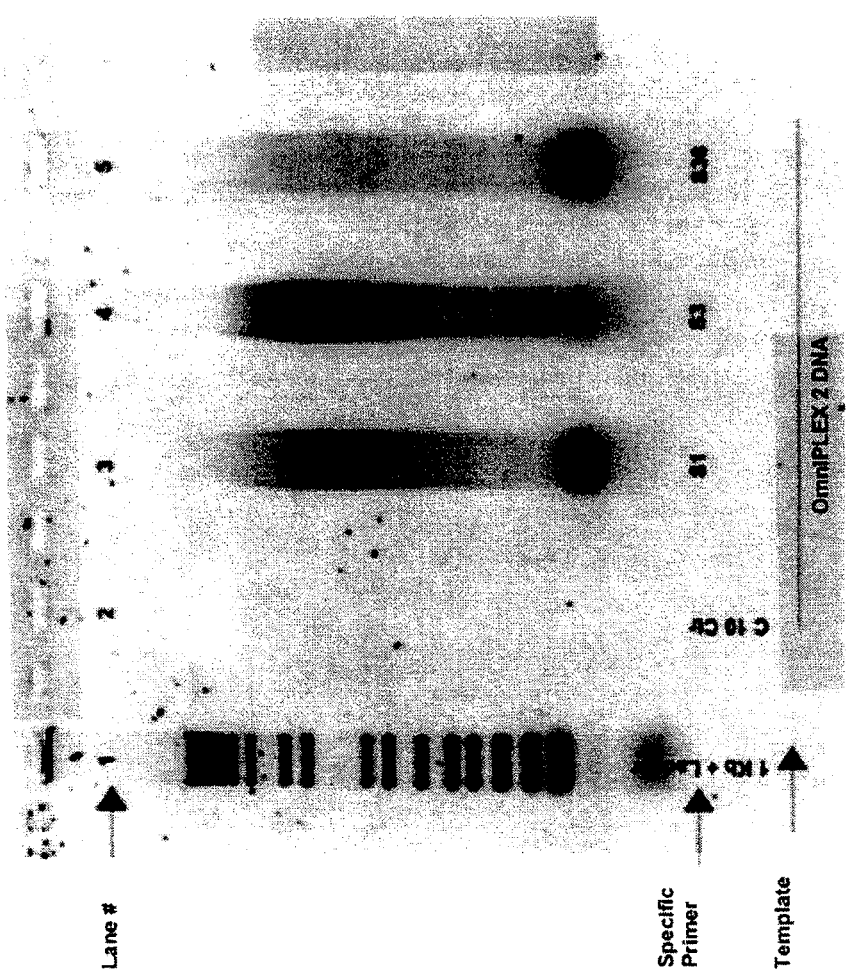
FIG. 8 illustrates primary amplification of three specific regions of the E. coli genome from a TRF library prepared by hydrodynamic shearing.
Figure 9:
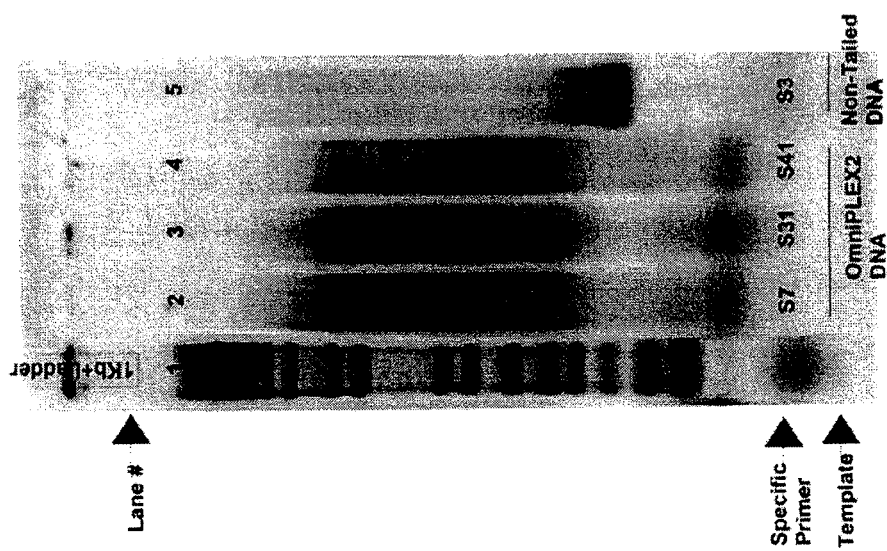
FIG. 9 is an additional example illustrating primary amplification of three specific regions of the E. coli genome from a TRF library prepared by hydrodynamic shearing.

PCR™ amplification is carried out with 200 nM specific primer, 200 nM of universal C-10 primer, and 40 ng of E. coli TRF library DNA (described in Example 1) in a final volume of 25 µl under standard Titanium Taq Polymerase conditions (Clontech). After initial denaturation at 94° C. for 2 min, samples are subjected to 32 cycles at 94° C. for 10 sec, 68° C. for 2 min and 15 sec, and a final extension at 72° C. for 2 min. Control reactions are performed under the same conditions with 200 nM of C-10 primer alone. Aliquots of 12 µl of each PCR™ reaction are analyzed by electrophoresis on a 1% agarose gel (FIG. 8 and FIG. 9). As shown, a specific discrete band is amplified from fragmented non-tailed DNA (FIG. 9), whereas a uniform smear is obtained when TRF library DNA is used as the template. This smear reflects the random process of fragmentation.

The PCR™ amplification products are quantified from the stained gel by comparison with standard DNA markers using the volume quantitation tool of Fluor-S Imager software (Bio Rad). The PCR™ products are purified free of primers and nucleotides by the QIAquick PCR™ purification kit (Qiagen), eluted in 30 µl of 1 mM Tris-HCl, pH 7.5 and used as template for cycle sequencing with the same primes used for PCR™.

Cycle sequencing is performed by mixing 2 to 11 µl of sequencing template, containing 40 to 250 ng of total DNA, with 1 µl of 5 µM each sequencing primer and 8 µl of DYEnamic ET terminator reagent mix (Amersham Pharmacia Biotech) in 96 well plates in final volume of 20 µl. Amplification is performed for 30 cycles at: 94° C. for 20 sec, 58° C. for 15 sec, and 60° C. for 75 sec. Samples are precipitated with 70% ethanol and analyzed on a MegaBACE 1000 capillary electrophoresis sequencing system (Amersham Pharmacia Biotech) using the manufacturer's protocol.

Table II shows a summary of the sequencing results obtained from the six regions of the E. coli genome.

TABLE II

Summary of the Sequencing Results for Specific Regions of the E. coli Genome and Human tp53 Gene Amplified from TRF Libraries Prepared by Hydrodynamic Shearing

| Sequenced Region* | Read Length at Phred >20** | Accuracy of the Read (% match with published sequence) |
|---|---|---|
| *E. coli* Genomic | | |
| S1 Region | 387 | 99% |
| S3 Region | 720 +/− 36 | 99% |
| S7 Region | 665 +/− 29 | 99% |
| S31 Region | 736 +/− 22 | 99% |
| S36 Region | 618 +/− 26 | 99% |
| S41 Region | 433 +/− 71 | 99% |
| T4 Region | 574 +/− 38 | 98% |
| T5 Region | 404 | 98% |
| Human tp53 | | |
| Region 1 (exons 6, 7, 8) | 705 +/− 59 | 98% |
| Region 2 (exons 7, 8, 9) | 683 +/− 64 | 98% |
| Region 3 (exon 11) | 267 n/a | 99% |

Figure 11:
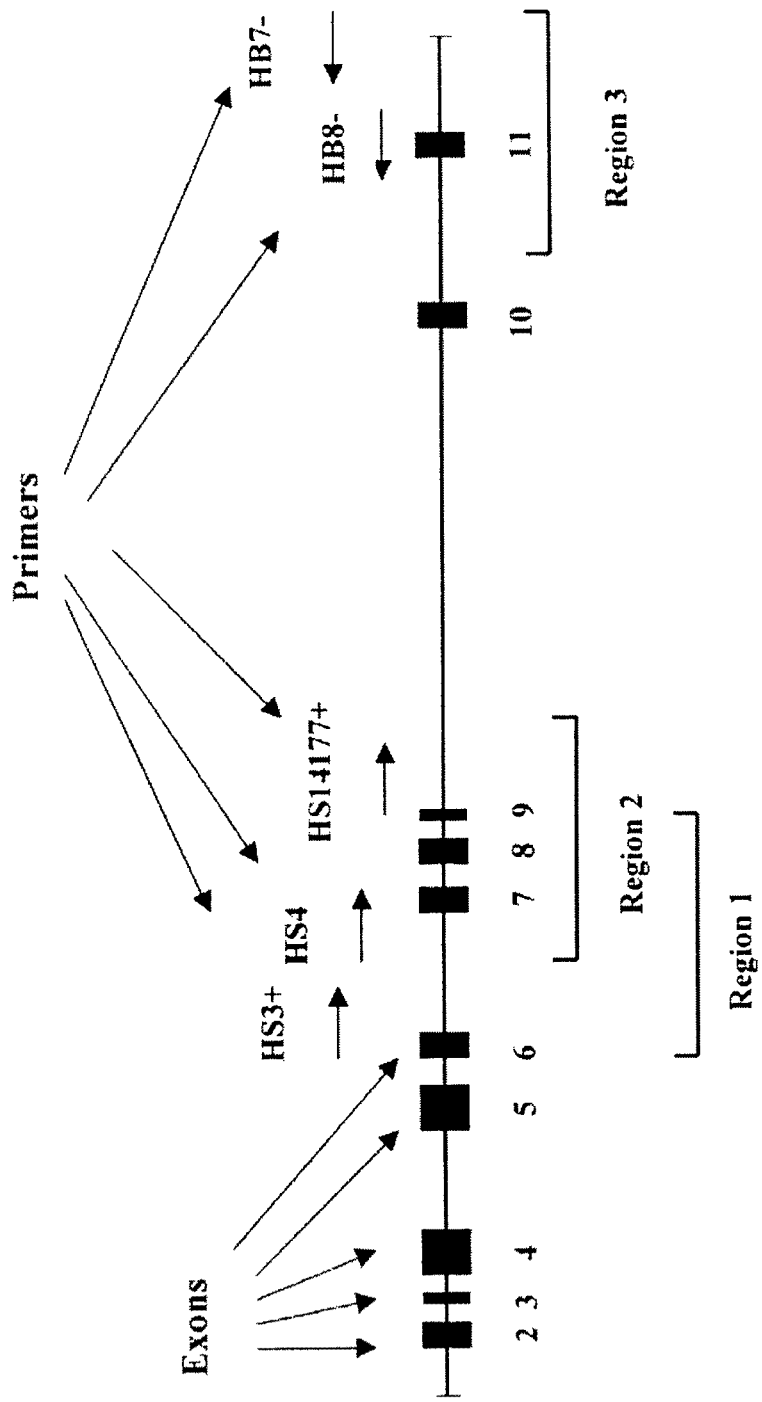
FIG. 11 illustrates a schematic presentation of a 10 Kb segment of the human tp53 gene containing regions amplified and sequenced from a TRF library.

*Refer to FIG. 11
**Mean +/− S.D. from multiple reads (see text) for human regions 1 and 2, bacterial regions S3, S7, S31, S36, S41 and T4, and single read for human region 3, and bacterial regions T5 and S1

The average read length of the analyzed sequences is above 600 bases. A sequence is considered to be a failure if 100 or fewer bases are identifiable. Valid sequencing reads were constrained to a preset threshold score of >20 using the Phred algorithm (Codon Code Corporation, Dedham, Mass.), which corresponds to an error probability of 1%. Sequence accuracy as compared to the published *E. coli* K12 MG1655 sequences is equal or greater than 98%.

Thus, this example demonstrates that specific genomic regions can be amplified and sequenced with a high level of accuracy and long read length from a TRF library generated from bacterial DNA by hydrodynamic shearing.

Example 3

Amplification and Sequencing by Primer Walking within the DNA Amplicons Generated from TRF Library This example describes the amplification and sequencing of a specific region from an *E. coli* TRF library (prepared by hydrodynamic shearing) by a primer walking approach. During Touch Down PCR™ (TD PCR™) amplification, the specific primer is used along with the universal 10-mer poly-C ($C_{10}$) primer. TD PCR™ conditions are chosen to increase the yield of amplified products. The resulting amplicon is then utilized as template for cycle sequencing with primers distal (in the 3' direction) to the amplification primer. The distal, or walking, primers are typically spaced to generate overlapping sequencing reads. Reads are then combined to form one long, contiguous sequence.

Primer S1 is designed to target amplification of one specific region of the *E. coli* DNA amplicon S1 (FIG. 1 and Table I). TD PCR™ amplification is performed with 300 nM specific primer, 300 nM of universal $C_{10}$ primer, and 40 ng of *E. coli* TRF library DNA (described in example 1) in a final volume of 25 µl under standard Titanium Taq Polymerase conditions (Clontech). After initial denaturing at 95° C. for 2 min, samples are subjected to 20 cycles at 95° C. for 15 sec, 73° C. for 2 min and 15 sec, with decreasing temperature of 0.5° C. in each cycle. The next round of amplification is 25 cycles at 95° C. for 15 sec and 60° C. for 2 min, with increasing time of extension of 1 sec each cycle.

The PCR™ product is purified free of primers and nucleotides by QIAquick PCR™ purification kit (Qiagen), eluted in 30 µl of 1 mM Tris-HCl, pH 7.5 and used as template for cycle sequencing with more distal walking primers.

Primers for sequencing and walking within the amplicon S1 are designed to be 600 to 700 bp apart from initial primers used for PCR™ amplification or from each other (primers T4 and T5; Table I). Cycle sequencing is performed as previously described (Example 2).

Figure 10:
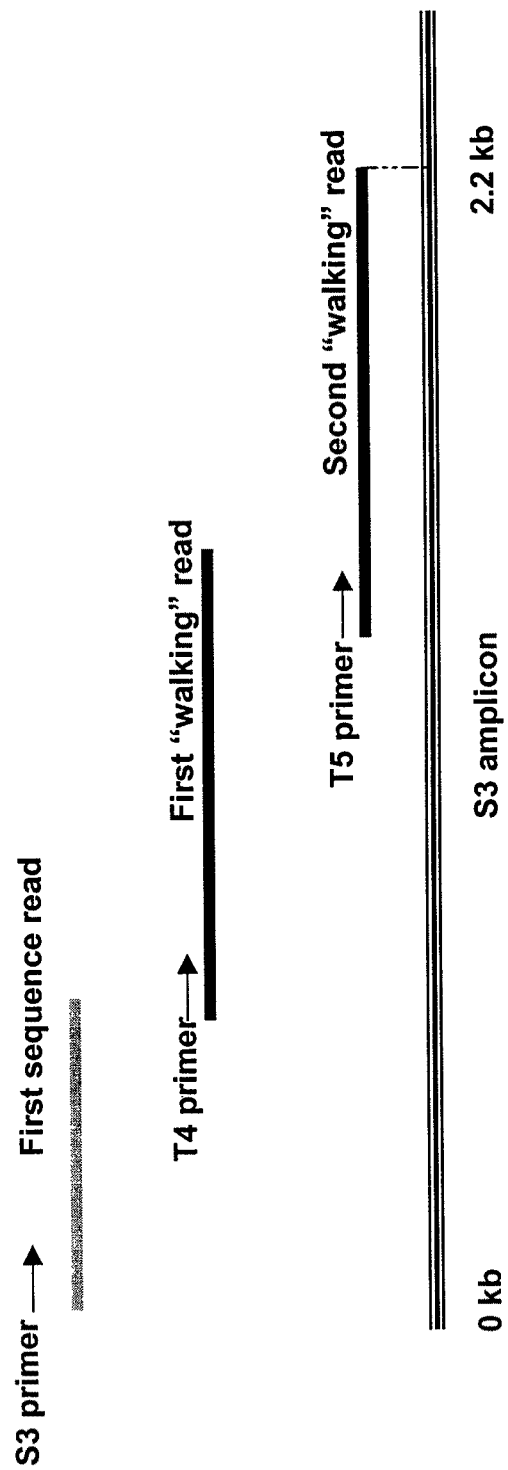
FIG. 10 is a schematic presentation of the specific region of E. coli genome sequenced by primer walking from a TRF library.

The analyzed genomic region (amplicon S1) is shown on FIG. 10. Sequencing of the first region is obtained by using S1 as a sequencing primer. The results are presented in Example 2 (see Table 2).

Sequencing of the second and third regions of the amplicon S1 (see FIG. 10) is achieved by using T4 and T5 sequencing ("walking") primers, respectively. Using this approach, 2.2 kb are sequenced of which 1.7 kb represent high quality sequence information (Phred score >20).

Table II shows a summary of the sequencing results obtained for the three specific regions of *E. coli* genome. The average read length of the analyzed sequences is 500 bases at a threshold score of >20 using the Phred algorithm. Sequence accuracy as compared to the published *E. coli* K12 MG1655 sequences is 98% or greater.

Thus, this example demonstrates the ability to "walk" on a distance of 2 kb within the amplicons generated from the TRF library.

Example 4

Preparation of TRF Library from Human Genomic DNA by Hydrodynamic Shearing

This example describes the preparation of TRF library of average size of about 3 kb from human genomic DNA by hydrodynamic shearing.

DNA is isolated by standard purification from fresh human lymphocytes and diluted to 100 ng/µl in TE-L buffer (10 mM Tris-HCl, pH 7.5; 0.1 mM EDTA, pH 7.5). The sample is incubated at 45° C. for 15 min. During the course of the incubation, the DNA sample is vortexed at maximum speed for 30 sec every 3 min. The sample is then centrifuged at 16,000×g for 15 min at room temperature. To avoid the presence of particulate matter, the supernatant is slowly aspirated and transferred to a clean tube, sacrificing the last 50 microliters.

Aliquots of 180 µl of the DNA prep are subjected to mechanical fragmentation on a HydroShear device (Gene Machines) for 20 passes at a speed code of 9 following the manufacturer's protocol. The sheared DNA has an average size of 3 kb as predicted by manufacturer and confirmed by gel electrophoresis. To prevent DNA carry-over contamination, the shearing assembly of the HydroShear is washed 3 times each with 0.2 M HCl, 0.2 M NaOH, and 5 times with TE-L buffer prior to and after fragmentation. All wash solutions were 0.2 µm filtered.

Homopolymeric G tails, consisting of 10-15 nucleotides, are enzymatically added to the 3'-termini of the DNA fragments by terminal deoxynucleotidyl transferase. Template DNA at 20 ng/µl is incubated with 40 units of New England Biolabs (NEB) terminal transferase in 1×NEB restriction buffer #4, 0.25 mM $CoCl_2$, and 2 µM dGTP in a final volume of 100 µl for 20 min at 37° C. The reaction is stopped by adding 4 µM EDTA, pH 8.0. The sample is supplemented with 1/10 volume of 3 M sodium acetate, pH 5.0, precipitated with 2.5 volumes of ethanol in the presence of 2 µg glycogen, centrifuged 30 min at 16,000×g, and the pellet was then washed twice with 70% ethanol at room temperature and dissolved in TE-L buffer. Library DNA is stored at −20° C.

Example 5

Positional Amplification and Sequencing of Human Tp53 Gene Regions from TRF Library Prepared by Hydrodynamic Shearing This example describes amplification and sequencing of specific human tp53 gene regions from a TRF library prepared by hydrodynamic shearing. In the primary step of PCR™ amplification, a specific proximal primer is used with the universal 10-mer poly-C($C_{10}$) primer. The amplified DNA is diluted and used as template for nested or secondary PCR™ amplification with specific distal primers in conjunction with the $C_{10}$ primer. The products of the nested amplification are then utilized as templates for cycle sequencing with the same primer used in nested PCR™ or with more distal sequencing primers.

Amplification primers are designed using Oligo version 6.53 primer analysis software (Molecular Biology Insights, Inc.; Cascade, Colo.). Primers are 21 to 23 bases long, having high internal stability, low 3'-end stability, and melting temperatures of 57-62° C. (at 50 mM salt and 2 mM $MgCl_2$). Primers are designed to meet all standard criteria, such as low primer-dimer and hairpin formation, and are filtered against a human genomic database 6-mer frequency table.

Figure 12:
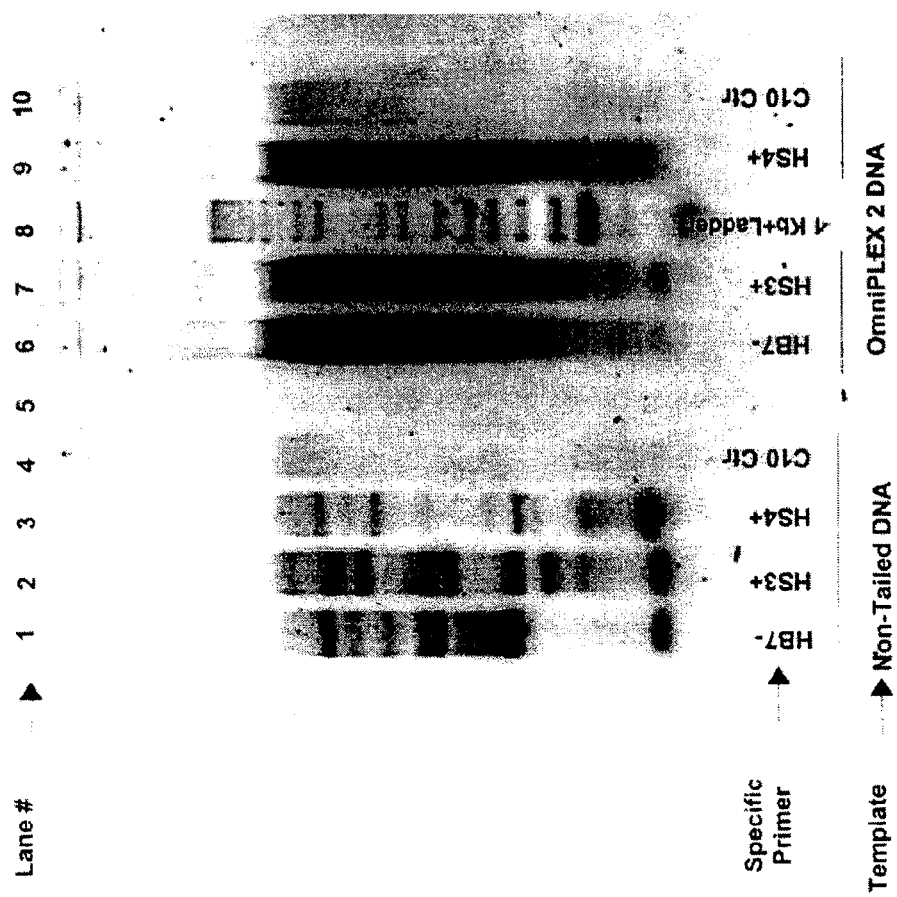
FIG. 12 shows primary amplification of three specific regions of the human tp53 gene from a TRF library prepared by hydrodynamic shearing.

Oligonucleotides for primary PCR™ amplifications are designed to target amplicons of three specific regions of the human tp53 gene: primer HS3+ specific for target region encompassing exons 5, 6, and 7, primer HS4+ for exons 7, 8, and 9, and primer HB7− for exon 11 (FIG. 11 and Table I). Primary PCR™ is carried out with 240 nM specific primer, 100 nM of universal $C_{10}$ primer, and 200 ng of human TRF library DNA (described in Example 4) in a final volume of 25 µl under standard Titanium Taq Polymerase conditions (Clontech; Palo Alto, Calif.). After initial denaturing at 94° C. for 2 min samples are subjected to 37 cycles at 94° C. for 10 sec, 68° C. for 2 min and 15 sec, and a final extension at 72° C. for 3 min. Control reactions are performed under the same conditions with 200 ng of fragmented but not tailed human DNA as template or with the $C_{10}$ primer alone. Aliquots of 15 µl of each PCR™ reaction are analyzed by electrophoresis on a 1% agarose gel (FIG. 12). As shown, specific patterns of discrete bands are amplified from fragmented, non-tailed DNA, whereas a uniform smear is obtained when TRF library DNA is used as the template. This smear reflects the random process of fragmentation and spans the region ranging from the average library size (i.e., 3 Kb) down to a few hundred base pairs in size.

Attempts to sequence primary amplicons from human TRF library directly with either the same primers used for primary amplification or nested primers were unsuccessful, which was unlike the sequencing results from bacterial TRF library amplicons (Example 2). In the case of the same primer utilized, the sequencing chromatograms are mixed, indicating the presence of more than one sequence. In the case of nested primers, the signal is too low, even if primer concentration was doubled or the template was increased to several hundred nanograms per sequencing reaction.

Figure 13:
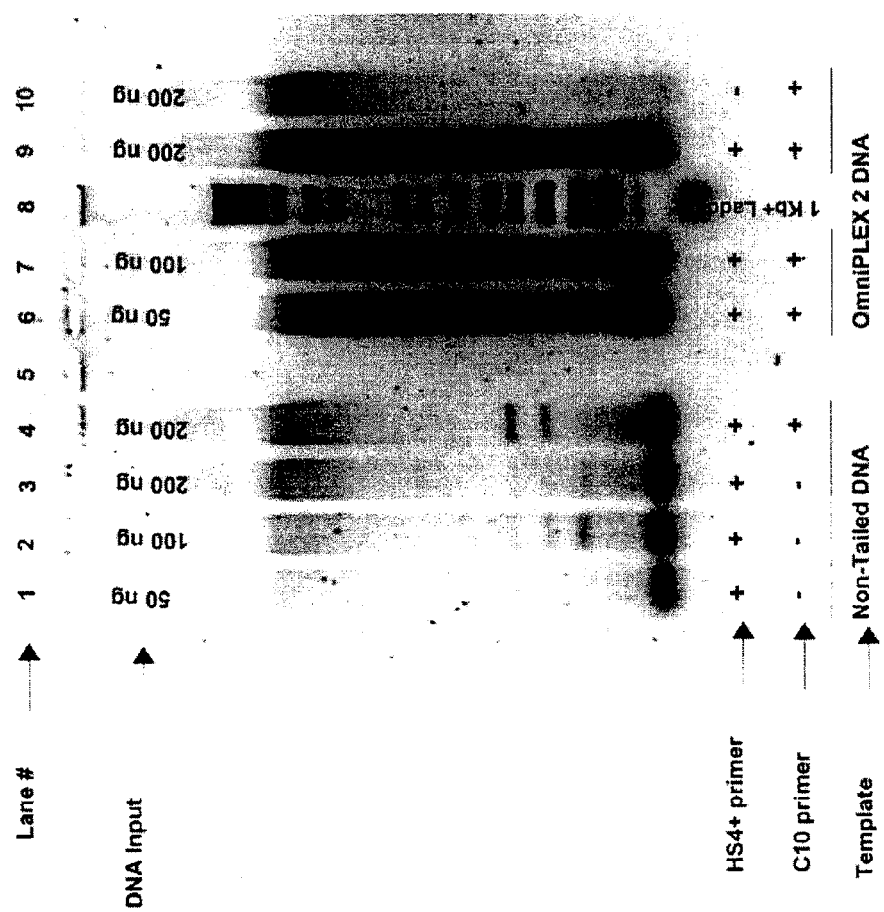
FIG. 13 demonstrates titration of the input amount of library DNA in primary amplification of HS4+ priming site of the human tp53 gene from a TRF library prepared by hydrodynamic shearing.

FIG. 13 presents titration of the amount of library DNA used in primary PCR™ amplification with HS4+ and $C_{10}$ primers. As shown, at the lowest amount of DNA used (i.e., 50 ng), there is no amplification of discrete bands in the control sample with non-tailed, sheared DNA, yet a smear was amplified in the G-tailed library sample. Higher amounts of template cause the appearance of multiple discrete bands in the controls. Thus, in subsequent primary amplifications the amount of template was kept at 50 ng per PCR™ reaction. An additional advantage of using a lower amount of DNA is the lack of discrete bands in the amplified smear from the G-tailed library. The presence of such bands can compromise the sequencing quality from secondary amplicons due to abrupt and premature decreases in signal intensity (FIG. 12, compare lane 6 and lane 9), especially if the bands are short products.

Figure 14:
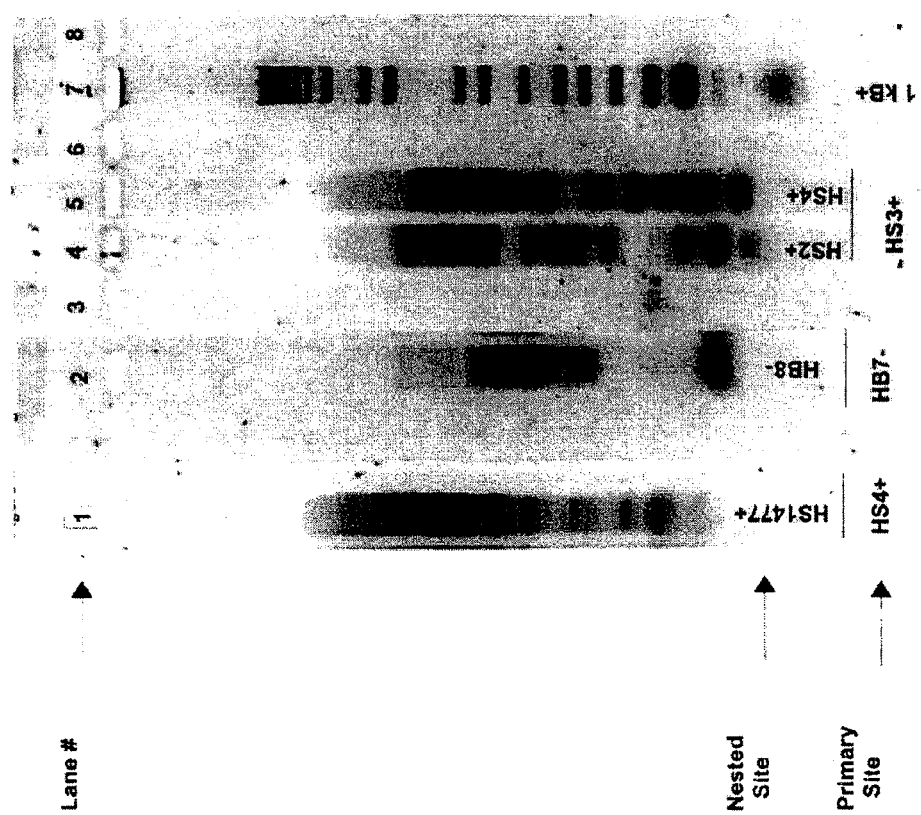
FIG. 14 shows secondary (nested) amplification of three genomic regions of the human tp53 gene from the hydrodynamically sheared TRF library used as sequencing templates.

Secondary PCR™ is performed with diluted primary amplicons as template, universal $C_{10}$ primer, and specific primers located downstream from the primary amplification sites. The primers used are: HS2+ and HS4+, nested for priming site HS3+; HS14177+, nested for priming site HS4+; and HB8−, nested for priming site HB7−(FIG. 11 and Table I). PCR™ amplification is carried out in duplicate 25 µl reactions with 200 nM nested primer, 100 nM $C_{10}$ primer, and 1 µl of 1,000 to 10,000-fold diluted primary amplicon as template. The PCR™ conditions included initial denaturation at 94° C. for 2 min, first cycle 94° C. for 10 sec, 68° C. for 2 min and 10 sec, and an incremental increase of extension time of 2 sec per cycle for 36 more cycles. Aliquots of 10 µl of each PCR™ reaction are analyzed by electrophoresis on 1% agarose gels (FIG. 14). As shown in the FIG., discrete patterns of amplified fragments are obtained in the secondary amplification.

The products of the secondary PCR™ amplifications are quantified from the stained gel against standard DNA marker bands using the volume quantitation tool of Fluor-S Imager software (BioRad; Hercules, Calif.). The nested PCR™ products are purified free of primers and nucleotides with the QIAquick PCR™ purification kit (Qiagen; Valencia, Calif.), eluted in 50 µl of 3 mM Tris-HCl, pH 7.5 and used as template for cycle sequencing with the same primers used for nested PCR™, or with additional nested primers for walking sequencing.

Cycle sequencing is carried out by mixing 2 to 11 µl of sequencing template, containing 40 to 250 ng of total DNA, with 1 µl of a 5 µM solution of each sequencing primer and 8 µl of DYEnamic ET terminator reagent mix (Amersham Pharmacia Biotech; Piscataway, N.J.) in 96 well plates in final volume of 20 µl. Amplification is performed for 30 cycles at: 94° C. for 20 sec, 58° C. for 15 sec, and 60° C. for 75 sec. Samples are precipitated with 70% ethanol and analyzed on a MegaBACE 1000 capillary electrophoresis sequencing system (Amersham Pharmacia Biotech; Piscataway, N.J.) using the manufacturer's protocol.

Table II shows a summary of the sequencing results obtained for the three targeted tp53 genomic regions. The average read length of the analyzed sequences is above 600 bases. A sequence is considered to be a failure if 100 or less bases are identifiable. Valid sequencing reads were constrained to a preset threshold score of >20 using the Phred algorithm (Codon Code Corporation; Dedham, Mass.), which corresponds to an error probability of 1%. Sequence accuracy as compared to the published human tp53 sequences (AF136270 and XM043211) is greater than or equal to 98%.

Thus, this example demonstrates that specific genomic loci can be amplified and sequenced with high level of accuracy from TRF libraries from higher eukaryotic organisms.

Example 6

Preparation of TRF Library from Corn Genomic DNA By Hydrodynamic Shearing

This example describes the preparation of TRF library of average size of about 3 Kb from corn genomic DNA by hydrodynamic shearing.

DNA from wild type 6N615 corn strain is isolated from seedlings using Roche (Nutley, N.J.) Plant DNA Isolation Kit (Cat #1667319) with the indicated modifications. Two grams of plant tissue material are frozen in liquid nitrogen and processed with five grinding beads by vortexing for 2 min at maximum speed. Beads are removed, and the pulverized plant material is lysed following the manufacturer's protocol for 10 min at 65° C. Proteins and other impurities are precipitated on ice, the supernatant is cleared by filtration through a cloth filter and total nucleic acids are precipitated at −20° C. for 20 min. The pellet is rinsed 3 times with 70% ethanol, dissolved in 300 p. 1 buffer #4 at 65° C., and the supernatant is treated with 18 µl of RNase cocktail (Ambion; Austin, Tex.) 500 U/ml RNase A, 20,000 U/ml RNase Ti) at 37° C. for 25 min. Following two extractions with phenol/chloroform/isoamyl alcohol (25:24:1 by volume), the aqueous phase is supplemented with ¹⁄₁₀ vol. of 3 M sodium acetate, pH 5.0 and 2.5 volumes of absolute ethanol at room temperature. The DNA pellet is rinsed 4 times with 70% room temperature ethanol, and DNA is dissolved in 300 µl of TE-L buffer (10 mM Tris-HCl, 0.1 mM EDTA, pH 7.5). The typical yield is 30 to 60 µg DNA per gram of tissue.

Genomic DNA is diluted to 100 ng/µl in TE-L buffer. The sample is incubated at 45° C. for 5 min, vortexed for 2 min at maximum speed, and centrifuged at 16,000×g for 10 min at room temperature. To avoid the presence of particulate matter, the supernatant is slowly aspirated and transferred to a clean tube sacrificing the last 50 microliters. Aliquots of 180 µl of the DNA prep are subjected to mechanical fragmentation using the HydroShear device (Gene Machines) for 20 passes at a speed code of 9 following the manufacturer's protocol. The sheared DNA has an average size of 3 kb as predicted by manufacturer and confirmed by gel electrophoresis. To prevent DNA carry-over contamination, the shearing assembly of the HydroShear is washed 3 times each with 0.2 M HCl, 0.2 M NaOH, and 5 times with TE-L buffer prior to and after fragmentation. All solutions are 0.2 µm filtered before use.

Homopolymeric G-tails, consisting of about 10 to 15 nucleotides, are enzymatically added to the 3'-termini of the DNA fragments by terminal deoxynucleotidyl transferase. DNA template at 20 ng/µl is incubated with 40 units of New England Biolabs (NEB; Beverly, Mass.) terminal transferase in 1×NEB restriction buffer #4 containing 0.25 mM $CoCl_2$, and 5 to 20 µM dGTP in a final volume of 100 µl for 20 min at 37° C. Reaction is stopped by adding 4 µl of 0.5 M EDTA, pH 8.0. The sample is supplemented with 1/10 vol. of 3 M sodium acetate, pH 5.0, precipitated with 2.5 volumes of ethanol in the presence of 2 µg glycogen, centrifuged 30 min at 16,000×g, and the pellet was then washed twice with 70% ethanol at room temperature and dissolved in TE-L buffer. Aliquots of 1 µg of the library are analyzed by electrophoresis on a 1% agarose gel. Library DNA is stored at 20° C.

Example 7

Figure 15:
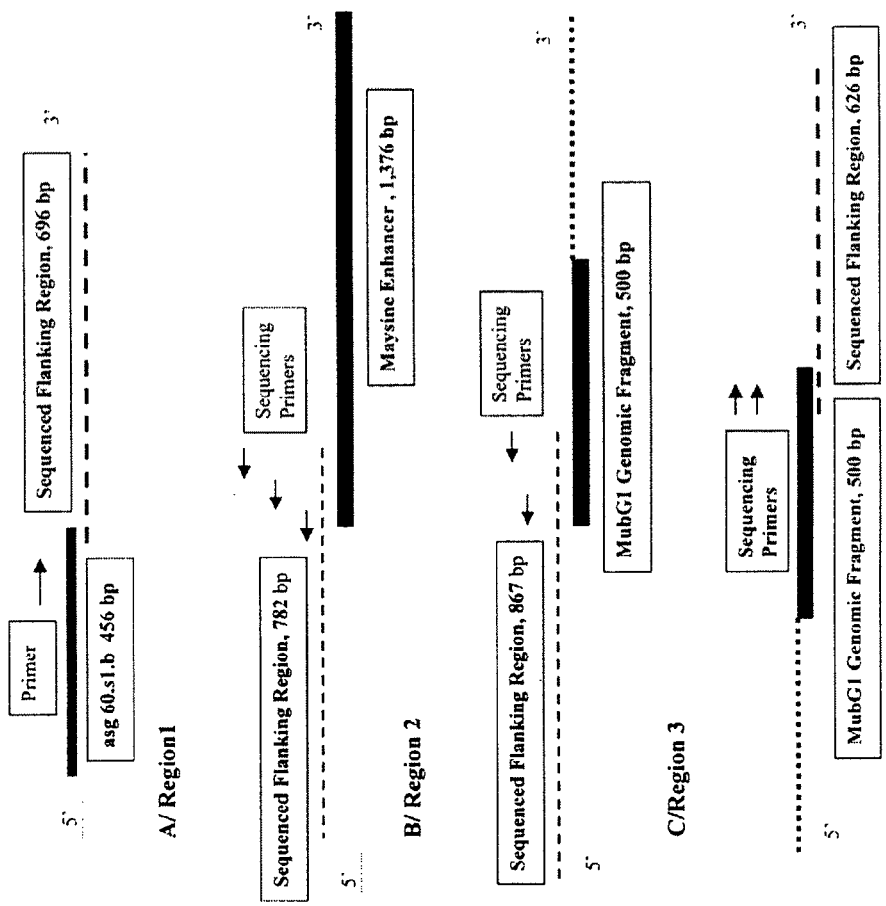
FIG. 15 illustrates a schematic presentation of four corn genomic regions sequenced from a TRF library.

Positional Amplification and Sequencing of Four Genomic Regions in Corn from a TRF Library Prepared by Hydrodynamic Shearing This example describes amplification and sequencing of four specific corn genomic regions from a TRF library (FIG. 15). In the primary step of PCR™ amplification, a proximal primer is used along with universal 10-mer poly-C($C_{10}$) primer. The amplified DNA is diluted and used as template for nested or secondary PCR™ amplification with a distal primers and $C_{10}$ primer. The products of the nested amplification are then utilized as templates for cycle sequencing with the same primer used in nested PCR™ or with more distal walking sequencing primers.

Amplification primers are designed using Oligo version 6.53 primer analysis software (Molecular Biology Insights, Inc., Cascade, Colo.) Primers are 21-23 base long, having high internal stability, low 3'-end stability, and melting temperatures of 57-62° C. (at 50 mM salt and 2 mM $MgCl_2$). Primers are designed to meet all standard criteria such as low primer-dimer and hairpin formation and are filtered against a corn genomic database ti-mer frequency table.

Primary PCR™ is carried out with 200 nM specific primer, 100 nM of universal $C_{10}$ primer, and 80 ng of corn TRF library DNA (described in Example 6) in a final volume of 25 µl under standard Titanium Taq Polymerase conditions (Clontech). After initial denaturing at 94° C. for 2 min, samples are subjected to 37 cycles at 94° C. for 10 sec, 68° C. for 2 min and 15 sec, and a final extension at 72° C. for 3 min. In some cases (genomic regions 3 and 4; see below) primary PCR™ amplification is done by initial denaturing at 94° C. for 2 min, first cycle 94° C. for 10 sec, 68° C. for 2 min and 10 sec, and incremental increase of extension time of 2 sec per cycle for 36 more cycles. Control reactions are performed under the same conditions with 80 ng of fragmented but not tailed human DNA as template. Aliquots of 12 µl of each PCR™ reaction are analyzed by electrophoresis on 1% agarose gels.

Secondary (nested) PCR™ is carried out with diluted primary amplicons as template, universal $C_{10}$ primer, and specific primers downstream from the primary amplification sites. PCR™ amplification is in duplicate 25 µl reactions with 200 nM nested primer, 150 nM C-10 primer, 1 µl of 1,000× diluted primary amplicon as template by initial denaturing at 94° C. for 2 min, first cycle 94° C. for 10 sec, 68° C. for 2 min and 10 sec, and incremental increase of extension time of 2 sec per cycle for 36 more cycles. Aliquots of 10 µl of each PCR™ reaction are analyzed by electrophoresis on 1% agarose gels.

The products of the secondary PCR™ amplifications are quantified against standard DNA marker bands using the volume quantitation tool of Fluor-S Imager software (Bio Rad). The nested PCR™ products are purified free of primers and nucleotides using the QIAquick PCR™ purification kit (Qiagen), eluted in 50 µl of 3 mM Tris-HCl, pH 7.5 and used as template for cycle sequencing with the same primes used for nested PCR™ or with additional nested primers for walking sequencing. Cycle sequencing is carried by mixing 2 to 11 µl of sequencing template containing 40 to 250 ng of total DNA with 1 µl of each sequencing primer at 5 µM, and 8 µl of DYEnamic ET terminator reagent mix (Amersham Pharmacia Biotech; Piscataway, N.J.) in 96 well plates in a final volume of 20 µl. Amplification is for 30 cycles at: 94° C. for 20 sec, 58° C. for 15 sec, and 60° C. for 75 sec. Samples are precipitated with 70% ethanol and analyzed on a MegaBACE 1000 capillary electrophoresis sequencing system (Amersham Pharmacia Biotech; Piscataway, N.J.) using the manufacturer's protocol. A sequence is considered to be a failure if 100 or less bases are identifiable. Valid sequencing reads were constrained to a preset threshold score of >20 using the Phred algorithm (Codon Code Corporation, Dedham, Mass.), which corresponds to an error probability of 1%.

The following genomic regions are analyzed (see FIG. 15):

Region 1. asg60.s1b.

The sequence is a 456 bp STS mapped to chromosome 5 published in Cold Spring Harbor Maize Genome Analysis Database (which can be found on their website). The unknown downstream flanking region is amplified and sequenced using primer asg60.s1 133+ for primary amplification and primer asg60.s1 405+ for both nested amplification and sequencing (Table I). The average read length from three individual sequencing runs is 562 bases (range 547-581) at a Phred score of >20. A consensus sequence of 696 bp is assembled from the three sequencing chromatogram files.

Region 2. Maysine enhancer.

Figure 16:
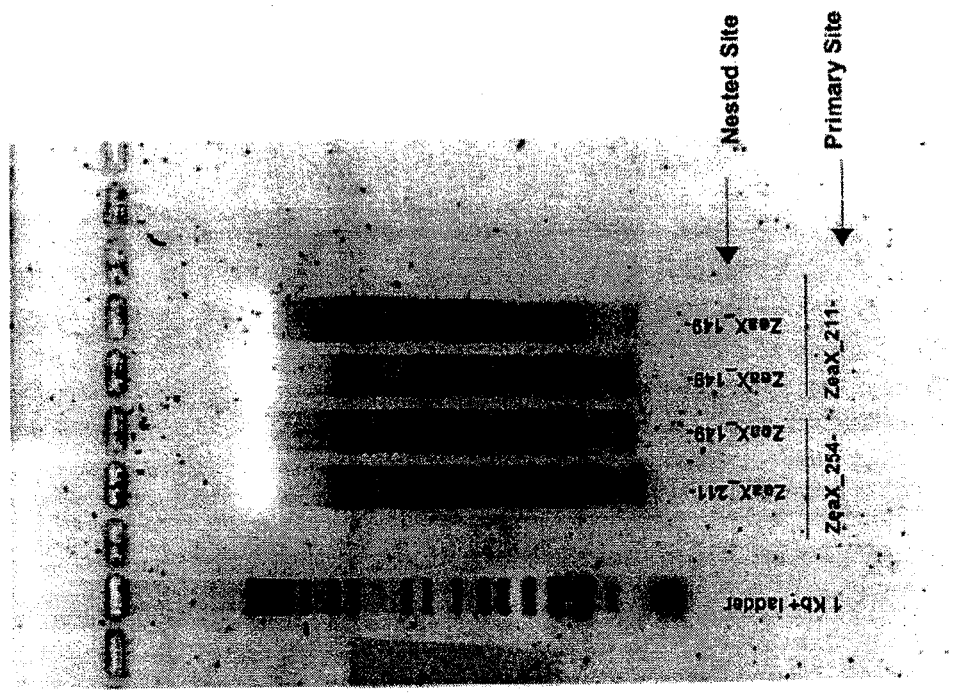
FIG. 16 shows a secondary (nested) amplification of unpublished genomic region located upstream from the Maysine enhancer on chromosome 3 from a corn genomic TRF library prepared by hydrodynamic shearing.

A genomic region of 1,376 bp corresponding to the corn transcriptional regulator gene (Accession # AF136530), which is a homologue to the silk Maysine enhancer, mapped as a single copy gene to the sh2-a1 region on chromosome 3 (United States Department of Agriculture/Agricultural Research Service and University of Missouri Maize Genomic Center Database). The unknown upstream flanking region is amplified with primers Zea X 211– and Zea X 254– in primary PCR™ from the corn TRF library and re-amplified with primers Zea X 211–, Zea X 149–, and Zea X 49– in nested PCR™ (Table I, FIG. 16). Each of the nested PCR™ primers is also used as sequencing primer in three individual cycle sequencing reactions. The average read length from six quality sequencing runs is 583 bases (range 421-703) at a Phred score of >20. Consensus sequence of 782 bp is assembled from the sequencing chromatogram files.

Region 3. MubG1 Upstream Region.

Figure 17:
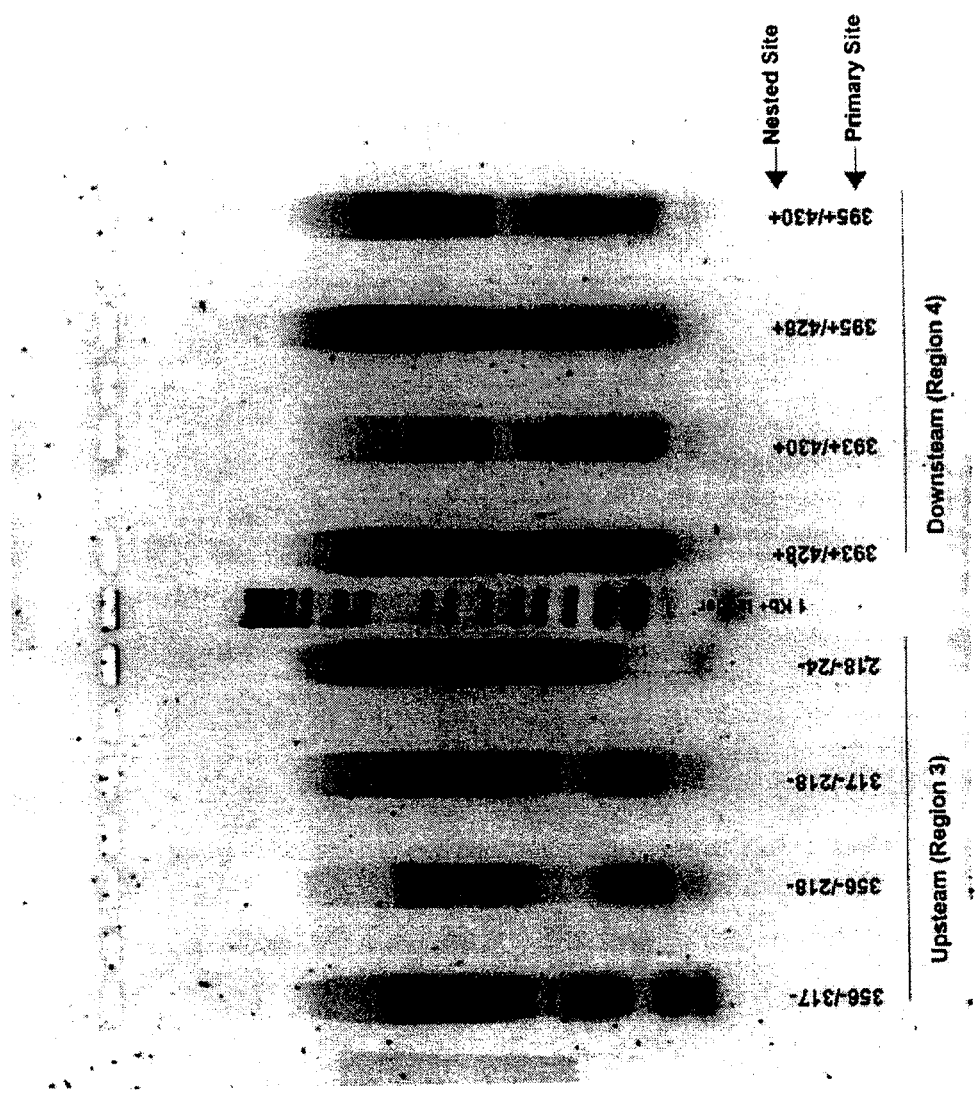
FIG. 17 shows a secondary (nested) amplification of unpublished genomic region flanking the poly-ubiquitin 1 gene (Mub G1) from a corn TRF library prepared by hydrodynamic shearing.

A unique 500 bp sequence from the published MubG1 (Poly-Ubiquitin gene 1) promoter is used to design primers. The unknown flanking region upstream of the promoter is amplified with primers MubG1 218−, MubG1 317−, MubG1 356−, in primary PCR™ from corn TRF library and with primers MubG1 24−, MubG1 218−, MubG1 317−, in nested PCR™ (Table I, FIG. 17). Primers MubG1 218− and MubG1 24− are used with the three amplified templates in three individual cycle sequencing reactions. The average read length from a total of nine runs is 578 bases (range 444-652) at a Phred score of >20. Consensus sequence of 867 bp is assembled from the raw data sequencing chromatogram files.

Region 4. MubG1 Downstream Region.

A unique 500 bp sequence from genomic MubG1 contig located at the 3'-end of the poly-Ubiquitin gene is used to design primers. The unknown flanking downstream region is amplified with primers MubG1 393+ and MubG1 395+ in primary PCR™ from corn TRF library and re-amplified with primers MubG1428+ and MubG1 430+ in nested PCR™ (Table I, FIG. 17). Primers MubG1 428+ and MubG1 430+ are used in sequencing with the two sequencing templates derived from nested PCR™ and in 3 individual cycle sequencing reactions. The first primer failed to produce good quality sequencing ladders. The average read length from the three quality sequencing runs with primer MubG1 430+ is 624 bases (range 616-639) at a Phred score of >20. Consensus sequence of 626 bp is assembled from the sequencing chromatogram files.

Thus, in this example four out of four attempted genomic regions were successfully sequenced. The average read length at a Phred score of >20 is 581 bases. The total high quality sequence generated is 2,971 bases of which 1,350 bases are sequenced de novo and do not match any reference sequences. Out of 1,621 bases of new sequences overlapping reference regions, the total number of mismatches is six. One out of eight sequencing primers did not produce a sequencing ladder of acceptable quality.

Example 8

Preparation of TRF Library from *E. coli* Genomic DNA by Thermal Fragmentation Method This example describes the preparation of the TRF library of average size of 1 Kb from *E. coli* genomic DNA, particularly by DNA hydrolysis at high temperature under neutral conditions and terminal transferase mediated tailing with deoxyguanosine triphosphate.

The prepared library allows reproducible amplification of many nested DNA mixtures using one sequence-specific primer and universal homopolymeric primer $C_{10}$ (containing ten cytosines). Sequencing of these mixtures using the same primer generates 600-800 base reads that are adjacent to chosen kernel primers.

Figure 18:
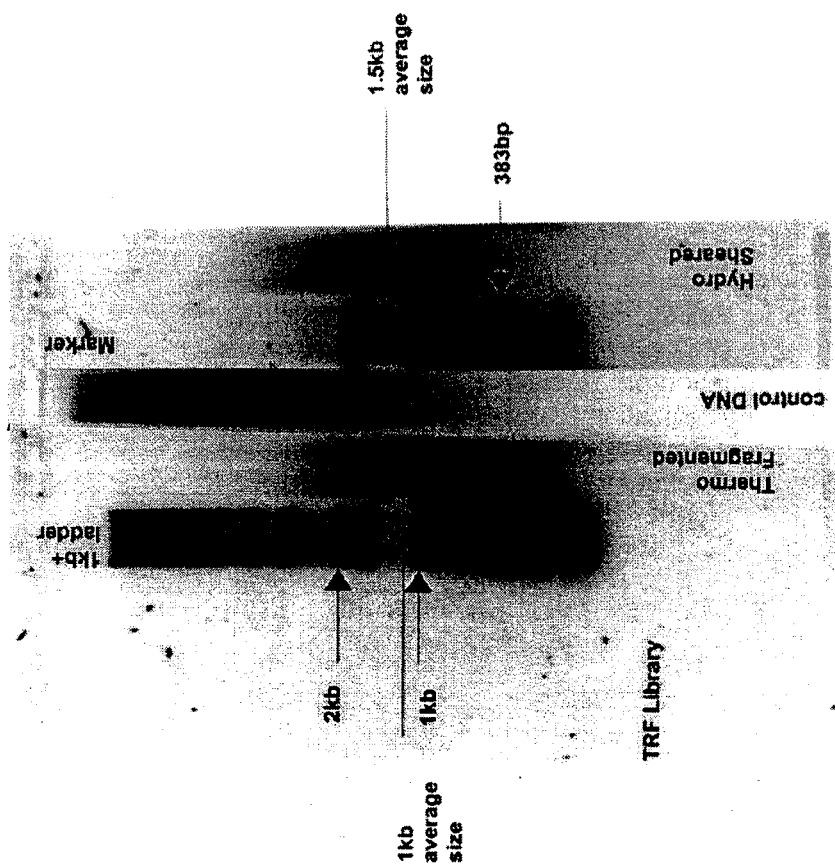
FIG. 18 shows a comparison of the size of DNA molecules before and after fragmentation by the thermal treatment and the hydrodynamic shearing.

DNA is isolated by standard purification from, for example, *E. coli* strain MG1655 and diluted to 200 ng/μl in TE-L buffer (10 mM Tris-HCl, pH 7.5; 0.1 mM EDTA). To thermally fragment the DNA, the sample is incubated at 95° C. for 5 min in Mini Cycler machine (MJ Research) using the heating lid. For comparison, mechanically broken DNA sample is prepared as described in Examples 1, 4 and 6, except that the fragmentation on a HydroShear device (Gene Machines) is achieved by 20 passes at a speed code of 3. The average size of fragmented DNA is then analyzed by electrophoresis on a 1% agarose gel under alkaline conditions. FIG. 18 shows the DNA size distributions after thermal fragmentation and hydrodynamic shearing.

Homopolymeric G tails, consisting of 10 to 15 nucleotides, are enzymatically added to the 3'-termini of the DNA fragments by terminal deoxynucleotidyl transferase. DNA template at 10 ng/μl is incubated with 20 units of New England Biolabs (NEB) terminal transferase in 1×NEB restriction buffer #4 containing 0.25 mM $CoCl_2$, and 20 μM dGTP in a final volume of 100 μl for 15 min at 37° C. The reaction is stopped by adding 10 μl of 0.5 M EDTA, pH 8.0. The sample is supplemented with ⅟₁₀ volume of 3 M sodium acetate, pH 5.0, precipitated with 2.5 volumes of ethanol in the presence of 2 μg glycogen, washed twice with 70% ethanol at room temperature, and dissolved in TE-L buffer.

Example 9

Amplification and Sequencing of *E. coli* DNA Regions with Specific Primers from TRF Library Prepared by Thermal Fragmentation Method Vs. Library Prepared by Hydro-Shearing Method Primers for amplification are designed using Oligo version 6.53 primer analysis software (Molecular Biology Insights, Inc., Cascade, Colo.). Primers are 21 to 23 bases long, having high internal stability, low 3'-end stability, and melting temperatures of 57° C. to 62° C. (at 50 mM salt and 2 mM $MgCl_2$). Primers are designed to meet all standard criteria such as low primer-dimer and hairpin formation and are filtered against an *E. coli* genomic 6-mer frequency database.

Oligonucleotides for PCR™ amplifications are designed to target amplicons of two specific regions of the *E. coli* DNA: primers S3, S6 (Table I).

Figure 19:
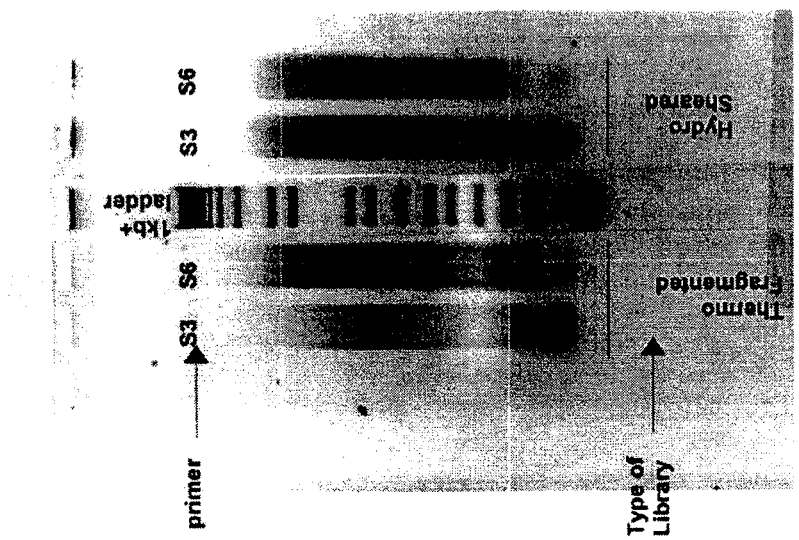
FIG. 19 shows primary amplification of two specific regions of the E. coli genome from TRF libraries prepared by the thermal fragmentation and the hydrodynamic shearing methods.

TD PCR™ amplification is performed with 300 nM specific primer, 300 nM of universal $C_{10}$ primer, and 40 ng of *E. coli* TRF library DNA (described in Example 8) in a final volume of 25 μl under standard Titanium Taq Polymerase conditions (Clontech; Palo Alto, Calif.). After initial denaturing at 95° C. for 2 min, samples are subjected to 20 cycles at 95° C. for 15 sec, 73° C. for 2 min and 15 sec, with decreasing temperature of 0.5° C. in each cycle. The next round of amplification is 25 cycles at 95° C. for 15 sec, 60° C. for 2 min, with increasing time of extension of 1 sec each cycle. Aliquots of 12 μl of each PCR™ reaction are analyzed by electrophoresis on a 1% agarose gel (FIG. 19). As shown, a uniform smear is obtained when TRF library prepared by hydrodynamic shearing is used as the template, whereas a smear with some faint discrete bands is amplified from TRF library prepared by thermal fragmentation.

The PCR™ amplification products are quantified from the stained gel by comparison with standard DNA markers using the volume quantitation tool of Fluor-S Imager software (Bio Rad). The PCR™ products are purified free of primers and nucleotides by the QIAquick PCR™ purification kit (Qiagen), eluted in 30 μl of 1 mM Tris-HCl, pH 7.5 and used as template for cycle sequencing with the same primers used for PCR™.

Cycle sequencing is performed by mixing 2 to 11 μl of sequencing template, containing 40 to 250 ng of total DNA, with 1 ml of 5 μM each sequencing primer and 8 μl of DYEnamic ET terminator reagent mix (Amersham Pharmacia Biotech; Piscataway, N.J.) in 96 well plates in final volume of 20 μl. Amplification is performed for 30 cycles at: 94° C. for 20 sec, 58° C. for 15 sec, and 60° C. for 75 sec. Samples are precipitated with 70% ethanol and analyzed on MegaBACE 1000 capillary electrophoresis sequencing system (Amersham Pharmacia Biotech; Piscataway, N.J.) using the manufacturer's protocol.

Table III shows a comparison of the sequencing results obtained from the two regions of the *E. coli* genome from TRF libraries prepared by thermal fragmentation and hydrodynamic shearing methods. For both libraries, the average read length of the analyzed sequences is above 600 bases. Sequence accuracy as compared to the published *E. coli* K12 MG1655 sequences is equal or greater than 98%.

TABLE III

Comparison of the Sequencing Results for two Regions of the *E. coli* Genome Amplified From Thermally Fragmented and Hydro Sheared TRF Libraries

| Sequenced Region | Read Length at Phred >20 | Accuracy of the Read (% match with published sequence) |
|---|---|---|
| | | TRF-TF Library |
| S3 Region | 671 | 98% |
| S6 Region | 734 | 98% |
| | | TRF-HS Library |
| S3 Region | 700 | 99% |
| S6 Region | 700 | 99% |

This example demonstrates that specific genomic regions can be amplified and sequenced with a high level of accuracy and long read length from a TRF library prepared by thermal fragmentation from bacterial DNA.

Example 10

High Throughput Preparation, Amplification and Sequencing of Multiple TRF DNA Libraries Created by Thermal Fragmentation Method This example describes parallel preparation of multiple TRF libraries from different DNA sources. The proposed protocol is based on the reasonable assumption that preparation of the TRF libraries by thermal fragmentation procedure and terminal transferase mediated G-tailing reaction can be easily scaled up to the 96 or 384 multi-well format.

Figure 20:
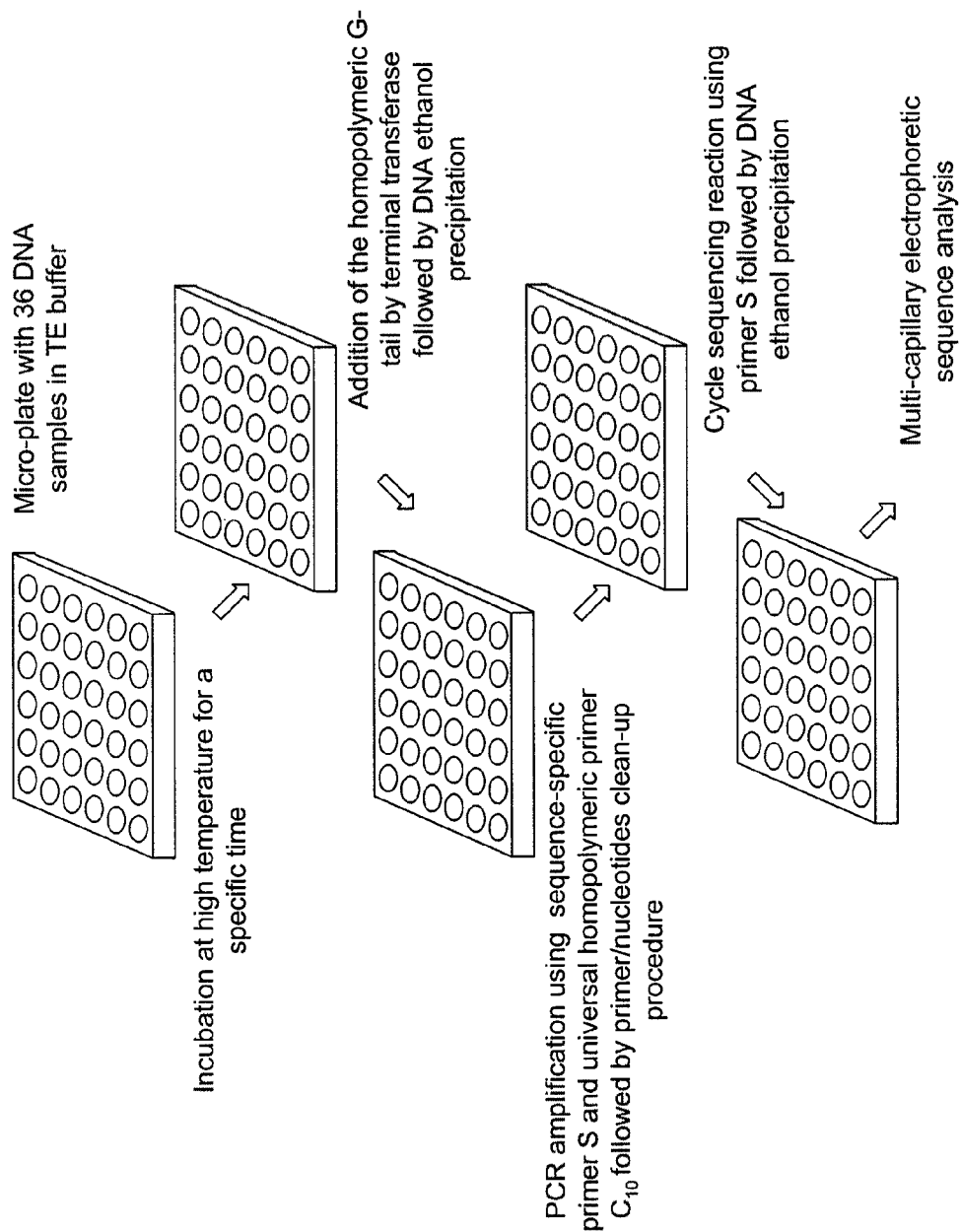
FIG. 20 illustrates high throughput preparation and sequence analysis of multiple DNA samples in the multi-well, micro-plate format.

FIG. 20 shows schematically all steps involved in preparation of the TRF library in the multi-well format. The drawing shows only 36-well plate, but it can be 96, 384, 1536 or larger format.

Important steps involved in the protocol include, for example: 1) preparation of DNA in low salt TE buffer; 2) incubation of DNA at high temperature (for example, 95° C.) for a specific time (for example, 5 min); enzymatic addition of the homopolymeric G-tails to the 3' ends of DNA fragments by terminal transferase; 3) DNA purification by ethanol precipitation or spin-column; 4) PCR™ (nested PCR™) amplification using sequence-specific primer(s) S($S_N$) and universal homopolymeric primer $C_{10}$; 5) primers and nucleotides removal; 6) cycle sequencing using sequence-specific primer S or $S_N$; 7) DNA purification by ethanol precipitation or spin-column; and/or 8) analysis of the DNA samples by the 96-capillary DNA sequencing device.

Example 11

Thermal Fragmentation of DNA Under Different Buffer and Salt Conditions

This example illustrates the efficiency of DNA thermal fragmentation at low salt conditions and demonstrates the inhibitory effect of monovalent and divalent cations on the DNA degradation during incubation at high temperature.

DNA was isolated by standard purification from *E. coli* strain MG1655, ethanol precipitated, washed with 70% ethanol and dissolved in TE buffer at a concentration of 100 µg/ml. One µg DNA aliquots were ethanol-precipitated in the presence of 2 µg glycogen (Roche), centrifuged for 30 min at 16,000×g, washed twice with 70% ethanol at room temperature and then dissolved in 10 µl of the following solutions: ultra pure distilled water ("GIBCO"); TE buffer (10 mM Tris-HCL, 1 mM EDTA, pH 7.5); TE buffer diluted 20 times (500 µM Tris-HCL, 50 µM EDTA, pH 7.5); TE buffer supplemented with 10 mM $MgCl_2$; 1 mM EDTA alone, pH 8.0; 100 mM EDTA alone, pH 8.0; 10 mM Tris-HCl alone, pH 7.5; 1 M Tris-HCl, pH 7.5; 1× NEBuffer 4 (New England Biolabs; Beverly, Mass.) containing 50 mM potassium acetate, 20 mM Tris-acetate, 10 mM magnesium acetate, 1 mM dithiothreitol, pH 7.9; or 1× NEBuffer 4 supplemented with 250 µM $CoCl_2$; 1×PCR buffer (Clontech) containing 40 mM Tricine KOH, 16 mM KCl 3.5 mM $MgCl_2$ 3 ng/µl BSA, pH 8.0. DNA samples were subjected to thermo-fragmentation in a MJ Research PTC-150 MiniCycler with heating lid. Samples were incubated at 95° C. for the indicated times and then analyzed by alkaline agarose gel. Electrophoresis was performed in 1% agarose (Maniatis et al., 1989) with 40 mM NaOH and 1 mM EDTA as a buffer. The gel was run at 1V/cm (240-280 mA) for 16 hr at room temperature with buffer circulation. After electrophoresis, the gel was neutralized, stained with SYBR Gold (Molecular Probes), and analyzed using Bio-Rad Fluor S Imager.

FIG. 21A shows the kinetics of thermal fragmentation of DNA in two low salt buffers and water. The data show that high molecular weight DNA (FIG. 21A, lane 2) can be converted into 1-2 kb fragments within minutes of exposure at 95° C. Longer times (up to 30 min) of heat treatment (FIG. 21A, lanes 8, 14, and 21) leads to reduction of the average size of DNA down to 100 bases. The rate of thermal fragmentation in water (FIG. 21A, lanes 3-8) and diluted TE buffer (FIG. 21A, lanes 9-14) is higher than in TE buffer (FIG. 21A, lanes 16-21).

The inhibitory effect of different salts and buffers on thermal fragmentation of DNA is shown on FIG. 11B for the constant time of incubation (30 min). Incubation of DNA at 95° C. in 1 M Tris-HCl (FIG. 21B, lane 7), 100 mM EDTA (FIG. 21B, lane 8), PCR buffer (FIG. 21B, lane 10) and NEBuffer 4 (FIG. 21B, lane 12) results in a mild change of the original size of DNA (FIG. 21B, lane 3). In contrast, incubation of DNA at 95° C. in low salt buffers such as TE (FIG. 21B, lane 2), $H_2O$ (FIG. 21B, lane 4), 10 mM Tris-HCl (FIG. 21B, lane 5) and 1 mM EDTA (FIG. 21B, lane 6) produces DNA fragments smaller than 1,000 bases. Addition of 10 mM $MgCl_2$ to TE buffer (FIG. 21B, lane 9) also causes a strong inhibition of DNA thermal degradation (compare with FIG. 21B, lane 2). Addition of $Co^{++}$ ions to NEBuffer 4 has no effect on the rate of thermo-fragmentation (FIG. 21B, lane 11).

Thus, this example demonstrates that DNA can be fragmented very efficiently at neutral pH by thermal treatment at 95° C. The size of fragmented DNA can be controlled by time and buffer/salt concentration. The presence of $Mg^{2+}$ ions also prevents degradation of DNA.

Example 12

Mechanism of Heat-Induced DNA Fragmentation at Neutral pH

This example shows that thermal fragmentation occurs predominantly at purine bases, suggesting a two-step mechanism that is initiated by heat-induced hydrolysis of glycosyl bond with the release of purine bases and followed by a heat-induced breakage of DNA molecule at the apurinic sites.

Two pyrimidine-rich oligonucleotides, 29 residues long, with a fluorescein group at the 5' end, amino-modifier group at the 3' end, and only one purine base in the middle, were synthesized: oligonucleotides OL1 (SEQ ID NO:29) and OL2 (SEQ ID NO:30) with dG and dA bases in position 19, respectively (Table IV).

TABLE IV

Oligonucleotides used for experiments described in Examples 12 and 14-18.

| Oligo-nucleotide ID[a] | Sequence (5'-3') |
|---|---|
| 1. OL1 | 5' 6-FAM ™[b]-TCT CCT TCC TCC TTT CTC GCT TCT CTC CT-3'AmMod C7[c] |
| 2. OL2 | 5' 6-FAM ™-TCT CCT TCC TCC TTT CTC ACT TCT CTC CT-3'AmMod C7 |
| 3. OL3 | 5' 6-FAM ™-TCT CCT TCC TCC TTT CTC GCT TCT CTC CT |
| 4. OL4 | 5' 6-FAM ™-TCT CCT TCC TC-3'AmMod C7 |
| 5. OL5 | 5' 6-FAM ™-TCT CCT TCC TC |
| 6. OL6 | 5' 6-FAM ™-TCT CCT TCC T |
| 7. OL7 | 5' 6-FAM ™-TCT CCT TCC TC-3'ddC[d] | a) All oligonucleotides are synthesized and purified commercially
b) 5' 6-FAM ™-6-carboxyfluorescein
c) 3'AmMod C7-3'-amino-modifier; it eliminates the native 3'-OH group from the oligonucleotide, which functionally blocks this oligo from participating as a primer in DNA synthesis
3'ddC-dideoxy-C is a 3' chain terminator that prevents 3' extension by polymerases Ten pmol of these oligonucleotides were diluted in 10 µl of water (GIBCO) and then subjected to thermo-fragmentation in a MJ Research MiniCycler with heating lid. Samples were incubated at 95° C. over a time course and then analyzed on 15% denaturing polyacrylamide TBE-Urea gels (Invitrogen/Novex) (FIG. 22). The gels were run at 180 V for 45 min at constant temperature (55° C.) in a Red Roller hybridization oven (Hoefer). After electrophoresis, the gels were analyzed using Bio-Rad Fluor S Imager with Fluorescein filter and Quantity One software.

FIG. 22A shows the kinetics of thermal fragmentation of the oligonucleotide OL1 with G base. After 20 minutes of incubation at 95° C., two distinct bands can be seen on the gel, and they reach equal intensity at 40 min of incubation. The upper band is unbroken fluorescein-labeled oligonucleotide, and the lower band corresponds to fluorescein-labeled 19-mer created as a result of cleavage at the dG site. After one hour of thermal treatment at 95° C., more than 50% of oligo is converted into the 19 base product, and smaller fragments appeared, indicating that chain breakage occurs not only at the dG site, but at dC and dT bases, although with much lower rate. After 110 min of exposure at 95° C., almost all original molecules are hydrolyzed and converted into 19 base and shorter products.

The kinetics of thermal fragmentation of the oligonucleotide OL2 with the purine base A is shown on FIG. 22B. It proceeds in a similar way as for oligonucleotide OL1 but with a somewhat slower rate. In this case the first product of thermo-hydrolysis appears only after 30 min of incubation at 95° C., and the bands become equal in intensity after 50 min.

Previous studies described several types of lesions introduced into DNA by heat: DNA strand breaks, apurination, guanine oxidation and deamination of cytosine. The data provided herein clearly show that heat-induced strand breaks at neutral pH occur predominantly at purinic bases, and they are most likely the result of heat-induced apurinization in DNA.

Example 13

TdT Tailing of DNA After Thermal Fragmentation

This example demonstrates the availability of DNA termini, particularly 3' ends generated after thermal fragmentation, to enzymatic tailing by terminal transferase.

DNA was isolated by standard purification from fresh human lymphocytes, ethanol precipitated and dissolved in TE buffer at concentration 100 ng/µl.

Five µg DNA aliquots were subjected to thermo-fragmentation in a MJ Research MiniCycler with heating lid. Samples were incubated at 95° C. for 5 minutes followed by additional heat treatment at the same temperature for 10 minutes in NEBuffer 4 containing 10 mM magnesium acetate. This step was introduced with the anticipation that second heating in the presence of $Mg^{2+}$ ions would stimulate chain breaks at apurinic sites left after the first heating step (at low salt) without noticeable creation (and breakage) of any new abasic sites (Lindahl and Andersson, 1972). This was confirmed by experiments on a model oligonucleotide system. The reaction products were electrophoresed through a 1% agarose alkaline gel, stained with SYBR Gold, and the bands representing the size around 1 kb were excised from the gel. The molecules were extracted from the gel by using a DNA extraction kit (Ultrafree-DA (Millipore)) and then ethanol precipitated. Next, the homopolymeric dG tail, dA tail, and mixed dG and dA tail were enzymatically added to the 3'-termini of the DNA fragments by terminal deoxynucleotidyl transferase. DNA templates at 100 ng/µl were incubated with 10 units of terminal transferase (NEB) in 1× NEBuffer 4 containing 0.25 mM $CoCl_2$ and 100 µM dGTP or 100 µM dATP or a mixture of 100 µM dGTP and 100 µM dATP in a final volume of 20 µl for 20 min at 37° C. The reaction was stopped by adding 2 µl of 0.5 M EDTA, pH 8.0. Samples were ethanol-precipitated and then analyzed on 6% denaturing polyacrylamide TBE-Urea gels (Invitrogen/Novex). The gels were run at 180 V for 45 min at the constant temperature 55° C. in a Red Roller hybridization oven (Hoefer). After electrophoresis gels were stained with SYBR GOLD and analyzed using Bio-Rad Fluor S Imager.

Figure 23:
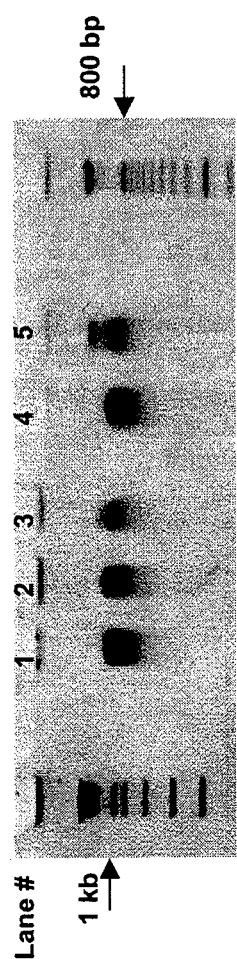
FIG. 23 demonstrates efficiency and peculiarity of TdT-mediated tailing reaction when the substrate is thermally fragmented and size-fractionated human DNA.

Results of the tailing of DNA fragments produced by thermo-fragmentation are presented on FIG. 23. Lanes 1 and 4 show the original 1 kb DNA size fraction after thermo-fragmentation. Lanes 2, 3 and 5 show the same DNA after incubation with terminal transferase and dGTP, dATP and dGTP/dATP mix, respectively. About 30% of heat-induced 3' DNA ends are tailed with dGTP/dATP mix (FIG. 23, lane 5). No tailing can be seen for dGTP and dATP nucleotides.

Example 14

Homopolymer Tailing Reaction Catalyzed by Terminal Transferase on Thermally Fragmented Oligonucleotide Template This example characterizes TdT-mediated tailing efficiency of oligonucleotide termini produced by thermo-fragmentation process and describes a novel 3' end repair function of the terminal transferase enzyme.

Figure 24:
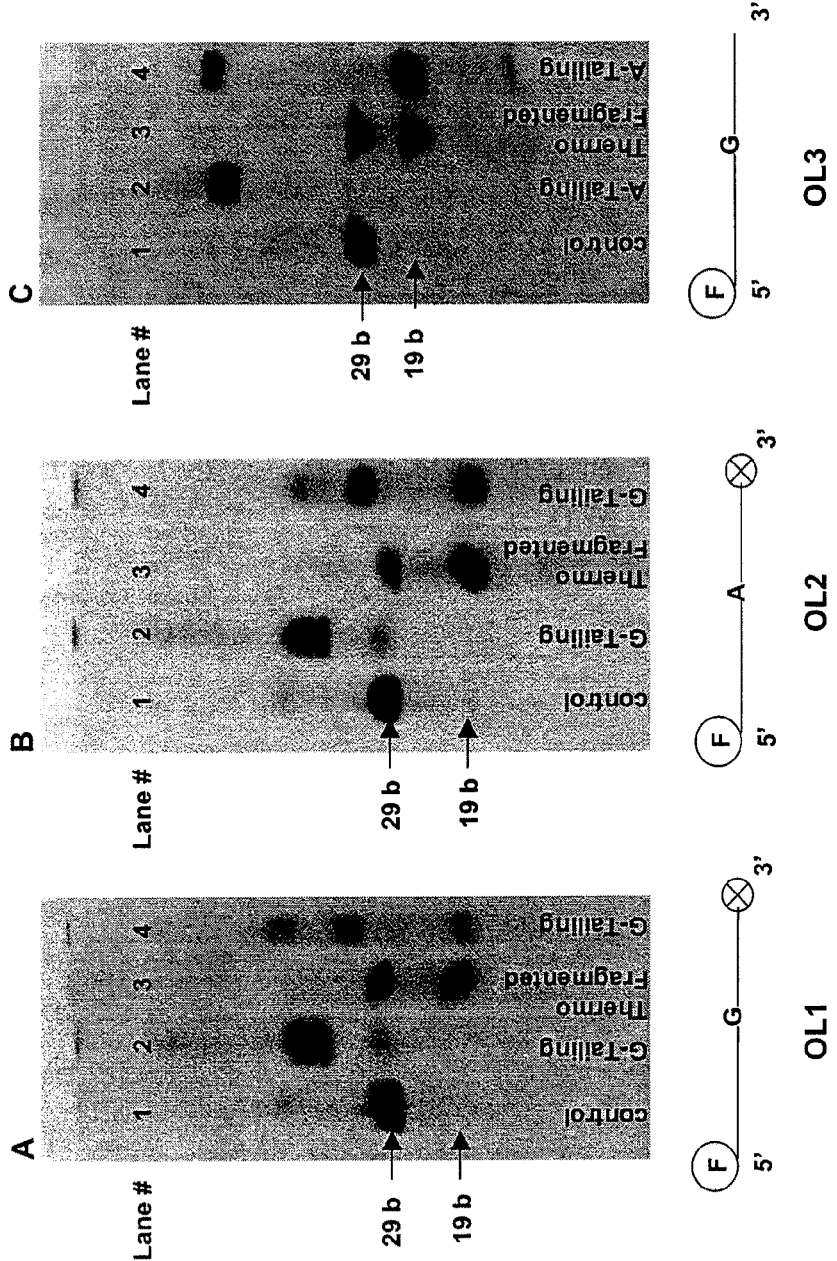
FIG. 24A demonstrates efficiency of TdT-mediated dGTP tailing reaction when the substrates are thermally fragmented and intact 5' fluorescein-labeled oligonucleotide with a single guanine base and blocking AmMod C7 group at the 3' end.
FIG. 24B demonstrates efficiency of TdT-mediated dGTP tailing reaction when the substrates are thermally fragmented and intact 5' fluorescein-labeled oligonucleotide with a single adenine base and blocking AmMod C7 group at the 3' end.
FIG. 24C demonstrates efficiency of TdT-mediated dATP tailing reaction when the substrates are thermally fragmented and intact 5' fluorescein-labeled oligonucleotide with a single guanine base and native 3'-OH group.

Three pyrimidine-rich oligonucleotides, 29 residues long, with a fluorescein group at the 5' end were used. Oligonucleotides OL1 and OL2 were synthesized with blocking group Amino Modifier C7 at the 3' end and one purine base (dG or dA, respectively) in the middle (Table IV; see also Example 12). Oligonucleotide OL3 (SEQ ID NO:31) is similar to oligonucleotide OL1 but has a 3'-OH group. Ten pmol of the oligonucleotide OL1, OL2 or OL3 was diluted in 10 µl of water (GIBCO) and then subjected to thermo-fragmentation at 95° C. for 50 minutes in a MJ Research MiniCycler with heating lid. Products of thermo-fragmentation and non-heated oligonucleotides OL1, OL2 or OL3 were tailed by terminal deoxynucleotidyl transferase (TdT). Ten pmol of these oligonucleotides were incubated with 10 units of terminal transferase (NEB) in 1× NEBuffer 4 containing 0.25 mM $CoCl_2$ and 100 µM dGTP (FIGS. 24A and 24B) or dATP (FIG. 24C) in a final volume of 50 µl for 20 mM at 37° C. The reaction was stopped by adding 5 µl of 0.5 M EDTA, pH 8.0. Samples were ethanol-precipitated and then analyzed on a denaturing 15% polyacrylamide TBE-Urea gel (Invitrogen/Novex) (FIG. 24). The gels were run at 180 V for 45 mM at the constant temperature 55° C. in the Red Roller hybridization oven (Hoefer). After electrophoresis, gels were analyzed using Bio-Rad Fluor S Imager with Fluorescein filter and Quantity One software.

Surprisingly, despite the presence of a 3' AmMod C7 group, which functionally should block oligonucleotides from participating as a primer in DNA synthesis, both oligonucleotides OL1 and OL2 are tailed efficiently with dGTP, and almost 100% of molecules receive G-tails and change their mobility (FIGS. 24A and 24B). The 19-mer products of thermo-fragmentation are also tailed but not completely. About 50% of these products are competent for G-tailing and change their mobility (FIGS. 24A and 24B). At the same time, the 19-mer product of thermo-fragmentation of oligonucleotide OL3 shows no tailing in the presence of dATP.

It is known that fragmentation via depurination produces DNA fragments with enzymatically non-competent 3' ends (Kotaka and Baldwin, 1964; Lindahl and Andersson, 1972). The data presented in this Example demonstrate a new function of terminal transferase, specifically, the ability to process ends lacking 3' hydroxyl group. It is shown that in the presence of dGTP, TdT is able to tail a significant fraction (50%) of ends resulted after break at the apurinic site and almost all ends terminated with Amino Modifier C7, suggesting a novel 3' end repair function of the terminal transferase enzyme. The absence of tailing in the presence of dATP suggests a special role for deoxyguanine triphosphate in the repair process catalyzed by TdT.

Example 15

TdT-Mediated Tailing of Blocked and Normal Oligonucleotide Templates: Effect of dGTP Concentration This example compares tailing reactions catalyzed by terminal transferase in the presence of different concentrations of dGTP on 3' blocked and non-blocked model oligonucleotide templates. The titration of dGTP concentration was necessary to define the working concentration for oligonucleotide template.

Two pyrimidine-rich oligonucleotides OL1 and OL3, each 29 residues long with a fluorescein group at the 5' end, were used. Oligonucleotide OL1 has the blocking Amino Modifier C7 group and oligonucleotide OL3 the hydroxyl group at the 3' end (Table IV). Ten pmol of these oligonucleotides were subjected to a tailing reaction in the presence of different dGTP concentrations. Blocked and unblocked oligonucleotides were incubated with 10 units of terminal transferase (NEB) at 3TC (20 min) in 1× NEBuffer 4 containing 0.25 mM $CoCl_2$ and the concentration of dGTP varying from 10 µM to 100 µM in a final volume of 50 µl. One-fifth of the volume of the reaction mixture was analyzed on the 15% denaturing polyacrylamide TBE-Urea gels (Invitrogen/Novex) (FIG. 25). The gels were run at 180 V at a constant temperature of 55° C. in the Red Roller hybridization oven (Hoefer). After electrophoresis, gels were analyzed using Bio-Rad Fluor S Imager with Fluorescein filter and Quantity One software.

The experiment shows that complete tailing of the oligonucleotide with 3' OH group occurs at 10 µM dGTP (FIG. 25B). At a similar concentration of dGTP, the oligonucleotide with 3' blocking group shows no detectable tailing (FIG. 25A). For blocked 3' ends, tailing becomes visible at 20 µM dGTP and reaches its maximum (more than 90%) at 100 µM dGTP (FIG. 25A).

These data provide additional evidence that dGTP is required for repair activity of terminal transferase and show that only high concentration (50 µM and above) of this nucleotide activates TdT-mediated repair of blocked 3' ends.

The results of Example 5 are important for defining conditions for the G-tailing of DNA fragments produced by different physical and chemical methods that usually have "bad" 3' ends. In particular, it provides (in combination with Example 14 and Example 16) reasonable explanation why thermo-fragmented DNA can be efficiently tailed with dGTP/dATP mix but not with dATP in the Example 13.

Example 16

Special Role of dGTP Nucleotide in Tailing Reaction Catalyzed by Terminal Transferase on 3' End Blocked Templates This example demonstrates a unique role of the nucleotide dGTP in its ability to process the 3' end of an oligonucleotide with 3' Amino C7 blocking.

In this example, four oligonucleotides were used: oligonucleotides OL1 and OL4 (SEQ ID NO:32) with a fluorescein group at the 5' end and with a blocking group Amino Modifier C7 at the 3' end; oligonucleotide OL5 (SEQ ID NO:33) with a fluorescein group at the 5' end and with an OH group at the 3' end; and oligonucleotide OL7 with a fluorescein group at the 5' end and with a dideoxy C (ddC) blocking group at the 3' end (Table IV). Tailing reactions were performed using 10 µmol of an oligonucleotide and 10 units of terminal transferase (NEB) in 1× NEBuffer 4 containing 0.25 mM $CoCl_2$, 50 µM of dXTP (where X is G, A, T or C) in a final volume of 50 µl for 20 min at 37° C. The reaction was stopped by adding 5 µl of 0.5 M EDTA, pH 8.0. Samples were ethanol-precipitated and then separated on a denaturing 15% polyacrylamide TBE-Urea gel. After electrophoresis, the gel was analyzed using Bio-Rad Fluor S Imager with Fluorescein filter and Quantity One software.

FIG. 26A shows TdT-mediated repair/tailing of the AmMod C7 blocked oligonucleotide OL1 with different nucleotide-triphospates. The effect of tailing is only observed with dGTP (FIG. 26, lane 1 vs. lane 5), while other nucleotides have no effect (FIG. 26, lane 1 vs. lanes 2, 3, 4).

FIG. 26B shows TdT-mediated repair/tailing of another Amino C7 blocked oligonucleotide OL4 in the presence of dGTP (FIG. 26B, lane 1 and lane 4). Interestingly, terminal transferase is unable to repair and tail the oligonucleotide OL7 (SEQ ID NO:35) with dideoxy C (ddC) blocking group at the 3' end (FIG. 26B, lane 3 and lane 6). Control terminal transferase tailing of non-blocked oligonucleotide OL5 with dGTP is shown on the FIG. 26B (lanes 2 and 5).

Obviously, dGTP plays a dual role in the tailing mechanism catalyzed by terminal transferase on the 3' end blocked DNA substrates. First, it serves as a cofactor that induces end repair process that eliminates terminal blocked nucleotide (s), and, second, it serves as a substrate for tailing reaction. dGTP-induced repair activity of terminal transferase is a novel property that has not previously been described.

Example 17

Mechanism of the 3' End Repair Activity of Terminal Transferase

This example shows that terminal transferase elongates 3' end blocked templates by removing one or two nucleotides from the 3' end and then adding homopolymeric G-tail. Because dGTP tailing at nucleotide concentration 50-100 µM (concentration necessary for TdT repair activity; see Example 15) creates homopolymeric dG tails 25-35 residues long, riboGTP is utilized in these experiments. Ribo NTPs can be incorporated into DNA ends by terminal transferase as efficiently as their deoxy analogues with the only difference that the number of incorporated ribo-bases is limited to 1-5 nucleotides (Boule et al., 2001). The experiment described below confirms the underlying assumption that ribo GTP can play the same repair activation role as dGTP does.

Three 5' fluorescein-labeled oligonucleotides were tailed using TdT and ribo GTP: oligonucleotides OL4, 11 residues long, with Amino C7 blocking group at the 3' end; oligonucleotide OL5, 11 residues long, with a similar sequence but no blocking group at the 3' end; and oligonucleotide OL6 (SEQ ID NO:34), 10 residues long (Table IV). In one reaction set, 5 µmol of oligonucleotides OL4, OL5, and OL6 were incubated with 10 units of terminal transferase (NEB) in 1× NEBuffer 4 containing 0.25 mM $CoCl_2$ and 100 µM ribo GTP. In another reaction set, 5 µmol of the oligonucleotides OL5 was incubated with 10 units of terminal transferase (NEB) in 1× NEBuffer 4 containing 0.25 mM $CoCl_2$ and four different concentrations of ribo GTP (1, 5, 20 µM) in a final volume of 20 µl for 20 min at 37° C. The reaction was stopped by adding 2 µl of 0.5 M EDTA, pH 8.0. Samples were ethanol precipitated and then separated on denaturing 15% polyacrylamide TBE-Urea gel. After electrophoresis, the gel was analyzed using Bio-Rad Fluor S Imager with Fluorescein filter and Quantity One software.

FIG. 27 shows that terminal transferase indeed repairs and adds ribo GTP nucleotides to the 3' end of Amino C7 blocked oligonucleotide OL4. Lane 1 and 2 show the oligonucleotide OL4 before and after ribo G-tailing, respectively. To determine the number of nucleotides removed by TdT before adding a G-tail we made the comparison of lengths of the ribo G-tailing products of blocked oligonucleotide OL4 (FIG. 27, lane 2) with lengths of the ribo G-tailing products of control oligonucleotide OL5 (11-mer) (FIG. 27, lanes 4,8.9 and 10) and oligonucleotide OL6 (10-mer) (FIG. 27, lane 6). Lane 7 represents the equimolar mixture of tailed oligo samples loaded on lanes 8, 9 and 10. Because ribo G-tailed products of the oligonucleotide OL4 migrate on the gel faster than corresponding products of the 10-mer oligonucleotide OL6 (compare lane 2 and lane 6) it is concluded that about 1 to 3 bases are removed by 3' exonuclease activity of terminal transferase from the end of the oligonucleotide OL4 before adding the tail.

Example 18

Length-Controlled Tailing by Terminal Transferase Using riboGTP/dGTP mixtures

This example demonstrates that terminal transferase can be used for addition of 2-10 guanine bases to the 3' ends of oligonucleotides, suggesting a controlled TdT-mediated repair/tailing procedure for preparing TRF library.

Oligonucleotide OL5, 11 residues long, with a fluorescein group at the 5' end (Table IV) was tailed with terminal transferase at different riboGTP/dGTP ratios in the presence and absence of thermally fragmented DNA. Five pmol of this oligonucleotide and 100 ng of thermally fragmented DNA or just 5 µmol oligonucleotide were incubated with 10 units of terminal transferase (NEB) in 1× NEBuffer 4 containing 0.25 mM $CoCl_2$, 100 µM riboGTP and varying concentrations of dGTP (0, 10, 20 and 50 µM) in a final volume of 20 µl for 20 min at 37° C. The reaction was stopped by adding 2 µl of 0.5 M EDTA, pH 8.0. Samples were ethanol-precipitated and then separated on a denaturing 15% polyacrylamide TBE-Urea gel. After electrophoresis, the gel was analyzed using Bio-Rad Fluor S Imager with Fluorescein filter and Quantity One software.

FIG. 28 shows the result of TdT tailing with riboGTP/dGTP mixtures. Lane 2 shows the mobility of non-processed oligonucleotide OL5. Incubation of the oligonucleotide OL5 with TdT and 100 µM riboGTP produces tails of 3-4 G bases (FIG. 28, lane 1). Addition of dGTP at 10, 20 or 50 µM concentration results in homopolymeric tails containing in average 6, 8 or 10 mixed riboG/dG residues, respectively (FIG. 28, lanes 3, 5, 7). The presence of thermally fragmented genomic DNA slightly reduced average length of tails (FIG. 28, lanes 4, 6, 8). Taking into account the fact that both dGTP and riboGTP stimulate the 3' exonuclease activity of the terminal transferase at high nucleotide concentration (Examples 14-17), it is reasonable to speculate that similar tails are added to 3' ends of genomic DNA.

Thus, this example provides a guideline for controlled C-tailing of DNA fragments produced by thermo-fragmentation, mechanical shearing or any other means that result in DNA ends lacking 3' hydroxyl group.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

PATENTS

U.S. Pat. No. 4,942,124
U.S. Pat. No. 4,683,194
U.S. Pat. No. 4,710,465
U.S. Pat. No. 5,075,216
U.S. Pat. No. 5,143,854
U.S. Pat. No. 5,149,625
U.S. Pat. No. 5,424,186
U.S. Pat. No. 5,366,877
U.S. Pat. No. 5,547,861
U.S. Pat. No. 5,578,832
U.S. Pat. No. 5,599,668
U.S. Pat. No. 5,610,287
U.S. Pat. No. 5,837,832

U.S. Pat. No. 5,837,860
U.S. Pat. No. 5,843,651
U.S. Pat. No. 5,861,242
U.S. Pat. No. 6,027,913
U.S. Pat. No. 6,045,994
U.S. Pat. No. 6,107,023
U.S. Pat. No. 6,114,149
U.S. Pat. No. 6,124,120
U.S. Pat. No. 6,197,557
EP 0 655 506 B1
Japanese Patent No. JP8173164A2
WO 88/10315
WO 89/06700
WO 90/14148
WO 96/21144
WO 98/1112
WO 98/15644
WO 00/18960

PUBLICATIONS

Ardrey, Electrospray Mass Spectrometry, Spectroscopy Europe, 4, 10-18, 1992.
Arnold, C. and I. J. Hodgson. 1991. Vec-torette PCR: a novel approach to genomic walking. PCR Methods Appl. 1:39-42.
Ausubel et al., CURRENT PROTOCOLS IN MOLECULAR BIOLOGY, 1987.
Bankier, A. T., in Methods in Molecular Biology, 23: DNA sequencing protocols; pp 47-50. Edited by: H. and A. Griffin; copyright 1993 Humana Press Inc., Totowa, N. J.
Berg et al. in Automated DNA sequencing and analysis by Adams, Fields, and Venter. Academic Press (1994).
Berkenkamp et al., Science, 281:260-2, 1998.
Bodenteich et al., in Automated DNA sequencing and analysis. Edited by M. Adams, C. Fields and J. C. Venter; Academic Press, 1994, pp. 42-50.
Boule J.-B., Rougeon, F., and Papanicolaou, C., J. Biol. Chem., 276: 31388-31393, 2001
Branum et al., J Am Chem Soc, 123: 1898-1904, 2001.
Brown, D. M., and Todd, A. R., in The Nucleic Acids, Vol. 1, edited by: Chargaff, E., and Davidson, J. N., New York, N. Y., Academic Press, p 444, 1955.
Cantor and Smith Genomics, John Wiley & Sons, Inc., N. Y., 1999.
Cheng, S. et al. (1994) Nature, 369, 684-685. long range PCR
Cormack and Somssich Gene 194 (1997) 273-276
Crain, Mass Spectrometry Reviews, 9: 505-554, 1990.
Devon, R. S., Porteous, D. J., and Brookes, A. J. (1995) Nucleic Acids Res. 23, 1664-1645.
Dieffenbach and Dveksler. PCR Primer CSHL Press 1995.
Eigner, J., Boedtker, H., and Michaels, G., Biochim. Biophys. Acta, 51: 165-168, 1961.
Fenn et al., J. Phys. Chem. 88, 4451-59, 1984.
Fodor, et al., Nature; 364(6437):555-6, 1995.
Forster, Ann. Phys., 2:55-75, 1948.
Franklin, Curr Opin Chem Biol, 5: 201-208, 2001
Freifelder, et al. Anal Biochem, 123(1):83-5, 1982
Frohman, In: PCR Protocols: A Guide To Methods And Applications, Academic Press, N. Y., 1990.
Gingrich et al., BioTechniques, 21: 99-104, 1996
Grant, et al. Biochemistry, 35(38):12313-9, 1996.
Greer, S., Zamenhov, S., J. Mol. Biol., 4: 123-141, 1962.
Grosse, F., and Maims, A., in Methods in Molecular Biology, Vol. 16: Enzymes of Molecular Biology, edited by: Burrell, M. M., p 95, Humana Press Inc., Totowa, N. J., 1993.
Guilfoyle, et al. Nucleic Acids Research 25:1854-1858 (1997).
Hacia, et al., Nature Genet., 14:441-449, 1996.
Hagiwara, K. and Harris Nucleic Acids Research 24:2460-2461 (1996).
Harrison, et al., BioTechniques 22:650-653 (1997).
Hayes et al., Methods Enzymol, 186: 545-549, 1990.
Higuchi et al., Biotechnology 10:413-417 1992.
Hillenkamp, et al., Anal Chem., 63(24):1193A-1203A, 1991.
Holmstrom et al., Anal. Biochem. 209:278-283, 1993.
Hui, E. K., Wang, P. C., and Lo, S. J., Cell Mol. Life Sci. 54: 1403-1411, 1998.
Hunkapiller, et al., Science, 254(5028):59-67. 1991.
Innis, et al., PCR Protocols, Academic Press, Inc., San Diego, 1990.
Jones, D. H. and S. C. Winistorfer, BioTechniques 15:894-904, 1993.
Jones, D. H. and S. C. Winistorfer, Nucleic Acids Res. 20:595-600, 1992.
Komiyama and Sumaoka, Curr Opin Chem Biol, 2: 751-757, 1998.
Koster et al. Biomedical Environmental Mass Spectrometry, 14: 111-116, 1987.
Kotaka, T., and Baldwin, R. L., J. Biol. Chem., 9: 323, 1964.
Kwoh, et al., Proc Natl Acad Sci USA. 1986(4):1173-7, 1989.
Lee, et al., Nuc. Acids Res. 21, 3761-3766, 1993.
Liao et al, Analytical Biochemistry, 253:137-139, (1997).
Lin, et al., Analytical Biochemistry 231:449-452, 1995.
Lindahl, T, Nyberg, B., Biochemistry, 11: 3610-3618, 1972.
Lindahl, T, Andersson, A., Biochemistry, 11: 3618-3623, 1972.
Liu, Y. G., and Whittier, R. F., Genomics 25: 674-681, 1995.
Lukyanov et al. Nucleic Acids Research 24:2194-2195 (1996).
Macrae and Brenner (1994) Genomics 24:176-178
Makarov, et al., 1997
Maniatis T, Fritsch E F and Sambrook J. (1989). Molecular cloning: A laboratory manual. Cold Spring Harbour Laboratory: Cold Spring Harbour, N.Y.
McCombie et al. Methods: Companion Methods Enzymology 3:33-40 (1991). Methods in Enzymology, Vol. 193: "Mass Spectrometry" (McCloskey, ed.), Academic Press, New York, 1990.
Meyer, et al. Nature, 278(5702):365-7, 1979.
Nakamaye et al. Nucleic Acids Research 16:9947 (1988)
Newton, et al. Nucl. Acids Res. 21:1155-1162, 1993.
Nonisotopic DNA Probe Techniques, Academic Press, Inc., pgs. 311-352, 1992.
Ochman et al. Genetics 120:621-623 (1988).
Oefner et al., Nucleic Acid Research, 24: 3879-3886, 1996
Ohara et al., Proc. Natl. Acad. Sci. USA, 86:5673-5677, 1989.
Padegimas et al. Analytical Biochemistry, 260, 149-153, 1998.
Pease et al., Proc. Natl. Acad. Sci. USA, 91:5022-5026, 1994.
Price and Tullius, Methods Enzymol, 212: 194-219, 1992
Primrose Principles of Genome Analysis, Second Edition, Blackwell Science, 1998.
Rasmussen et al., Anal. Biochem, 198:138-142, 1991.
Richards and Boyer, J. Mol. Biol., 11: 327-340, 1965
Richterich and Church, Method Enzymol., vol 218, 187-222 (1993)
Riley, J., Butler, R., Ogilvie, D., Finniear, R., Jenner, D., Powell, S., Anand, R., Smith, J. C., and Markham, A. F. (1990) Nucleic Acids Res. 18, 2887-2890
Roots et al., Adv Space Res, 9: 45-55, 1989
Rosenthal, A., and Jones, D. S. (1990) Nucleic Acids Res. 18, 3095-3096.

Rudi et al. (1999) BioTechniques 27:1170-1177
Running et al., BioTechniques 8:276-277, 1990.
Sambrook et al., "Molecular Cloning," A Laboratory Manual, 2d Ed., Cold Spring Harbor Laboratory Press, New York, 13.7-13.9:1989.
Schram, Methods Biochem Anal., 34: 203-287 1990.
Shoemaker et al., Nature Genetics 14:450-456, 1996.
Siebert et al. Nucleic Acids Res. 23, 1087-1088, 1995.
Smith et al., Anal. Chem. 62, 882-89, 1990.
Smith, D. R. (1992) PCR Methods Appl., 2, 21-27.
Sterky et al. Journal of Biotechnology 60 (1998) 119-129
Tabor, et al., Proc Natl Acad Sci USA., 84(14):4767-71, 1987.
Thorstenson et al., Genome Research, 8: 848-855, 1998
Tullius, Free Radic Res Commun, 12-13 Pt 2: 521-529, 1991
Unrau, P. and Deugau, K. (1994) Gene, 145, 163-169.
Vos et al., Nucleic Acids Research 23:4407-4414 (1995).
Walker et al. (1992a) PNAS 89:392-396
Walker et al. (1992b) Nuc. Acids Res. 20: 1691-1696.
Williams et al., Science, 246: 1585-87, 1989
Xu et al. Anal. Chem. Vol. 69, 3595-3602, 1997
Zhang, et al. Gurr Gene 253 (2000) 145-150.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of conducting a DNA sequence analysis by fragmenting DNA to provide DNA probes therefrom, the method comprising:
   (a) obtaining a DNA sample comprising primer-linked DNA fragments, the DNA fragments having been prepared by subjecting the DNA sample to thermal fragmentation by heating said sample under conditions to effect fragmentation of DNA molecules in the sample to provide single stranded DNA fragments; and either
      i) forming double-stranded DNA fragments from said single-stranded fragments that include a primer or primers having a known sequence at least at one end of a plurality of the double-stranded DNA fragments, to provide double-stranded primer-linked fragments; or
      ii) providing the DNA probes from said sample by attaching a primer or primers having a known sequence to at least one end of a plurality of the single-stranded DNA fragments, to provide primer-linked single-stranded fragments; and
   (b) conducting a DNA sequence analysis of at least a portion of one or more of said primer-linked DNA fragments or copies thereof.

2. The method of claim 1, wherein said heating is to a temperature of between about 40° C. and 120° C.

3. The method of claim 2, wherein said heating is to a temperature of between about 80° C. and 100° C.

4. The method of claim 3, wherein said heating is to a temperature of between about 90° C. and 100° C.

5. The method of claim 4, wherein said heating is to a temperature of between about 92° C. and 98° C.

6. The method of claim 5, said heating is to a temperature of between about 93° C. and 97° C.

7. The method of claim 6, wherein said heating is to a temperature of between about 94° C. and 96° C.

8. The method of claim 7, wherein said heating is to a temperature of about 95° C.

9. The method of claim 1, wherein said heating of the DNA molecule is in a solution having from 0 to about 100 mM concentration of a salt.

10. The method of claim 9, wherein said heating is in a solution having from about 0 to about 10 mM concentration of salt.

11. The method of claim 10, wherein said heating is in a solution having from about 0.1 to about 1 mM concentration of salt.

12. The method of claim 11, wherein said heating is in a solution having from about 0.1 to about 0.5 mM concentration of salt.

13. The method of claim 1, wherein said heating is in a solution of 10 mM Tris, pH 8.0; 1 mM EDTA.

14. The method of claim 1, wherein said heating is in a solution of water.

15. The method of claim 1, wherein double-stranded DNA fragments are formed from said single-stranded fragments by
   (a) attaching a first primer sequence to one end of a plurality of said single-stranded fragments; and
   (b) forming double-stranded DNA fragments using a second primer complementary to said first primer.

16. The method of claim 15, wherein copies of said double-stranded DNA fragments are prepared using a third primer complementary to a sequence present in said single-stranded fragments in a DNA polymerase reaction.

17. The method of claim 15, wherein copies of said double-stranded DNA fragments are prepared by ligating primers having a known sequence to one or both ends of said double-stranded DNA and forming copies thereof fragments using complementary primers in a DNA polymerase reaction.

18. The method of claim 15, wherein said first primer sequence is a homopolymeric sequence and is attached by a terminal transferase.

19. The method of claim 15, wherein said first primer sequence is attached to one end by ligating a single-stranded adaptor thereto.

20. The method of claim 1, wherein the DNA sequence analysis is performed by sequencing at least a portion of the primer-linked single-stranded fragments or copies thereof.

21. The method of claim 1, wherein said conducting a sequence analysis is further defined as concomitantly sequencing a plurality of primer-linked fragments.

22. The method of claim 1, wherein said conducting a sequence analysis comprises the steps of:
   obtaining a plurality of DNA molecules having overlapping sequences;
   concomitantly sequencing a first region in said plurality of DNA molecules using a primer complementary to a known sequence in said plurality of DNA molecules; and
   concomitantly sequencing a second region in said plurality of DNA molecules using a primer complementary to sequence determined from the sequencing of the first region,
   wherein the next consecutive sequencing of a region in the overlapping series of nucleic acid sequences is produced by initiating sequencing from the sequence obtained in a preceding overlapping sequencing product.

* * * * *

UNITED STATES PATENT AND TRADEMARK OFFICE
CERTIFICATE OF CORRECTION

| | | |
|---|---|---|
| PATENT NO. | : 8,815,504 B2 | Page 1 of 1 |
| APPLICATION NO. | : 12/697886 | |
| DATED | : August 26, 2014 | |
| INVENTOR(S) | : Vladimir L. Makarov et al. | |

It is certified that error appears in the above-identified patent and that said Letters Patent is hereby corrected as shown below:

In title page, item (56) References Cited - Other Publications, delete the 4th reference on page 1 "Barbaux el al., "Use of degenerate oligonucleotide primed PCR (DOP-PCR) for the genotyping of low-concentration DNA samples," *J. Mol. Med.*, 79:329-332, 2001." and replace with --Barbaux et al., "Use of degenerate oligonucleotide primed PCR (DOP-PCR) for the genotyping of low-concentration DNA samples," *J. Mol. Med.*, 79:329-332, 2001.-- therefor.

In the Claims

In claim 6, column 62, line 58, after "of claim 5," insert --wherein--.

In claim 17, column 63, line 28, delete the word "fragments".

Signed and Sealed this
Sixth Day of January, 2015

Michelle K. Lee
*Deputy Director of the United States Patent and Trademark Office*